US009233159B2

(12) United States Patent
Leone-Bay et al.

(10) Patent No.: US 9,233,159 B2
(45) Date of Patent: Jan. 12, 2016

(54) METHODS AND COMPOSITIONS FOR TREATING PAIN

(71) Applicants: MannKind Corporation, Valencia, CA (US); Torrey Pines Institute for Molecular Studies, Port St. Lucie, FL (US)

(72) Inventors: Andrea Leone-Bay, Ridgefield, CT (US); Richard A. Houghten, Vero Beach, FL (US); Joseph J. Guarneri, Stamford, CT (US); Grayson W. Stowell, Gaylordsville, CT (US)

(73) Assignees: MannKind Corporation, Valencia, CA (US); Torrey Pines Institute for Molecular Studies, Port St. Lucie, FL (US)

( * ) Notice: Subject to any disclaimer, the term of this patent is extended or adjusted under 35 U.S.C. 154(b) by 0 days.

(21) Appl. No.: 14/354,092

(22) PCT Filed: Oct. 24, 2012

(86) PCT No.: PCT/US2012/061749
§ 371 (c)(1),
(2) Date: Apr. 24, 2014

(87) PCT Pub. No.: WO2013/063160
PCT Pub. Date: May 2, 2013

(65) Prior Publication Data

US 2014/0302151 A1 Oct. 9, 2014

Related U.S. Application Data

(60) Provisional application No. 61/550,860, filed on Oct. 24, 2011.

(51) Int. Cl.

| | |
|---|---|
| ***A61K 38/04*** | (2006.01) |
| ***A61K 38/07*** | (2006.01) |
| ***A61K 38/08*** | (2006.01) |
| ***A61K 9/14*** | (2006.01) |
| ***C07K 5/10*** | (2006.01) |
| ***C07K 7/06*** | (2006.01) |
| ***A61K 47/22*** | (2006.01) |
| ***A61K 9/00*** | (2006.01) |
| ***A61K 31/495*** | (2006.01) |
| ***A61K 31/198*** | (2006.01) |
| ***A61K 31/401*** | (2006.01) |
| ***A61K 31/405*** | (2006.01) |
| ***C07K 5/107*** | (2006.01) |

(52) U.S. Cl.
CPC ............... *A61K 47/22* (2013.01); *A61K 9/0075* (2013.01); *A61K 9/14* (2013.01); *A61K 31/198* (2013.01); *A61K 31/401* (2013.01); *A61K 31/405* (2013.01); *A61K 31/495* (2013.01); *A61K 38/04* (2013.01); *A61K 38/07* (2013.01); *A61K 38/08* (2013.01); *C07K 5/10* (2013.01); *C07K 5/1016* (2013.01); *C07K 7/06* (2013.01)

(58) Field of Classification Search
CPC ............ A61K 2300/00; A61K 31/198; A61K 31/401; A61K 38/04; A61K 38/07; A61K 38/08; A61K 9/0075; A61K 9/14; C07K 5/10; C07K 7/06
USPC ................................ 514/10.7, 18.4; 424/489
See application file for complete search history.

(56) References Cited

U.S. PATENT DOCUMENTS

| | | | |
|---|---|---|---|
| 2,549,303 | A | 4/1951 | Friden |
| 2,754,276 | A | 7/1956 | Joseph et al. |
| D189,076 | S | 10/1960 | Altman |
| 3,337,740 | A | 8/1967 | Gray et al. |
| 3,407,203 | A | 10/1968 | Buijle |
| 3,518,340 | A | 6/1970 | Raper |
| 3,622,053 | A | 11/1971 | Ryden |
| 3,669,113 | A | 6/1972 | Altounyan et al. |
| 3,823,816 | A | 7/1974 | Controulis et al. |
| 3,823,843 | A | 7/1974 | Stephens et al. |
| 3,856,142 | A | 12/1974 | Vessalo |
| 3,906,950 | A | 9/1975 | Cocozza |
| 3,921,637 | A | 11/1975 | Bennie et al. |
| 3,976,773 | A | 8/1976 | Curran et al. |

(Continued)

FOREIGN PATENT DOCUMENTS

| | | | |
|---|---|---|---|
| CA | 2551182 | C | 8/2010 |
| CN | 101851213 | | 10/2010 |

(Continued)

OTHER PUBLICATIONS

"An inhaled insulin formulation (Technosphere Insulin) effectively improves glycaemic control in patients with type 2 diabetes mellitus." Inpharma Weekly, vol. 1522, Jan. 28, 2006, p. 8.
ACTOS Product Insert. Aug. 2008.
Ahren "GLP-1 and extra-islet effects." Horm. Med Res 36:842, 2004.
Ahren B et al. "Characterization of GLP-1 effects on b-cell function after meal ingestion in humans." Diabetes Care 26:2860, 2003.
Ahren B., Glucagon-like peptide-1 (GLP-1): a gut hormone of potential interest in the treatment of diabetes. BioEssays, V. 20, pp. 642-651 (1998).
Akerlund et al., Diketopiperazine-based polymers from common acids. Journal of Applied Polymer Science (2000), 78(12), 2213-2218.

(Continued)

*Primary Examiner* — Julie Ha
(74) *Attorney, Agent, or Firm* — K&L Gates LLP; Louis C. Cullman; Hal Gibson

(57) ABSTRACT

Methods and compositions for treating pain are disclosed. The compositions are based on dry powders comprising microparticles of diketopiperazines and an analgesic active agent. The analgesic in the compositions comprises one or more peptide analgesics or derivatives thereof, which are administered to a subject using a pulmonary inhalation drug delivery system comprising a dry powder inhaler and the analgesic composition. The present compositions produce fewer side effects associated with current opioid therapy.

25 Claims, 6 Drawing Sheets

(56) References Cited

U.S. PATENT DOCUMENTS 3,980,074 A 9/1976 Watt et al.
3,998,226 A 12/1976 Harris
4,013,075 A 3/1977 Cocozza
4,018,619 A 4/1977 Webster et al.
4,022,749 A 5/1977 Kuechler
4,040,536 A 8/1977 Schwarz
4,047,525 A 9/1977 Kulessa et al.
4,078,128 A 3/1978 Hoyt et al.
4,091,077 A 5/1978 Smith et al.
4,098,273 A 7/1978 Glenn
4,102,953 A 7/1978 Johnson et al.
4,110,240 A 8/1978 Leo et al.
4,148,308 A 4/1979 Sayer
4,153,689 A 5/1979 Hirai
D252,707 S 8/1979 Besnard
4,175,556 A 11/1979 Freezer
4,187,129 A 2/1980 Bost et al.
4,196,196 A 4/1980 Tiholiz
4,206,758 A 6/1980 Hallworth et al.
4,210,140 A 7/1980 James et al.
4,211,769 A 7/1980 Okada
4,268,460 A 5/1981 Boiarski et al.
4,272,398 A 6/1981 Jaffe
4,275,820 A 6/1981 LeBlond
4,289,759 A 9/1981 Heavener
4,294,829 A 10/1981 Suzuki
4,300,546 A 11/1981 Kruber
4,356,167 A 10/1982 Kelly
D269,463 S 6/1983 Young et al.
4,407,525 A 10/1983 Hoppe
4,456,007 A 6/1984 Nakao et al.
4,481,139 A * 11/1984 Folkers et al. ................ 530/327
4,483,922 A 11/1984 Carpenter
D276,654 S 12/1984 Snellman-Wasenius et al.
4,487,327 A 12/1984 Grayson
4,524,769 A 6/1985 Wetterlin
4,526,804 A 7/1985 Escallon
4,534,345 A 8/1985 Wetterlin
D282,209 S 1/1986 Newell et al.
4,581,020 A 4/1986 Mittleman
4,592,348 A 6/1986 Waters, IV et al.
4,613,500 A 9/1986 Suzuki
4,615,817 A 10/1986 McCoy
4,624,861 A 11/1986 Yale et al.
4,637,996 A 1/1987 Konishi
D288,852 S 3/1987 Miyoshi
4,659,696 A 4/1987 Hirai
4,668,218 A 5/1987 Virtanen
4,671,954 A * 6/1987 Goldberg et al. ............ 424/1.37
4,681,752 A 7/1987 Melillo
D295,321 S 4/1988 Hallworth
4,742,156 A * 5/1988 Wright .......................... 530/328
4,757,066 A 7/1988 Shiokari et al.
4,792,451 A 12/1988 Kim
4,811,731 A 3/1989 Newell et al.
D301,273 S 5/1989 Leonard
4,835,312 A 5/1989 Itoh et al.
4,841,964 A 6/1989 Hurka et al.
4,849,227 A 7/1989 Cho
4,861,627 A 8/1989 Mathiowitz
4,866,051 A 9/1989 Hunt et al.
4,873,087 A 10/1989 Morishita et al.
D304,975 S 12/1989 Movitz
4,887,722 A 12/1989 Greenward, Sr.
4,900,730 A 2/1990 Miyauchi
4,907,583 A 3/1990 Wetterlin et al.
4,925,673 A 5/1990 Steiner
4,926,852 A 5/1990 Zoltan et al.
4,927,555 A 5/1990 Colarusso, Jr.
4,927,928 A 5/1990 Shroot et al.
4,946,828 A 8/1990 Markussen
4,981,295 A 1/1991 Belman et al.
4,983,402 A 1/1991 Steiner et al.
4,984,158 A 1/1991 Hillsman
4,991,605 A 2/1991 Keritsis
4,998,624 A 3/1991 Capes et al.
5,006,343 A 4/1991 Benson
D316,902 S 5/1991 Hoelfing
5,021,376 A 6/1991 Nienburg et al.
5,027,806 A 7/1991 Zoltan et al.
5,042,975 A 8/1991 Chien
D321,570 S 11/1991 Blasdell et al.
5,067,500 A 11/1991 Keritsis
5,069,204 A 12/1991 Smith et al.
5,074,418 A 12/1991 Buan et al.
5,075,027 A 12/1991 Dixit et al.
5,098,590 A 3/1992 Dixit et al.
5,105,291 A 4/1992 Matsumoto et al.
D326,517 S 5/1992 Funai et al.
5,110,823 A 5/1992 Hamaguchi et al.
5,118,666 A 6/1992 Habener
5,120,712 A 6/1992 Habener
5,124,291 A 6/1992 Bremer et al.
5,131,539 A 7/1992 Karita et al.
5,145,684 A 9/1992 Liversidge et al.
5,152,284 A 10/1992 Valentini et al.
D331,106 S 11/1992 Fuchs
5,167,506 A 12/1992 Kilis et al.
5,170,801 A 12/1992 Casper et al.
5,188,837 A 2/1993 Domb
5,201,308 A 4/1993 Newhouse
5,203,768 A 4/1993 Haak et al.
5,204,108 A 4/1993 Illum
D337,636 S 7/1993 Kocinski
D338,062 S 8/1993 Yair
D338,268 S 8/1993 Kobayashi et al.
5,239,992 A 8/1993 Bougamont et al.
5,244,653 A 9/1993 Berke et al.
5,250,287 A 10/1993 Cocozza
5,260,306 A 11/1993 Boardman et al.
5,270,305 A 12/1993 Palmer
5,287,850 A 2/1994 Haber et al.
D344,796 S 3/1994 Sochon et al.
D344,797 S 3/1994 Sochon et al.
D345,013 S 3/1994 Huck et al.
5,301,666 A 4/1994 Lerk et al.
5,306,453 A 4/1994 Shulman
D347,057 S 5/1994 Yair
D348,100 S 6/1994 Clarke
5,320,094 A 6/1994 Laube et al.
D348,928 S 7/1994 Ashley et al.
D348,929 S 7/1994 Paton
5,327,883 A 7/1994 Williams et al.
5,328,464 A 7/1994 Kriesel et al.
5,331,953 A 7/1994 Andersson et al.
5,333,106 A 7/1994 Lanpher et al.
D349,572 S 8/1994 Jagnandan et al.
D350,193 S 8/1994 Huck et al.
5,337,740 A 8/1994 Armstrong et al.
D350,602 S 9/1994 Hobbs et al.
D350,821 S 9/1994 Wright et al.
5,351,683 A 10/1994 Chiesi et al.
5,352,461 A 10/1994 Feldstein et al.
5,354,562 A 10/1994 Platz
5,358,734 A 10/1994 Lenox et al.
D352,107 S 11/1994 Meier et al.
5,360,614 A 11/1994 Fox et al.
5,363,842 A 11/1994 Mishelevich et al.
5,364,838 A 11/1994 Rubsamen
5,372,128 A 12/1994 Haber et al.
D355,029 S 1/1995 Kinneir et al.
5,385,904 A 1/1995 Andersson et al.
5,394,868 A 3/1995 Ambrosio et al.
5,401,516 A 3/1995 Milstein et al.
D357,603 S 4/1995 Wolff
5,404,871 A 4/1995 Goodman et al.
D358,880 S 5/1995 Mulhauser et al.
5,413,804 A 5/1995 Rhodes
D359,153 S 6/1995 Viggiano
D359,555 S 6/1995 Funai et al.
5,424,286 A 6/1995 Eng
5,437,271 A 8/1995 Hodson et al.
5,443,841 A 8/1995 Milstein et al.
D362,500 S 9/1995 Cook et al.

(56) References Cited

U.S. PATENT DOCUMENTS 5,447,150 A 9/1995 Bacon
5,447,151 A 9/1995 Bruna et al.
5,447,728 A 9/1995 Milstein et al.
5,451,410 A 9/1995 Milstein et al.
D363,775 S 10/1995 Hobbs
5,454,871 A 10/1995 Liaw et al.
5,455,335 A 10/1995 Kahne et al.
5,458,135 A 10/1995 Patton et al.
5,466,971 A 11/1995 Higuchi
5,469,750 A 11/1995 Lloyd et al.
5,476,093 A 12/1995 Laniken
5,477,285 A 12/1995 Riddle et al.
D365,876 S 1/1996 Chawla
5,482,032 A 1/1996 Smith et al.
5,482,927 A 1/1996 Maniar
5,483,954 A 1/1996 Mecikalski
5,484,606 A 1/1996 Dhaber
5,487,378 A 1/1996 Robertson et al.
5,492,112 A 2/1996 Mecikalski et al.
D368,364 S 4/1996 Reitano et al.
5,503,144 A 4/1996 Bacon
5,503,852 A 4/1996 Steiner et al.
5,505,194 A 4/1996 Adjei et al.
5,506,203 A 4/1996 Backstrom et al.
D370,255 S 5/1996 Yamamoto et al.
5,514,646 A 5/1996 Chance et al.
5,518,998 A 5/1996 Backstrom et al.
5,524,613 A 6/1996 Haber et al.
5,532,461 A 7/1996 Crummenauer et al.
5,533,502 A 7/1996 Piper
5,533,505 A 7/1996 Kallstrand et al.
5,542,411 A 8/1996 Rex
5,542,539 A 8/1996 Early
5,545,618 A 8/1996 Buckley et al.
5,547,929 A 8/1996 Anderson, Jr. et al.
5,562,909 A 10/1996 Allcock et al.
5,562,918 A 10/1996 Stimpson
5,568,884 A 10/1996 Bruna
5,570,810 A 11/1996 Lambelet, Jr. et al.
5,571,795 A 11/1996 Kahne et al.
5,574,008 A 11/1996 Johnson et al.
5,577,497 A 11/1996 Mecikalski et al.
5,578,323 A 11/1996 Milstein et al.
5,584,417 A 12/1996 Graf et al.
D377,215 S 1/1997 Rand
D377,686 S 1/1997 Waldeck et al.
5,595,175 A 1/1997 Malcher et al.
5,596,701 A 1/1997 Augusteijn et al.
D377,861 S 2/1997 Jacober
5,598,835 A 2/1997 von Schrader
5,601,846 A 2/1997 Milstein et al.
5,610,271 A * 3/1997 Dooley et al. ................. 530/328
5,614,492 A 3/1997 Habener
5,617,844 A 4/1997 King
5,619,984 A 4/1997 Hodson et al.
5,622,164 A 4/1997 Kilis et al.
5,622,166 A 4/1997 Eisele et al.
5,623,724 A 4/1997 Gurkovich et al.
5,623,920 A 4/1997 Bryant
D379,506 S 5/1997 Maher
5,629,020 A 5/1997 Leone-Bay
5,631,224 A 5/1997 Efendic et al.
5,632,971 A 5/1997 Yang
5,634,900 A 6/1997 Makino et al.
5,641,861 A 6/1997 Dooley et al.
D381,416 S 7/1997 Hansson et al.
5,642,727 A 7/1997 Datta et al.
5,642,728 A 7/1997 Andersson et al.
5,643,957 A 7/1997 Leone-Bay et al.
5,645,051 A 7/1997 Schultz
5,651,359 A 7/1997 Bougamont et al.
5,653,961 A 8/1997 McNally et al.
5,655,516 A 8/1997 Goodman et al.
5,655,523 A 8/1997 Hodson et al.
5,657,748 A 8/1997 Braithwaite
5,658,878 A 8/1997 Backstrom et al.
5,660,169 A 8/1997 Kallstrand et al.
5,672,581 A 9/1997 Rubsamen et al.
5,673,686 A 10/1997 Villax et al.
5,679,377 A 10/1997 Bernstein et al.
5,687,710 A 11/1997 Ambrosio et al.
5,690,910 A 11/1997 Ahmed et al.
5,693,338 A 12/1997 Milstein
5,699,789 A 12/1997 Hendricks
D389,238 S 1/1998 Kirk, III et al.
D389,570 S 1/1998 Savolainen
5,705,483 A 1/1998 Galloway et al.
D390,651 S 2/1998 Smith et al.
D390,653 S 2/1998 Blasdell et al.
5,714,007 A 2/1998 Pletcher et al.
5,714,167 A 2/1998 Milstein et al.
5,727,546 A 3/1998 Clarke et al.
5,740,793 A 4/1998 Hodson et al.
5,740,794 A 4/1998 Smith et al.
5,746,197 A 5/1998 Williams
5,746,227 A 5/1998 Rose et al.
5,747,445 A 5/1998 Backstrom et al.
5,752,505 A 5/1998 Ohki et al.
5,755,218 A 5/1998 Johansson et al.
D395,147 S 6/1998 Vidgren et al.
D395,499 S 6/1998 Eisele et al.
5,758,638 A 6/1998 Kreamer
5,763,396 A 6/1998 Weiner et al.
5,766,620 A 6/1998 Heiber et al.
5,766,633 A 6/1998 Milstein et al.
5,769,073 A 6/1998 Eason et al.
5,772,085 A 6/1998 Bryant et al.
RE35,862 E 7/1998 Steiner et al.
5,775,320 A 7/1998 Patton et al.
5,785,049 A 7/1998 Smith et al.
5,785,989 A 7/1998 Stanley et al.
D397,435 S 8/1998 Naumann
5,792,451 A 8/1998 Sarubbi et al.
5,794,613 A 8/1998 Piskorski
5,797,391 A 8/1998 Cook et al.
D398,992 S 9/1998 Feret
5,799,821 A 9/1998 Lambelet, Jr. et al.
5,807,315 A 9/1998 van Antwerp et al.
5,809,997 A 9/1998 Wolf
5,811,127 A 9/1998 Milstein et al.
5,813,397 A 9/1998 Goodman et al.
5,824,345 A 10/1998 Milstein et al.
5,839,429 A 11/1998 Marnfeldt et al.
5,840,279 A 11/1998 Narodylo et al.
5,840,340 A 11/1998 Milstein et al.
5,846,447 A 12/1998 Beatty
5,848,589 A 12/1998 Welnetz
5,849,322 A 12/1998 Ebert et al.
5,857,457 A 1/1999 Hyppola
5,858,099 A 1/1999 Sun et al.
5,865,012 A 2/1999 Hansson et al.
5,874,064 A 2/1999 Edwards et al.
5,875,776 A 3/1999 Vaghefi
5,877,174 A 3/1999 Ono et al.
5,881,719 A 3/1999 Gottenauer et al.
5,881,721 A 3/1999 Bunce et al.
5,884,620 A 3/1999 Gonda et al.
5,888,477 A 3/1999 Gonda et al.
5,896,855 A 4/1999 Hobbs et al.
5,901,703 A 5/1999 Ohki et al.
5,904,139 A 5/1999 Hauser
D410,541 S 6/1999 Moulin
D411,005 S 6/1999 Coe
5,908,639 A 6/1999 Simpkin et al.
5,912,011 A 6/1999 Makino et al.
5,918,594 A 7/1999 Asking et al.
5,919,897 A 7/1999 Dooley et al.
5,921,237 A 7/1999 Eisele et al.
5,924,419 A 7/1999 Kotliar
5,929,027 A 7/1999 Takama et al.
D412,572 S 8/1999 Gray
D412,744 S 8/1999 Braithwaite
D412,978 S 8/1999 Cameron
D412,979 S 8/1999 Weinstein et al.

(56) References Cited

U.S. PATENT DOCUMENTS

| | | | |
|---|---|---|---|
| 5,934,273 | A | 8/1999 | Andersson et al. |
| 5,942,242 | A | 8/1999 | Mizushima et al. |
| 5,948,749 | A | 9/1999 | Igarashi et al. |
| 5,952,008 | A | 9/1999 | Backstrom et al. |
| 5,954,047 | A | 9/1999 | Armer et al. |
| 5,965,701 | A | 10/1999 | Junien et al. |
| 5,971,951 | A | 10/1999 | Ruskewicz |
| D416,085 | S | 11/1999 | Forssell et al. |
| D416,621 | S | 11/1999 | Forssell et al. |
| D416,998 | S | 11/1999 | Hodson et al. |
| D417,271 | S | 11/1999 | Denyer et al. |
| 5,975,347 | A | 11/1999 | Lambelet, Jr. et al. |
| 5,976,569 | A | 11/1999 | Milstein |
| 5,976,574 | A | 11/1999 | Gordon |
| 5,977,071 | A | 11/1999 | Galloway et al. |
| 5,980,865 | A | 11/1999 | Ahmed et al. |
| 5,981,488 | A | 11/1999 | Hoffman |
| 5,983,893 | A | 11/1999 | Wetterlin |
| 5,985,248 | A | 11/1999 | Gordon et al. |
| 5,985,309 | A | 11/1999 | Edwards et al. |
| 5,990,077 | A | 11/1999 | Drucker |
| D417,732 | S | 12/1999 | Dagsland et al. |
| D417,912 | S | 12/1999 | Dagsland et al. |
| 5,996,577 | A | 12/1999 | Ohki et al. |
| 5,997,848 | A | 12/1999 | Patton et al. |
| 6,001,336 | A | 12/1999 | Gordon |
| 6,006,747 | A | 12/1999 | Eisele et al. |
| 6,006,753 | A | 12/1999 | Efendic |
| D418,600 | S | 1/2000 | Haerle |
| D420,736 | S | 2/2000 | Moulin |
| 6,026,809 | A | 2/2000 | Abrams et al. |
| 6,029,663 | A | 2/2000 | Eisele et al. |
| D421,800 | S | 3/2000 | Doat |
| 6,039,208 | A | 3/2000 | Lambelet et al. |
| 6,043,214 | A | 3/2000 | Jensen et al. |
| 6,045,828 | A | 4/2000 | Bystrom et al. |
| 6,051,256 | A | 4/2000 | Platz et al. |
| 6,051,551 | A | 4/2000 | Hughes et al. |
| 6,055,980 | A | 5/2000 | Mecikalski et al. |
| 6,056,169 | A | 5/2000 | Bruna et al. |
| 6,060,069 | A | 5/2000 | Hill et al. |
| 6,063,910 | A | 5/2000 | Debenedetti et al. |
| 6,071,497 | A | 6/2000 | Steiner et al. |
| 6,073,629 | A | 6/2000 | Hardy et al. |
| 6,077,543 | A | 6/2000 | Gordon et al. |
| 6,080,762 | A | 6/2000 | Allen et al. |
| D428,486 | S | 7/2000 | Schuckmann |
| 6,085,745 | A | 7/2000 | Levander et al. |
| 6,087,334 | A | 7/2000 | Beeley et al. |
| 6,087,351 | A | 7/2000 | Nyce |
| 6,089,228 | A | 7/2000 | Smith et al. |
| 6,095,136 | A | 8/2000 | Virtanen |
| 6,098,618 | A | 8/2000 | Jennings et al. |
| 6,099,517 | A | 8/2000 | Daugherty |
| 6,102,035 | A | 8/2000 | Asking et al. |
| 6,105,571 | A | 8/2000 | Coffee |
| 6,105,574 | A | 8/2000 | Jahnsson |
| 6,109,261 | A | 8/2000 | Clarke et al. |
| 6,109,481 | A | 8/2000 | Alexander et al. |
| 6,116,237 | A | 9/2000 | Schultz |
| 6,116,238 | A | 9/2000 | Jackson et al. |
| 6,116,239 | A | 9/2000 | Volgyesi |
| 6,119,684 | A | 9/2000 | Nohl et al. |
| 6,119,688 | A | 9/2000 | Whaley et al. |
| 6,131,567 | A | 10/2000 | Gonda et al. |
| 6,132,766 | A | 10/2000 | Sankaram et al. |
| 6,133,235 | A | 10/2000 | Galloway et al. |
| 6,142,145 | A | 11/2000 | Dagsland |
| 6,152,130 | A | 11/2000 | Abrams |
| 6,153,613 | A | 11/2000 | Ono et al. |
| 6,155,423 | A | 12/2000 | Katzne et al. |
| 6,156,114 | A | 12/2000 | Bell et al. |
| 6,158,431 | A | 12/2000 | Poole |
| 6,159,360 | A | 12/2000 | Gerteis et al. |
| RE37,053 | E | 2/2001 | Hanes et al. |
| 6,182,655 | B1 | 2/2001 | Keller et al. |
| 6,187,291 | B1 | 2/2001 | Weinstein et al. |
| 6,191,102 | B1 | 2/2001 | DiMarchi et al. |
| 6,192,876 | B1 | 2/2001 | Denyer et al. |
| 6,193,844 | B1 | 2/2001 | McLaughlin et al. |
| 6,193,957 | B1 | 2/2001 | Ahmed |
| D438,612 | S | 3/2001 | Suh |
| D439,325 | S | 3/2001 | Frost |
| D439,656 | S | 3/2001 | Andersson et al. |
| 6,198,847 | B1 | 3/2001 | Washizawa |
| D441,446 | S | 5/2001 | Dagsland et al. |
| D441,859 | S | 5/2001 | Pera |
| D442,685 | S | 5/2001 | Sladek |
| 6,235,725 | B1 | 5/2001 | Ahmed |
| D444,226 | S | 6/2001 | Geert-Jensen et al. |
| 6,250,300 | B1 | 6/2001 | Andersson et al. |
| 6,254,854 | B1 | 7/2001 | Edwards et al. |
| 6,257,232 | B1 | 7/2001 | Andersson et al. |
| 6,258,816 | B1 | 7/2001 | Singh et al. |
| 6,263,871 | B1 | 7/2001 | Brown et al. |
| 6,269,952 | B1 | 8/2001 | Watt et al. |
| 6,273,084 | B1 | 8/2001 | Frid |
| 6,273,085 | B1 | 8/2001 | Eisele et al. |
| 6,273,086 | B1 | 8/2001 | Ohki et al. |
| 6,277,819 | B1 | 8/2001 | Efendic |
| 6,279,511 | B1 | 8/2001 | Loughnane |
| D448,076 | S | 9/2001 | von Schuckmann |
| 6,286,506 | B1 | 9/2001 | MacAndrew et al. |
| 6,286,507 | B1 | 9/2001 | Jahnsson |
| 6,294,204 | B1 | 9/2001 | Rossling et al. |
| D449,684 | S | 10/2001 | Christup et al. |
| 6,298,846 | B1 | 10/2001 | Ohki et al. |
| 6,298,847 | B1 | 10/2001 | Datta et al. |
| D450,117 | S | 11/2001 | Braithwaite et al. |
| D451,597 | S | 12/2001 | Suh |
| 6,328,034 | B1 | 12/2001 | Eisele et al. |
| 6,331,318 | B1 | 12/2001 | Milstein |
| D452,910 | S | 1/2002 | Braithwaite et al. |
| 6,335,316 | B1 | 1/2002 | Hughes et al. |
| D453,264 | S | 2/2002 | Acevedo, Jr. |
| 6,347,629 | B1 | 2/2002 | Braithwaite |
| 6,348,447 | B1 | 2/2002 | Hellstrom et al. |
| 6,357,442 | B1 | 3/2002 | Casper et al. |
| 6,358,058 | B1 | 3/2002 | Strupat et al. |
| 6,358,924 | B1 | 3/2002 | Hoffmann |
| 6,360,743 | B1 | 3/2002 | Andersson et al. |
| 6,360,929 | B1 | 3/2002 | McCarthy |
| D455,208 | S | 4/2002 | Bacon et al. |
| 6,363,932 | B1 | 4/2002 | Forchione et al. |
| 6,365,190 | B1 | 4/2002 | Gordon et al. |
| 6,372,258 | B1 | 4/2002 | Platz et al. |
| 6,375,975 | B1 | 4/2002 | Modi |
| 6,380,357 | B2 | 4/2002 | Hermeling et al. |
| 6,386,195 | B1 | 5/2002 | Coffee |
| 6,388,053 | B1 | 5/2002 | Galloway et al. |
| 6,394,085 | B1 | 5/2002 | Hardy et al. |
| 6,395,300 | B1 | 5/2002 | Straub et al. |
| 6,395,744 | B1 | 5/2002 | Adams et al. |
| 6,395,774 | B1 | 5/2002 | Milstein |
| 6,410,513 | B1 | 6/2002 | Galloway et al. |
| D460,173 | S | 7/2002 | Harrison |
| 6,415,784 | B1 | 7/2002 | Christrup et al. |
| 6,418,926 | B1 | 7/2002 | Chawla |
| 6,423,344 | B1 | 7/2002 | Platz et al. |
| D461,239 | S | 8/2002 | Cassidy |
| 6,427,688 | B1 | 8/2002 | Ligotke et al. |
| 6,428,771 | B1 | 8/2002 | Steiner et al. |
| 6,428,805 | B1 | 8/2002 | Dohi et al. |
| 6,432,383 | B1 | 8/2002 | Modi |
| 6,436,443 | B2 | 8/2002 | Edwards et al. |
| 6,439,227 | B1 | 8/2002 | Myrman et al. |
| 6,440,463 | B1 | 8/2002 | Feldstein et al. |
| 6,441,172 | B1 | 8/2002 | Nefzi et al. |
| D463,544 | S | 9/2002 | Engelbreth et al. |
| 6,443,143 | B1 | 9/2002 | Ishida et al. |
| 6,444,226 | B1 | 9/2002 | Steiner et al. |
| 6,446,626 | B1 | 9/2002 | Virtanen |
| 6,446,627 | B1 | 9/2002 | Bowman et al. |
| 6,447,750 | B1 | 9/2002 | Cutie et al. |

(56) References Cited

U.S. PATENT DOCUMENTS 6,447,751 B1 9/2002 Weinstein et al.
6,447,753 B2 9/2002 Edwards et al.
6,451,337 B1 9/2002 Smith et al.
6,457,470 B1 10/2002 Coffee
6,468,507 B1 10/2002 Cutie et al.
6,470,884 B2 10/2002 Horlin
6,479,049 B1 11/2002 Platz et al.
6,484,715 B1 11/2002 Ritsche et al.
6,484,717 B1 11/2002 Dagsland et al.
D469,527 S 1/2003 Keller et al.
6,503,480 B1 1/2003 Edwards et al.
6,509,006 B1 1/2003 Platz et al.
6,509,313 B1 1/2003 Smith
D469,866 S 2/2003 Albulet et al.
6,514,482 B1 2/2003 Bartus et al.
6,518,239 B1 2/2003 Kuo et al.
D471,273 S 3/2003 Albulet et al.
6,528,096 B1 3/2003 Musa et al.
6,532,437 B1 3/2003 Clardy et al.
6,536,427 B2 3/2003 Davies et al.
D473,298 S 4/2003 Bowman et al.
D473,640 S 4/2003 Cuffaro et al.
6,540,672 B1 4/2003 Simonsen et al.
6,540,982 B1 4/2003 Adjei et al.
6,540,983 B1 4/2003 Adjei et al.
6,543,448 B1 4/2003 Axford et al.
6,546,929 B2 4/2003 Burr et al.
6,555,521 B2 4/2003 Hermeling et al.
D474,536 S 5/2003 Albulet et al.
D475,133 S 5/2003 McLuckie
6,557,549 B2 5/2003 Schmidt et al.
6,561,186 B2 5/2003 Casper et al.
6,567,686 B2 5/2003 Sexton
6,568,390 B2 5/2003 Nichols et al.
6,569,406 B2 5/2003 Stevenson et al.
6,571,793 B1 6/2003 Nilsson et al.
6,572,893 B2 6/2003 Gordon et al.
6,575,160 B1 6/2003 Volgyesi
6,575,162 B1 6/2003 Rand
6,578,571 B1 6/2003 Watt
6,582,728 B1 6/2003 Platz et al.
6,583,111 B1 6/2003 DiMarchi
D477,665 S 7/2003 Myrman et al.
6,589,560 B2 7/2003 Foster et al.
6,591,832 B1 7/2003 DeJonge
6,592,904 B2 7/2003 Platz et al.
6,595,205 B2 7/2003 Andersson et al.
6,595,208 B1 7/2003 Coffee et al.
D478,983 S 8/2003 Whitehall et al.
6,606,992 B1 8/2003 Smith et al.
D479,745 S 9/2003 Albulet et al.
6,613,308 B2 9/2003 Bartus et al.
6,615,987 B1 9/2003 Greenhill et al.
6,620,910 B1 9/2003 Calas et al.
6,626,173 B2 9/2003 Genova et al.
D480,806 S 10/2003 Engelbreth et al.
6,630,169 B1 10/2003 Bot et al.
6,632,258 B1 10/2003 Wheelock et al.
6,632,456 B1 10/2003 Backstrom et al.
6,635,283 B2 10/2003 Edwards et al.
6,637,431 B2 10/2003 Ekelius et al.
6,640,050 B2 10/2003 Nichols et al.
6,644,309 B2 11/2003 Casper et al.
6,645,468 B2 11/2003 Cutie et al.
6,645,504 B1 11/2003 Weiner et al.
6,652,838 B2 11/2003 Weinstein et al.
6,652,885 B2 11/2003 Steiner et al.
D483,860 S 12/2003 Knoch
6,655,379 B2 12/2003 Clark et al.
6,655,380 B1 12/2003 Andersson et al.
6,655,381 B2 12/2003 Keane et al.
6,660,716 B1 12/2003 Yakubu-Madus et al.
6,663,898 B2 12/2003 Milstein
6,668,826 B1 12/2003 Myrman et al.
6,672,304 B1 1/2004 Casper et al.
6,676,931 B2 1/2004 Dugger, III
6,679,255 B2 1/2004 Pera
6,681,767 B1 1/2004 Patton et al.
6,681,768 B2 1/2004 Haaije de Boer et al.
6,685,967 B1 2/2004 Patton et al.
6,698,421 B2 3/2004 Attolini
6,701,917 B2 3/2004 O'Leary
6,703,361 B2 3/2004 Weiner et al.
6,703,365 B2 3/2004 Galloway et al.
6,703,381 B1 3/2004 Ekwuribe et al.
6,705,313 B2 3/2004 Niccolai
6,715,486 B2 4/2004 Gieschen et al.
6,715,487 B2 4/2004 Nichols et al.
6,718,972 B2 4/2004 O'Leary
6,720,407 B1 4/2004 Hughes et al.
6,722,363 B1 4/2004 von Schuckmann
D489,448 S 5/2004 Shayan
6,729,324 B2 5/2004 Casper et al.
6,729,328 B2 5/2004 Goldemann
6,737,045 B2 5/2004 Patton
6,745,761 B2 6/2004 Christrup et al.
6,747,006 B2 6/2004 Efendic
6,748,946 B1 6/2004 Rand et al.
6,748,947 B2 6/2004 Keane et al.
6,752,145 B1 6/2004 Bonney et al.
6,755,190 B2 6/2004 Rasmussen
D492,769 S 7/2004 Hatanaka
D493,220 S 7/2004 Burge et al.
D493,519 S 7/2004 Jonsson et al.
6,774,112 B2 8/2004 Gougoutas
6,787,152 B2 9/2004 Kirby et al.
6,790,496 B1 9/2004 Levander et al.
6,792,945 B2 9/2004 Davies et al.
6,799,572 B2 10/2004 Nichols et al.
6,800,643 B2 10/2004 Cuenoud et al.
6,803,044 B1 10/2004 Catania et al.
6,821,949 B2 11/2004 Bridon et al.
6,823,863 B2 11/2004 Huxham et al.
D499,802 S 12/2004 Pinon et al.
6,830,046 B2 12/2004 Blakley et al.
6,838,075 B2 1/2005 Stevenson et al.
6,838,076 B2 1/2005 Patton et al.
6,847,595 B2 1/2005 Tanaka
6,848,443 B2 2/2005 Schmidt et al.
6,849,708 B1 2/2005 Habener
6,852,690 B1 2/2005 Nauck et al.
6,858,199 B1 2/2005 Edwards et al.
6,860,262 B2 3/2005 Christrup et al.
6,866,037 B1 3/2005 Aslin et al.
6,871,646 B2 3/2005 Keane et al.
6,871,647 B2 3/2005 Allan et al.
6,880,554 B1 4/2005 Coffee
6,881,423 B2 4/2005 Dohi et al.
6,884,435 B1 4/2005 O'Hagan et al.
6,887,459 B1 5/2005 Haeberlin
6,887,849 B2 5/2005 Bridon et al.
6,889,687 B1 5/2005 Olsson
6,892,728 B2 5/2005 Helgesson et al.
6,896,906 B2 5/2005 Hastedt et al.
6,904,907 B2 6/2005 Speldrich et al.
6,906,030 B2 6/2005 Milstein
6,916,354 B2 7/2005 Elliott
6,918,991 B2 7/2005 Chickering, III et al.
6,921,458 B2 7/2005 Chickering, III et al.
6,921,528 B2 7/2005 Edwards et al.
6,923,175 B2 8/2005 Poole et al.
D509,296 S 9/2005 Minshull et al.
D509,898 S 9/2005 Bunce et al.
6,948,496 B2 9/2005 Eason et al.
6,949,258 B2 9/2005 Zhang
6,951,215 B1 10/2005 Hoffman
6,953,812 B2 10/2005 Joregenson et al.
D511,208 S 11/2005 Pardonge et al.
6,962,006 B2 11/2005 Chickering, III et al.
D512,777 S 12/2005 Beisner et al.
6,979,437 B2 12/2005 Bartus et al.
D514,222 S 1/2006 Andersson et al.
6,981,499 B2 1/2006 Andersson et al.
6,989,155 B1 1/2006 Ganderton et al.

(56) References Cited

U.S. PATENT DOCUMENTS

| | | | |
|---|---|---|---|
| 6,991,779 | B2 | 1/2006 | Steiner et al. |
| D515,696 | S | 2/2006 | Lucking et al. |
| D516,211 | S | 2/2006 | Minshull et al. |
| 6,998,387 | B1 | 2/2006 | Goke et al. |
| D518,170 | S | 3/2006 | Clarke et al. |
| D518,171 | S | 3/2006 | Anderson et al. |
| 7,022,674 | B2 | 4/2006 | DeFelippis et al. |
| 7,025,056 | B2 | 4/2006 | Eason et al. |
| 7,028,686 | B2 | 4/2006 | Gonda et al. |
| 7,030,084 | B2 | 4/2006 | Ekwuribe et al. |
| 7,032,593 | B2 | 4/2006 | Johnston et al. |
| 7,035,294 | B2 | 4/2006 | Dove et al. |
| 7,047,967 | B2 | 5/2006 | Knudsen |
| 7,048,098 | B1 | 5/2006 | Moradian |
| 7,060,274 | B2 | 6/2006 | Blumberg et al. |
| 7,067,129 | B2 | 6/2006 | Blumberg et al. |
| 7,077,130 | B2 | 7/2006 | Nichols et al. |
| 7,080,642 | B2 | 7/2006 | Hodson et al. |
| 7,084,243 | B2 | 8/2006 | Glaesner et al. |
| 7,093,594 | B2 | 8/2006 | Harrison et al. |
| 7,093,595 | B2 | 8/2006 | Nesbitt |
| D527,817 | S | 9/2006 | Ziegler et al. |
| 7,101,843 | B2 | 9/2006 | Glaesner et al. |
| 7,101,866 | B2 | 9/2006 | Biggadike et al. |
| 7,107,988 | B2 | 9/2006 | Pinon et al. |
| D529,604 | S | 10/2006 | Young et al. |
| 7,128,067 | B2 | 10/2006 | Byron et al. |
| 7,131,441 | B1 | 11/2006 | Keller et al. |
| 7,132,115 | B2 | 11/2006 | Musa et al. |
| 7,140,365 | B2 | 11/2006 | Poole et al. |
| D533,268 | S | 12/2006 | Olfati |
| 7,143,764 | B1 | 12/2006 | Dagsland et al. |
| 7,143,765 | B2 | 12/2006 | Asking et al. |
| 7,144,863 | B2 | 12/2006 | DeFelippis et al. |
| 7,146,978 | B2 | 12/2006 | Edwards et al. |
| 7,151,456 | B2 | 12/2006 | Godfrey |
| 7,163,014 | B2 | 1/2007 | Nichols et al. |
| D537,522 | S | 2/2007 | Cox et al. |
| 7,171,965 | B2 | 2/2007 | Young et al. |
| 7,172,768 | B2 | 2/2007 | Hastedt et al. |
| 7,179,788 | B2 | 2/2007 | DeFelippis et al. |
| D537,936 | S | 3/2007 | Cox et al. |
| D538,423 | S | 3/2007 | Berube et al. |
| 7,185,650 | B2 | 3/2007 | Huber et al. |
| 7,198,806 | B2 | 4/2007 | Berndt |
| 7,211,557 | B2 | 5/2007 | DiMarchi et al. |
| 7,219,664 | B2 | 5/2007 | Ruckdeschel et al. |
| 7,223,728 | B2 | 5/2007 | Yakubu-Madus et al. |
| D544,093 | S | 6/2007 | Eriksen |
| 7,231,919 | B2 | 6/2007 | Giroux |
| 7,232,897 | B2 | 6/2007 | Hotamisligil et al. |
| 7,234,459 | B2 | 6/2007 | Del Bon |
| 7,234,460 | B2 | 6/2007 | Greenleaf et al. |
| 7,234,464 | B2 | 6/2007 | Goede et al. |
| 7,238,663 | B2 | 7/2007 | DeFelippis et al. |
| 7,246,617 | B1 | 7/2007 | Hammer et al. |
| D548,330 | S | 8/2007 | Cox et al. |
| D548,833 | S | 8/2007 | Young et al. |
| 7,258,118 | B2 | 8/2007 | Goede et al. |
| 7,259,233 | B2 | 8/2007 | Dodd et al. |
| D550,835 | S | 9/2007 | Tanaka et al. |
| 7,270,124 | B2 | 9/2007 | Rasmussen |
| D552,729 | S | 10/2007 | Cox et al. |
| 7,276,534 | B2 | 10/2007 | Milstein |
| 7,278,419 | B2 | 10/2007 | Gonda |
| 7,278,426 | B2 | 10/2007 | Mryman et al. |
| 7,279,457 | B2 | 10/2007 | Pohl et al. |
| 7,284,553 | B2 | 10/2007 | Hochrainer |
| D557,799 | S | 12/2007 | Greenhalgh et al. |
| 7,305,986 | B1 | 12/2007 | Steiner |
| 7,306,787 | B2 | 12/2007 | Tarara et al. |
| D560,793 | S | 1/2008 | Pearl et al. |
| 7,314,859 | B2 | 1/2008 | Green et al. |
| 7,316,748 | B2 | 1/2008 | Li et al. |
| 7,331,340 | B2 | 2/2008 | Barney |
| 7,334,577 | B2 | 2/2008 | Gumaste et al. |
| 7,344,734 | B2 | 3/2008 | Heijerman et al. |
| 7,368,102 | B2 | 5/2008 | Tarara et al. |
| 7,373,938 | B2 | 5/2008 | Nichols et al. |
| 7,377,277 | B2 | 5/2008 | Hickey et al. |
| 7,387,122 | B2 | 6/2008 | Nishibayashi et al. |
| 7,399,528 | B2 | 7/2008 | Caponetti et al. |
| 7,401,713 | B2 | 7/2008 | Ede et al. |
| 7,402,564 | B1 | 7/2008 | Schteingart et al. |
| 7,414,720 | B2 | 8/2008 | Wachtel et al. |
| D577,815 | S | 9/2008 | Gokhale et al. |
| 7,422,013 | B2 | 9/2008 | Burr et al. |
| D579,549 | S | 10/2008 | Birath et al. |
| 7,448,375 | B2 | 11/2008 | Gonda et al. |
| 7,448,379 | B2 | 11/2008 | Yamashita et al. |
| 7,451,761 | B2 | 11/2008 | Hickey et al. |
| 7,453,556 | B2 | 11/2008 | Hochrainer et al. |
| D583,463 | S | 12/2008 | Wood et al. |
| 7,461,653 | B2 | 12/2008 | Oliva |
| 7,462,367 | B2 | 12/2008 | Schmidt et al. |
| 7,464,706 | B2 | 12/2008 | Steiner et al. |
| 7,469,696 | B2 | 12/2008 | Yang et al. |
| 7,500,479 | B2 | 3/2009 | Nichols et al. |
| 7,503,324 | B2 | 3/2009 | Barney et al. |
| 7,504,538 | B2 | 3/2009 | Chang et al. |
| 7,517,874 | B2 | 4/2009 | Beckett et al. |
| 7,520,278 | B2 | 4/2009 | Crowder et al. |
| 7,521,069 | B2 | 4/2009 | Patton et al. |
| 7,533,668 | B1 | 5/2009 | Widerstrom |
| 7,556,798 | B2 | 7/2009 | Edwards et al. |
| 7,559,322 | B2 | 7/2009 | Foley et al. |
| D597,657 | S | 8/2009 | Kinsey et al. |
| 7,584,846 | B2 | 9/2009 | Senter |
| 7,598,222 | B2 | 10/2009 | Prouty, Jr. et al. |
| D604,832 | S | 11/2009 | Smutney |
| D604,833 | S | 11/2009 | Polidoro |
| D605,752 | S | 12/2009 | Polidoro |
| D605,753 | S | 12/2009 | Smutney |
| 7,625,865 | B2 | 12/2009 | Colombo |
| 7,648,960 | B2 | 1/2010 | Steiner et al. |
| D613,849 | S | 4/2010 | Smutney |
| D614,760 | S | 4/2010 | Smutney et al. |
| 7,694,676 | B2 | 4/2010 | Wachtel |
| 7,708,014 | B2 | 5/2010 | Yamashita et al. |
| 7,709,639 | B2 | 5/2010 | Stevenson |
| 7,713,937 | B2 | 5/2010 | Schteingart et al. |
| 7,727,963 | B2 | 6/2010 | Schteingart et al. |
| 7,735,485 | B2 | 6/2010 | Yamashita et al. |
| 7,799,344 | B2 | 9/2010 | Oberg |
| 7,803,404 | B2 | 9/2010 | Hokenson |
| 7,820,676 | B2 | 10/2010 | Leone-Bay et al. |
| 7,842,662 | B2 | 11/2010 | Schteingart et al. |
| D629,505 | S | 12/2010 | Adamo |
| D629,506 | S | 12/2010 | Adamo |
| D629,886 | S | 12/2010 | Adamo |
| D629,887 | S | 12/2010 | Adamo |
| D629,888 | S | 12/2010 | Adamo |
| D635,241 | S | 3/2011 | McLean |
| D635,242 | S | 3/2011 | Adamo |
| D635,243 | S | 3/2011 | Kinsey |
| 7,913,688 | B2 | 3/2011 | Cross |
| D636,868 | S | 4/2011 | Kinsey et al. |
| 7,919,119 | B2 | 4/2011 | Straub et al. |
| 7,943,178 | B2 | 5/2011 | Steiner et al. |
| 7,943,572 | B2 | 5/2011 | Cheatham et al. |
| 7,954,491 | B2 | 6/2011 | Hrkach |
| 7,959,609 | B2 | 6/2011 | Gaydos et al. |
| 8,037,880 | B2 | 10/2011 | Zhu et al. |
| 8,037,881 | B2 | 10/2011 | Pentafragas |
| 8,039,431 | B2 | 10/2011 | Wilson et al. |
| 8,047,203 | B2 | 11/2011 | Young et al. |
| 8,109,267 | B2 | 2/2012 | Villax et al. |
| 8,119,593 | B2 | 2/2012 | Richardson |
| 8,133,514 | B2 | 3/2012 | Milstein |
| 8,146,588 | B2 | 4/2012 | Steiner et al. |
| 8,156,936 | B2 | 4/2012 | Steiner et al. |
| 8,166,970 | B2 | 5/2012 | Poole et al. |
| 8,172,817 | B2 | 5/2012 | Michaels et al. |
| 8,196,576 | B2 | 6/2012 | Kriksunov et al. |

(56) References Cited

U.S. PATENT DOCUMENTS

| | | | |
|---|---|---|---|
| 8,201,555 | B2 | 6/2012 | Chawla |
| 8,202,992 | B2 | 6/2012 | Stevenson |
| 8,215,300 | B2 | 7/2012 | Steiner et al. |
| 8,217,007 | B1 | 7/2012 | Schteingart et al. |
| 8,227,409 | B2 | 7/2012 | Kraft |
| 8,236,766 | B2 | 8/2012 | Schteingart et al. |
| 8,258,095 | B2 | 9/2012 | Boss et al. |
| 8,278,308 | B2 | 10/2012 | Leone-Bay et al. |
| 8,293,869 | B2 | 10/2012 | Bossard |
| 8,314,106 | B2 | 11/2012 | Kraft |
| 8,372,804 | B2 | 2/2013 | Richardson |
| 8,377,869 | B2 | 2/2013 | Richardson |
| 8,389,470 | B2 | 3/2013 | Steiner |
| 8,394,414 | B2 | 3/2013 | Steiner et al. |
| 8,408,200 | B2 | 4/2013 | Clark et al. |
| 8,420,604 | B2 | 4/2013 | Hokenson |
| 8,424,518 | B2 | 4/2013 | Smutney |
| 8,485,180 | B2 | 7/2013 | Smutney |
| 8,486,894 | B2 | 7/2013 | Schteingart et al. |
| 8,499,757 | B2 | 8/2013 | Smutney |
| 8,512,932 | B2 | 8/2013 | Wilson et al. |
| 8,522,775 | B2 | 9/2013 | Malhotra et al. |
| 8,536,131 | B2 | 9/2013 | Schteingart et al. |
| 8,538,707 | B2 | 9/2013 | Adamo |
| 8,539,946 | B2 | 9/2013 | Esteve et al. |
| 8,551,528 | B2 | 10/2013 | Grant et al. |
| 8,636,001 | B2 | 1/2014 | Smutney |
| 8,671,937 | B2 | 3/2014 | Steiner |
| 8,677,992 | B2 | 3/2014 | Villax |
| 8,763,606 | B2 | 7/2014 | Mosier et al. |
| 8,820,324 | B2 | 9/2014 | Smith et al. |
| 8,925,726 | B2 | 1/2015 | Bergey |
| 9,138,407 | B2 | 9/2015 | Caponetti et al. |
| 2002/0052381 | A1 | 5/2002 | Bar-Or et al. |
| 2002/0053344 | A1 | 5/2002 | Davies et al. |
| 2002/0053347 | A1 | 5/2002 | Ziaee |
| 2002/0065239 | A1 | 5/2002 | Caplan et al. |
| 2002/0088462 | A1 | 7/2002 | Genova et al. |
| 2002/0101590 | A1 | 8/2002 | Shimaoka |
| 2002/0144680 | A1 | 10/2002 | Nilsson et al. |
| 2002/0161001 | A1 | 10/2002 | Kanstrup et al. |
| 2003/0000524 | A1 | 1/2003 | Anderson et al. |
| 2003/0010794 | A1 | 1/2003 | Herdtle et al. |
| 2003/0013641 | A1 | 1/2003 | Steiner et al. |
| 2003/0017211 | A1 | 1/2003 | Steiner |
| 2003/0053960 | A1 | 3/2003 | Heijerman et al. |
| 2003/0064097 | A1 | 4/2003 | Patel et al. |
| 2003/0068378 | A1 | 4/2003 | Chen et al. |
| 2003/0099636 | A1 | 5/2003 | Epshtein et al. |
| 2003/0136405 | A1 | 7/2003 | Goede et al. |
| 2003/0194420 | A1 | 10/2003 | Holl et al. |
| 2003/0235538 | A1 | 12/2003 | Zirenberg |
| 2004/0024180 | A1 | 2/2004 | Drauz |
| 2004/0025875 | A1 | 2/2004 | Reber et al. |
| 2004/0034014 | A1 | 2/2004 | Kanstrup et al. |
| 2004/0038865 | A1 | 2/2004 | Gelber et al. |
| 2004/0053819 | A1 | 3/2004 | Dodd et al. |
| 2004/0062722 | A1 | 4/2004 | Gonda et al. |
| 2004/0077528 | A1 | 4/2004 | Steiner et al. |
| 2004/0096403 | A1 | 5/2004 | Steiner |
| 2004/0107963 | A1 | 6/2004 | Finlay et al. |
| 2004/0121964 | A1 | 6/2004 | Madar et al. |
| 2004/0138099 | A1 | 7/2004 | Draeger |
| 2004/0151059 | A1 | 8/2004 | Robert, II et al. |
| 2004/0151774 | A1 | 8/2004 | Pauletti et al. |
| 2004/0157928 | A1 | 8/2004 | Kim et al. |
| 2004/0163648 | A1 | 8/2004 | Burton |
| 2004/0182387 | A1 | 9/2004 | Steiner et al. |
| 2004/0187869 | A1 | 9/2004 | Bjorndal et al. |
| 2004/0204439 | A1 | 10/2004 | Staniforth et al. |
| 2004/0204440 | A1 | 10/2004 | Staniforth et al. |
| 2004/0211419 | A1 | 10/2004 | Eason et al. |
| 2004/0234615 | A1 | 11/2004 | Sabetsky |
| 2004/0234616 | A1 | 11/2004 | Sabetsky |
| 2004/0247628 | A1 | 12/2004 | Lintz et al. |
| 2004/0250812 | A1 | 12/2004 | Davies et al. |
| 2005/0000518 | A1 | 1/2005 | Dunkley et al. |
| 2005/0039743 | A1 | 2/2005 | Taylor |
| 2005/0043228 | A1 | 2/2005 | DeFelippis et al. |
| 2005/0043247 | A1 | 2/2005 | Trunk et al. |
| 2005/0056281 | A1 | 3/2005 | Snow |
| 2005/0070469 | A1 | 3/2005 | Bloom |
| 2005/0080000 | A1 | 4/2005 | Thurow et al. |
| 2005/0119604 | A1 | 6/2005 | Bonney et al. |
| 2005/0147581 | A1 | 7/2005 | Zamiri et al. |
| 2005/0153874 | A1 | 7/2005 | Cheatham et al. |
| 2005/0156601 | A1 | 7/2005 | Dupuis et al. |
| 2005/0183723 | A1 | 8/2005 | Pinon et al. |
| 2005/0187749 | A1 | 8/2005 | Singley |
| 2005/0214251 | A1 | 9/2005 | Pohl et al. |
| 2005/0252508 | A1 | 11/2005 | Koerner |
| 2005/0265927 | A1 | 12/2005 | Lee |
| 2005/0274378 | A1 | 12/2005 | Bonney et al. |
| 2006/0000469 | A1 | 1/2006 | Tseng |
| 2006/0040953 | A1 | 2/2006 | Leone-Bay et al. |
| 2006/0041133 | A1 | 2/2006 | Stevenson et al. |
| 2006/0099269 | A1 | 5/2006 | Cheatham et al. |
| 2006/0120969 | A1 | 6/2006 | Nilsson et al. |
| 2006/0153778 | A1 | 7/2006 | Gelber et al. |
| 2006/0160722 | A1 | 7/2006 | Green et al. |
| 2006/0165756 | A1 | 7/2006 | Catani et al. |
| 2006/0239933 | A1 | 10/2006 | Nilsson et al. |
| 2006/0239934 | A1 | 10/2006 | Cheatham et al. |
| 2006/0243275 | A1 | 11/2006 | Ruckdeschel et al. |
| 2006/0249419 | A1 | 11/2006 | Taylor et al. |
| 2006/0260777 | A1 | 11/2006 | Rashba-Step et al. |
| 2006/0283758 | A1 | 12/2006 | Pasbrig |
| 2007/0020191 | A1 | 1/2007 | Boss et al. |
| 2007/0027063 | A1 | 2/2007 | Boss et al. |
| 2007/0044793 | A1 | 3/2007 | Kleinstreuer et al. |
| 2007/0059373 | A1 | 3/2007 | Oberg |
| 2007/0059374 | A1 | 3/2007 | Hokenson et al. |
| 2007/0074989 | A1 | 4/2007 | Merboth et al. |
| 2007/0086952 | A1 | 4/2007 | Steiner |
| 2007/0099454 | A1 | 5/2007 | Gordon |
| 2007/0125375 | A1 | 6/2007 | Finlay et al. |
| 2007/0151562 | A1 | 7/2007 | Jones |
| 2007/0191462 | A1 | 8/2007 | Hettiarachchi |
| 2007/0196503 | A1 | 8/2007 | Wilson et al. |
| 2007/0207958 | A1 | 9/2007 | Bridon et al. |
| 2007/0225587 | A1 | 9/2007 | Burnell et al. |
| 2007/0235029 | A1 | 10/2007 | Zhu et al. |
| 2007/0240708 | A1 | 10/2007 | Schuckmann |
| 2007/0272763 | A1 | 11/2007 | Dunne et al. |
| 2007/0295332 | A1 | 12/2007 | Ziegler |
| 2008/0015457 | A1 | 1/2008 | Silva |
| 2008/0047550 | A2 | 2/2008 | Steiner et al. |
| 2008/0066739 | A1 | 3/2008 | LeMahieu et al. |
| 2008/0108554 | A1 | 5/2008 | Jackson et al. |
| 2008/0115785 | A1 | 5/2008 | Eason et al. |
| 2008/0127970 | A1 | 6/2008 | Steiner et al. |
| 2008/0127974 | A1 | 6/2008 | Lastow |
| 2008/0129791 | A1 | 6/2008 | Furukawa et al. |
| 2008/0168987 | A1 | 7/2008 | Denny et al. |
| 2008/0190424 | A1 | 8/2008 | Lucking et al. |
| 2008/0197044 | A1 | 8/2008 | Hickey et al. |
| 2008/0216824 | A1 | 9/2008 | Ooida |
| 2008/0217199 | A1 | 9/2008 | Burress et al. |
| 2008/0255468 | A1 | 10/2008 | Derchak et al. |
| 2008/0260838 | A1 | 10/2008 | Hokenson et al. |
| 2008/0260840 | A1 | 10/2008 | Alessi |
| 2008/0295833 | A1 | 12/2008 | Rohrschneider et al. |
| 2008/0314384 | A1 | 12/2008 | Harris et al. |
| 2008/0319333 | A1 | 12/2008 | Gavish et al. |
| 2009/0025720 | A1 | 1/2009 | Chen |
| 2009/0068274 | A1 | 3/2009 | Edwards et al. |
| 2009/0084379 | A1 | 4/2009 | Goeckner et al. |
| 2009/0084380 | A1 | 4/2009 | Gieschen et al. |
| 2009/0149727 | A1 | 6/2009 | Truitt et al. |
| 2009/0151720 | A1 | 6/2009 | Inoue et al. |
| 2009/0178676 | A1 | 7/2009 | Villax et al. |
| 2009/0205657 | A1 | 8/2009 | Barney et al. |
| 2009/0209502 | A1 | 8/2009 | Haeberlin et al. |
| 2009/0232891 | A1 | 9/2009 | Gelber et al. |

(56) References Cited

U.S. PATENT DOCUMENTS

| | | | | |
|---|---|---|---|---|
| 2009/0241949 | A1 | 10/2009 | Smutney | |
| 2009/0250058 | A1 | 10/2009 | Lastow | |
| 2009/0258818 | A1 | 10/2009 | Surolia et al. | |
| 2009/0314292 | A1 | 12/2009 | Overfield | |
| 2009/0320837 | A1 | 12/2009 | Smith et al. | |
| 2010/0012120 | A1 | 1/2010 | Herder | |
| 2010/0086609 | A1 | 4/2010 | Steiner et al. | |
| 2010/0113363 | A1 | 5/2010 | Holst et al. | |
| 2010/0163042 | A1 | 7/2010 | Bhowmick et al. | |
| 2010/0180894 | A1 | 7/2010 | Jones et al. | |
| 2010/0181255 | A1 | 7/2010 | Riebensahm et al. | |
| 2010/0190701 | A1 | 7/2010 | Day et al. | |
| 2010/0193380 | A1 | 8/2010 | Sullivan et al. | |
| 2010/0197565 | A1 | 8/2010 | Smutney et al. | |
| 2010/0212667 | A1 | 8/2010 | Smith et al. | |
| 2010/0235116 | A1 | 9/2010 | Adamo et al. | |
| 2010/0238457 | A1 | 9/2010 | Adamo et al. | |
| 2010/0278924 | A1 | 11/2010 | Oberg | |
| 2010/0326438 | A1 | 12/2010 | Dunne | |
| 2011/0000482 | A1 | 1/2011 | Gumaste et al. | |
| 2011/0003004 | A1 | 1/2011 | Hokenson | |
| 2011/0011394 | A1 | 1/2011 | Edwards et al. | |
| 2011/0083667 | A1 | 4/2011 | Briant | |
| 2011/0158935 | A1 | 6/2011 | Kraft | |
| 2011/0183901 | A1 | 7/2011 | Cheatham | |
| 2012/0014999 | A1 | 1/2012 | Grant et al. | |
| 2012/0040899 | A1 | 2/2012 | Costello | |
| 2012/0071510 | A1 * | 3/2012 | Leone-Bay et al. | .......... 514/323 |
| 2012/0094905 | A1 | 4/2012 | Costello | |
| 2012/0115777 | A1 | 5/2012 | Richardson | |
| 2012/0122775 | A1 | 5/2012 | Boss et al. | |
| 2012/0160241 | A1 | 6/2012 | Oliva | |
| 2012/0164186 | A1 | 6/2012 | Grant et al. | |
| 2012/0178935 | A1 | 7/2012 | Stevenson | |
| 2012/0192865 | A1 | 8/2012 | Steiner et al. | |
| 2012/0207913 | A1 | 8/2012 | Smyth | |
| 2012/0240929 | A1 | 9/2012 | Steiner et al. | |
| 2012/0247235 | A1 | 10/2012 | Adamo et al. | |
| 2012/0247465 | A1 | 10/2012 | Wachtel | |
| 2012/0328676 | A1 | 12/2012 | Leone-Bay et al. | |
| 2013/0012710 | A1 | 1/2013 | Freeman et al. | |
| 2013/0053309 | A1 | 2/2013 | Kraft | |
| 2013/0104887 | A1 | 5/2013 | Smutney et al. | |
| 2013/0125886 | A1 | 5/2013 | Richardson et al. | |
| 2013/0143801 | A1 | 6/2013 | Steiner et al. | |
| 2013/0189365 | A1 | 7/2013 | Hokenson | |
| 2013/0199527 | A1 | 8/2013 | Smutney et al. | |
| 2013/0289278 | A1 | 10/2013 | Kraft | |
| 2013/0291866 | A1 | 11/2013 | Smutney | |
| 2013/0291867 | A1 | 11/2013 | Smutney | |
| 2013/0303445 | A1 | 11/2013 | Wilson et al. | |
| 2013/0338065 | A1 | 12/2013 | Smutney | |
| 2014/0007873 | A1 | 1/2014 | Smutney | |
| 2014/0014106 | A1 | 1/2014 | Smutney | |
| 2014/0083421 | A1 | 3/2014 | Smutney | |
| 2014/0096771 | A1 | 4/2014 | Remmelgas et al. | |

FOREIGN PATENT DOCUMENTS

| | | | |
|---|---|---|---|
| DE | 2840442 | C2 | 2/1982 |
| DE | 3639836 | A | 6/1988 |
| DE | 19519840 | A1 | 12/1996 |
| EP | 069715 | | 1/1983 |
| EP | 122036 | | 10/1984 |
| EP | 143524 | | 6/1985 |
| EP | 180543 | | 5/1986 |
| EP | 220958 | | 5/1987 |
| EP | 237507 | | 8/1987 |
| EP | 257915 | | 2/1988 |
| EP | 308637 | A1 | 3/1989 |
| EP | 360340 | | 3/1990 |
| EP | 364235 | | 4/1990 |
| EP | 387222 | A | 9/1990 |
| EP | 388621 | A | 9/1990 |
| EP | 606486 | | 12/1993 |
| EP | 581473 | A1 | 2/1994 |
| EP | 655237 | | 5/1995 |
| EP | 666085 | A1 | 8/1995 |
| EP | 748213 | | 12/1996 |
| EP | 844007 | | 12/1998 |
| EP | 1060741 | A1 | 12/2000 |
| EP | 1114644 | | 7/2001 |
| EP | 640354 | B1 | 12/2001 |
| EP | 1364967 | | 11/2003 |
| EP | 825885 | B1 | 3/2004 |
| EP | 96911738 | | 6/2004 |
| EP | 1598066 | | 11/2005 |
| EP | 833652 | B1 | 2/2008 |
| EP | 1923087 | A2 | 5/2008 |
| EP | 2060268 | A1 | 5/2009 |
| EP | 2314298 | A1 | 4/2011 |
| GB | 4754400 | A | 11/1937 |
| GB | 716815 | | 10/1954 |
| GB | 2072536 | A | 10/1981 |
| GB | 2148841 | A | 6/1985 |
| GB | 2240337 | | 7/1991 |
| GB | 2253200 | A | 9/1992 |
| GB | 2262452 | | 6/1993 |
| GB | 2398065 | A | 8/2004 |
| JP | 63-020301 | | 1/1988 |
| JP | 2115154 | A | 4/1990 |
| JP | 2-149545 | | 2/1992 |
| JP | 09-208485 | | 8/1997 |
| JP | 10234827 | A | 9/1998 |
| JP | 2002322294 | | 11/2002 |
| JP | 2003-503420 | | 1/2003 |
| JP | 2004-121061 | | 4/2004 |
| WO | 90/13285 | | 11/1990 |
| WO | 91/04011 | | 4/1991 |
| WO | 91/06287 | | 5/1991 |
| WO | 91/16038 | | 10/1991 |
| WO | 91/16882 | | 11/1991 |
| WO | 91/19524 | | 12/1991 |
| WO | 92/04069 | | 3/1992 |
| WO | 92/08509 | | 5/1992 |
| WO | 93/02712 | | 2/1993 |
| WO | 93/14110 | | 7/1993 |
| WO | 93/17728 | | 9/1993 |
| WO | 93/18754 | A1 | 9/1993 |
| WO | 94/00291 | | 1/1994 |
| WO | 94/08552 | | 4/1994 |
| WO | 94/08599 | | 4/1994 |
| WO | 94/19041 | | 9/1994 |
| WO | 94/23702 | | 10/1994 |
| WO | 95/00127 | A1 | 1/1995 |
| WO | 95/05208 | | 2/1995 |
| WO | 95/11666 | | 5/1995 |
| WO | 95/24183 | A1 | 9/1995 |
| WO | 95/31979 | | 11/1995 |
| WO | 95/34294 | | 12/1995 |
| WO | 96/01105 | | 1/1996 |
| WO | 96/05810 | | 2/1996 |
| WO | 96/13250 | | 5/1996 |
| WO | 96/22802 | A | 8/1996 |
| WO | 96/27386 | A1 | 9/1996 |
| WO | 96/36314 | | 11/1996 |
| WO | 96/40206 | A1 | 12/1996 |
| WO | 97/01365 | | 1/1997 |
| WO | 97/04747 | | 2/1997 |
| WO | 97/30743 | | 8/1997 |
| WO | 97/46206 | | 12/1997 |
| WO | 97/49386 | | 12/1997 |
| WO | 98/26827 | A1 | 6/1998 |
| WO | 98/39043 | | 9/1998 |
| WO | 98/42155 | A2 | 9/1998 |
| WO | 98/43615 | | 10/1998 |
| WO | 99/14239 | A1 | 3/1999 |
| WO | 99/18939 | A1 | 4/1999 |
| WO | 99/32510 | A1 | 7/1999 |
| WO | 99/33862 | | 7/1999 |
| WO | 99/52506 | | 10/1999 |
| WO | 00/12116 | | 3/2000 |
| WO | 00/71154 | | 11/2000 |

(56) References Cited

FOREIGN PATENT DOCUMENTS

| | | | |
|---|---|---|---|
| WO | 01/00654 | | 1/2001 |
| WO | 01/81321 | A | 1/2001 |
| WO | 01/07107 | | 2/2001 |
| WO | 01/49274 | A2 | 7/2001 |
| WO | 01/51071 | | 7/2001 |
| WO | 01/66064 | | 9/2001 |
| WO | 01/68169 | | 9/2001 |
| WO | 02/11676 | | 2/2002 |
| WO | 02/12201 | A1 | 2/2002 |
| WO | 02/47659 | A2 | 6/2002 |
| WO | 02/058735 | | 8/2002 |
| WO | 02/059574 | A1 | 8/2002 |
| WO | 02/067995 | A1 | 9/2002 |
| WO | 02/085281 | | 10/2002 |
| WO | 02/098348 | | 12/2002 |
| WO | 02/102444 | | 12/2002 |
| WO | 03/000202 | | 1/2003 |
| WO | 2003/022304 | A1 | 3/2003 |
| WO | 03/005547 | | 7/2003 |
| WO | 03/057170 | | 7/2003 |
| WO | 03/086346 | | 10/2003 |
| WO | 03/094951 | | 11/2003 |
| WO | 2004/012672 | | 2/2004 |
| WO | 2004/012720 | | 2/2004 |
| WO | 2004/035121 | | 2/2004 |
| WO | 2004/033010 | | 4/2004 |
| WO | 2004/041338 | | 5/2004 |
| WO | 2004/050152 | | 6/2004 |
| WO | 2004/054647 | A1 | 7/2004 |
| WO | 2004/056314 | | 7/2004 |
| WO | 2004/060458 | | 7/2004 |
| WO | 2004/064862 | | 8/2004 |
| WO | 2004/075919 | | 9/2004 |
| WO | 2004/080401 | | 9/2004 |
| WO | 2004/080482 | | 9/2004 |
| WO | 2004/103304 | A2 | 12/2004 |
| WO | 2005/020964 | | 3/2005 |
| WO | 2005/023348 | A | 3/2005 |
| WO | 2005/028699 | A1 | 3/2005 |
| WO | 2005/067964 | | 7/2005 |
| WO | 2005/081977 | A2 | 9/2005 |
| WO | 2005/089722 | | 9/2005 |
| WO | 2005/089843 | | 9/2005 |
| WO | 2005/102428 | A1 | 11/2005 |
| WO | 2005/102429 | | 11/2005 |
| WO | 2005/113042 | A1 | 12/2005 |
| WO | 2005/113043 | A1 | 12/2005 |
| WO | 2005/120616 | | 12/2005 |
| WO | 2006/010248 | | 2/2006 |
| WO | 2006/023849 | | 3/2006 |
| WO | 2006/023943 | | 3/2006 |
| WO | 2006/023944 | | 3/2006 |
| WO | 2006/037636 | | 4/2006 |
| WO | 2006/059939 | | 6/2006 |
| WO | 2006/061637 | A2 | 6/2006 |
| WO | 2006/086107 | A2 | 8/2006 |
| WO | 2006/090149 | | 8/2006 |
| WO | 2006/105501 | | 10/2006 |
| WO | 2007/019229 | | 2/2007 |
| WO | 2007/024953 | A1 | 3/2007 |
| WO | 2007/030706 | | 3/2007 |
| WO | 2007/033316 | | 3/2007 |
| WO | 2007/042822 | | 4/2007 |
| WO | 2007/068896 | | 6/2007 |
| WO | 2007/075534 | A2 | 7/2007 |
| WO | 2007/093310 | | 8/2007 |
| WO | 2007/098500 | | 8/2007 |
| WO | 2007/100535 | | 9/2007 |
| WO | 2007/118342 | | 10/2007 |
| WO | 2007/121411 | | 10/2007 |
| WO | 2007/132217 | | 11/2007 |
| WO | 2007/144607 | | 12/2007 |
| WO | 2007/144614 | | 12/2007 |
| WO | 2008/001744 | | 1/2008 |
| WO | 2008/008021 | | 1/2008 |
| WO | 2008/014613 | A1 | 2/2008 |
| WO | 2008/020217 | | 2/2008 |
| WO | 2008/060484 | A2 | 5/2008 |
| WO | 2008/092864 | | 8/2008 |
| WO | 2008/110809 | | 9/2008 |
| WO | 2009/005546 | A1 | 1/2009 |
| WO | 2009/008001 | A2 | 1/2009 |
| WO | 2009/055030 | | 4/2009 |
| WO | 2009/055740 | | 4/2009 |
| WO | 2009/055742 | | 4/2009 |
| WO | 2009/095684 | A1 | 8/2009 |
| WO | 2009/047281 | | 12/2009 |
| WO | 2010/080964 | | 7/2010 |
| WO | 2010/102148 | | 9/2010 |
| WO | 2010/105094 | A1 | 9/2010 |
| WO | 2010/125103 | A1 | 11/2010 |
| WO | 2010/144789 | | 12/2010 |
| WO | 2011/163272 | | 12/2011 |
| WO | 2012/135765 | | 10/2012 |
| WO | 2013/063160 | | 5/2013 |

OTHER PUBLICATIONS

Alabraba et al. Diabetes Technology & Therapeutics. Jul. 2009, 11(7): 427-430.

Alcohols limited. Alcohol speciality solvents—Go green! Jul. 24, 2010. Available from: <http://webarchive.org/web/20100724193725/http://www.alcohols.co.uk/speciality_solvents.php>.

Aljada et al. "Insulin inhibits the pro-inflammatroy transcription factor early growth response gene-1 (Egr)-1 expression in mononuclear cells (MNC) and reduces plasma tissue factor (TF) and plasminogen activator inhibitor-1 (PAI-1) concentrations." The Journal of Clinical Endocrinology and Metabolism, vol. 87, No. 3, p. 1419-1422, 2002.

Al-Showair et al., Can all patients with COPD use the correct inhalation flow with all inhalers and does training help? Respiratory Medicine, vol. 101, No. 11, p. 2395-2401 (2007).

American Diabetes Association, "Standards of medical care in diabetes—2009", Diabetes Care, Jan. 2009, 32 Suppl 1: S13-61.

Amin N, Boss AH, Petrucci R, et al. Pulmonary functions (over 2 years) in diabetic subjects treated with AFRESA® or usual antidiabetic treatment ADA 2009; Poster 570.

Amin N, et al. Long-term sustained safety and efficacy of continued use of Technosphere insulin in subjects with type 2 diabetes. Abstract—Oral Presentation 215, 48th EASD Annual Meeting, Sep. 29-Oct. 2, 2009, Vienna Austria.

Amin N, Marino MT, Cassidy JP, et al. Acute pulmonary effects of Technosphere® insulin inhalation powder administered using a Gen2B inhaler compared to MedTone® C inhaler. Diabetes Technology Meeting 2010; Poster 290.

Amin N, Phillips M, Boss AH, et al. Pulmonary functions (over 2 years) in diabetic patients treated with Technosphere® insulin (TI) or usual antidiabetic treatment. Third International Conference on Advanced Technologies and Treatments for Diabetes. 2010; Poster 290.

Angelo et al., Technosphere Insulin: Defining the Role of Technosphere Particles at the Celluar Level. J. Diabetes Sci. Technol., vol. 3, Issue 3, pp. 545-554 (2009).

Angelo et al. Technosphere® insulin inhalation powder: Defining the mechanism of action. ADA 2008; 57: Poster 428-P.

Antosiewiez et al., Prediction of pH-dependent properties of proteins. J Mol. Biol., 238:415-436 (1994).

Arakawa et al., Preferential interactions determine protein solubility in three-component solutions: the MgCl2 system. Biochemistry, 29:1914-1923 (1990).

Ashwell et al. "Twice-daily compared with once-daily insulin glargine in people with Type 1 diabetes using meal-time insulin aspart." 2006 Diabetes UK, Diabetic Medicine, 23, 879-886.

Ashwell et al., "Optimal timing of injection of once-daily insulin gargine in people with Type 1 diabetes using insulin lispro at meal-times" 2005 Diabetes UK, Diabetic Medicine, 23, 46-52.

Atherton, F. et al. "Synthesis of 2(R)-A3(S)-Acylamino-2-OXO-1-Azetidinyloxy U-Acetic Acids." Tetrahedron, vol. 40, No. 6, Jan. 1, 1984, pp. 1039-1046.

(56) References Cited

OTHER PUBLICATIONS

Avandia Product Insert, Oct. 2008.
Baggio et al. "A recombinant human glucagon-like peptide (GLP)-1-albumin protein (Albugon) mimics peptidergic activation of GLP-1 receptor-dependent pathways coupled with satiety, gastrointestinal motility, and glucose homeostatsis." Diabetes 53:2492, 2004.
Baggio et al. "Glucagon-like peptide-1, but not glucose-dependent insulinotropic peptide, regulates fasting glycemia and noneneteral glucose clearance in mice." Endocrinology 141:3703, 2000.
Baggio et al. "Harnessing the therapeutic potential of glucagon-like peptide-1." Treat Endocrinol 1:117, 2002.
Balkan B et al. "Portal GLP-1 administration in rats augments the insulin response to glucose via neuronal mechanisms." Am J. Physiol Regulatory Integrative Comp Physiol 279:R1449, 2000.
Barnett AH et al. "An open, randomized, parallel-group study to compare the efficacy and safety profile of inhaled human insulin (Exubera) with glibenclamide as adjunctive therapy in patients with Type 2 diabetes poorly controlled on metformin." Diabetes Care 29(8):1818-1825, 2006.
Barnett et al., An open, randomized, parallel-group study to compare the efficacy and safety profile of inhaled human insulin (Exubera) with metformin as adjunctive therapy in patients with type 2 diabetes poorly controlled on a sulfonylurea. Diabetes Care, 29(6): 1282-1287 (2006).
Barragan et al. "Changes in arterial blood pressure and heart rate induced by glucagon-like peptide-1-(7-36) amide in rats." Am J. Physiol 266 (Endocrinol Metab 29):E459, 1994.
Basu A et al. "Effects of a change in the pattern of insulin delivery on carbohydrate tolerance in diabetic and nondiabetic humans in the presence of differing degrees of insulin resistance." J Clin Invest 97:2351-2361, 1996.
Bauer et al., "Assessment o beta-adrenergic receptor blockade after isamoitane, a 5-HT1-receptor active compound, in healthy volunteer", Clin. Pharmacol Ther 53:76-83 (1993).
Bauer et al., "Pharmacodynamic effects of inhaled dry powder formulations of fenterol and colforsin in asthma", Clin Pharmacol Ther 53:76-83, 1993.
Baughman R, Cassidy J, Amin N, et al. A phase I, open-label study of the effect of albuterol or fluticasone on the pharmacokinetics of inhaled Technosphere® insulin inhalation powder in healthy subjects. ADA 2010; Poster 528.
Baughman R, Cassidy J, Levy B, et al. Technosphere® insulin inhalation powder pharmacokinetics unchanged in subjects who smoke. Diabetes 2008; 57: A128.
Baughman R, Haworth P, Litwin J, et al. No cardiac effects found with therapeutic and suprtherapeutic doses of Technosphere® inhalation powder: results from a thorough QTc clinical study. ADA 2011. Poster 933-P.
Baughman, RA, Evans, SH, Boss, AH, et al. Technosphere insulin does not affect pulmonary function in a 6 month study of patients with type 2 diabetes. Diabetologia 2006;49:177-118.
Bayés M et al. "Gateways to clinical trials" Methods Find Exp Clin Pharmacol 24:431-455, 2002.
Beers et al., Section 2—Chapter 13—Diabetes Mellitus, The Merck Manual of Diagnosis and Therapy, Merck Research Laboratories, pp. 165-177 (1999).
Behme et al. "Glucagon-like peptide-1 improved glycemic control in type 1 diabetes." BMC Endocrine Disorders 3:3, 2003.
Bellary et al. "Inhaled insulin:new technology, new possibilities." Int J Clin Pract 60:728, 2006.
Belmin J et al. "Novel drug delivery systems for insulin. Clinical potential for use in the elderly." Drugs Aging 20:303-12, 2003.
Benita, Charaterization of Drug-Loaded Poly(d,l-lactide) Microspheres. J. Pharm. Sci., 73: 1721-1724 (1984).
Benito E et al. "Glucagon-like peptide-1-(7-36) amide increases pulmonary surfactant secretion through a cyclic adenosine 3',5'-monophosphate-dependent protein kinase mechanism in rat type II pneumocytes." Endocrinology 139:2363, 1998.
Bensch et al., Absorption of intact protein molecules across the pulmonary air-tissue barrier, Science 156: 1204-1206 (1967).
Berge et al., "Pharmaceutical Salts", J. Pharmaceutical Sciences, Review Article, 66(1):1-19 (1977).
Bergenstal R, Kapsner P, Rendell M, et al., Comparative efficacy and safety of AFRESA® and a rapid-acting analog both given with glargine in subjects with T1 DM in a 52-week study ADA 2009; Poster 479.
Bergeron et al. "Macromolecular Self-Assembly of Diketopiperazine Tetrapeptides." J. Am. Chem. Soc. 116, 8479-8484, 1994.
Heine "Unlocking the opportunity of tight glycaemic control. Promise ahead: the role of inhaled insulin in clinical practice." Diabetes, Obesity and Metabolism 7:S19, 2005.
Heinemann "Variability of Insulin Absorption and Insulin Action." Diabetes Technology & Therapeutics, vol. 4, No. 5, pp. 673-682. 2002.
Heinemann et al. "Current status of the development of inhaled insulin." Br. J. Diabetes Vasc. Dis. 4:295-301, 2004.
Heinemann L et al. "Time-action profile of inhaled insulin." Diabetic Med 14:63-72, 1997.
Heinemann, L. "Intra-individual Variability of the Metabolic Effect of Inhales Insulin Together with an Absorption Enhancer", Diabetes Care, vol. 23, No. 9, Sep. 2000, pp. 1343-1347.
Heise et al. "The effect of insulin antibodies on the metabolic action of inhaled and subcutaneous insulin." Diabetes Care 28:2161, 2005.
Herbst et al., Insulin Strategies for Primary Care Providers. Clinical Diabetes, vol. 20, No. 1, pp. 11-17 (2002).
Heubner et al. "On inhalation of insulin" Klinische Wochenschrift 16:2342, 1924. Both original and translated documents included.
Heyder "Particle Transport onto Human Airway Surfaces", Eur. J. Respir. Dis, Suppl. 119, 29-50 (1982).
Heyder, "Alveolar deposition of inhaled particles in humans", Am. Ind. Hyg. Assoc. J. 43(11): 864-866 (1982).
Hirsch IB "Insulin analogues." N Engl J Med 352:174-83, 2005.
Hirsch, "Type 1 Diabetes Mellitus and the Use of Flexible Insulin Regimens" American Family Phyician, Nov. 15, 1999, p. 1-16.
Hirshberg B et al. "Islet transplantation: where do we stand now?" Diabetes Metab Res Rev 19:175-8, 2003.
Hite et al. "Exhuberance over Exubera." Clin Diabetes 24(3):110-114, 2006.
Hoet et al., Review: Nanoparticles—known and unknown health risks. Journal of Nanobiotechnology, vol. 2, No. 12, (15 pages) (2004).
Hollander et al. "Efficacy and Safety of Inhaled Insulin (Exubera) Compared with Subcutaneous Insulin Therapy in Patients with Type 2 Diabetes." Diabetes Care, vol. 27, No. 10, Oct. 2004, p. 2356-2362.
Holst "Therapy of type 2 diabetes mellitus based on the actions of glucagon-like peptide-1." Diabetes Metab Res Rev 18:430, 2002.
Holst et al. "On the effects of glucagon-like peptide-1 on blood glucose regulation in normal and diabetic subjects." Ann N Y Acad Sci. Dec. 26, 1996;805:729-36.
Howard C, Ren H, Rossiter A, et al. Reduced incidence and frequency of hypoglycemia in an integrated analysis of pooled data from clinical trials of subjects with type 1 diabetes using prandial inhaled Technosphere® insulin Diabetologia 2009; 52 (suppl 1).
Howard CP, Gnudi L, Lorber D, et al. Prandial inhaled Technosphere® insulin plus insulin glargine vs. biaspart 70/30 insulin in type 2 diabetes inadequately controlled with/without oral agents. Third International Conference on Advanced Technologies and Treatments for Diabetes. 2010; Poster 300.
Howard CP, Lorber D, Ren H, et al. Reduced incidence and frequency of hypoglycemia in pooled data from trials of type 2 diabetics using prandial inhaled Technosphere® insulin. Third International Conference on Advanced Technologies and Treatments for Diabetes 2010; Poster 304.
Howard CP, Petrucci R,Amin N, et al. Pulmonary function test remain similar in patients who received Technosphere® insulin and in patients currently receiving standard antidiabetic therapy. AACE 2010; Poster 267.
Howard CP, Ren H, Rossiter A, Boss AH. Reduced incidence and frequency of hypoglycemia in pooled data from trials of type 1 diabetics using prandial inhaled Technosphere® insulin. Third International Conference on Advanced Technologies and Treatments for Diabetes. 2010; Poster 302.

(56) References Cited

OTHER PUBLICATIONS

Howard CP, Ren H, Rossiter A, et al. Reduced incidence and frequency of hypoglycemia in an integrated analysis of pooled data from clinical trials of subjects with type 1 diabetes using prandial inhaled Technosphere® insulin. AACE 2010; Poster 269.

Howard CP, Rubin RR, Peyrot. M. Patient reported outcomes in adults with type 2 diabetes using mealtime AFRESA® (inhaled Technosphere® insulin) and basal insulin versus premixed insulin ADA 2009; Poster 551.

http://www.bilcaresolutions.com/en/products/pharma-packaging-innovations-pvc-aclar-films <URL:http://web.archive.org/web/20110127102552/http://www.bilcaresolutions.com/en/products/pharma-packaging-innovations-pvc-aclar-films> published on Jan. 27, 2011 as per "Wayback Engine".

http://www.pmpnews.com/article/blister-packaging-materials (May 26, 2009).

Huda et al. "Gut peptides and the regulation of appetite." Obesity Reviews 7:163, 2006.

Hui et al., The short half-life of glucagon-like peptide-1 in plasma does not reflect its long-lasting beneficial effects European Journal of Endocrinology, 146: 863-869 (2002).

Hussain et al. "State of insulin self-association does not affects its absorption from the pulmonary route." Eur. J. Pharm. Sciences 25:289-298, 2005.

Ikeda, Kuniki et al. "Peptide Antibiotics. XXVI. Syntheses of Cyclodipeptides Containing N. delta.-p-aminobenzenesulfonyl Ornithine Residue." Chemical & Pharmaceutical Bulletin, 20(9), 1849-55, 1972.

Imeryuz et al. "Glucagon-like peptide-1 inhibits gastric emptying via vagal afferent-mediated central mechanisms."Am J Physiol 273 (Gastrointest Liver Physiol 36):G920, 1997.

Insulin inhalation NN 1998, Drugs R & D, 2004, pp. 46-49, Adis Data Information BV.

Insulin is a natural product from http://www.levemir.com/startingoninsulin/whatisinulin.aspx, pp. 1-3.

International Search Report for PCT International Application No. PCT/US2010/055323 filed on Nov. 3, 2010.

Written Opinion mailed on Jul. 1, 2013 for International Application No. PCT/US2013/032162 filed Mar. 15, 2013.

International Search Report mailed on Jun. 21, 2010 for International Application No. PCT/US2010/027038 filed on Mar. 11, 2010.

Written Opinion for International Application No. PCT/US2011/060057 filed on Nov. 9, 2011.

International Search Report mailed Mar. 18, 2013 for International Application No. PCT/US2012/061749 filed on Oct. 24, 2012.

International Search Report mailed on Jun. 20, 2012 for International Applicaion No. PCT/US2012/031695 filed on Mar. 30, 2012.

International Search Report mailed on Nov. 19, 2014 for International Application No. PCT/US2014/049817 filed on Aug. 5, 2014.

International Search Report for International Application No. PCT/US2010/020448 filed on Jan. 8, 2010.

International Search Report mailed on Mar. 11, 2010 for International Application No. PCT/US2009/069745 filed on Dec. 29, 2009.

International Search Report mailed on Oct. 17, 2011 for International Application No. PCT/US2010/026271 filed on Mar. 4, 2010.

International Search Report for International Application No. PCT/US2010/038287 filed on Jun. 11, 2010.

Ishibashi, Norio et al. "Studies on Flavord Peptides. Part V. A Mechanism for Bitter Taste Sensibility in Peptides." Agricultural and Biological Chemistry, 52(3), 819-27, 1988.

Iwanij et al., Characterization of the Glucagon Receptor and its Functional Domains Using Monoclonal Antibodies. The Journal of Biological Chemistry, vol. 265, No. 34, pp. 21302-21308, 1990.

Jain et al. "Insulin Therapy in Type 2 Diabetic Subjects Suppresses Plasminogen Activator Inhibitor (PAI-1) Activity and Proinsulin-like Molecules Independently of Glycaemic Control." Diabetic Medicine, vol. 10, No. 1, p. 27-32, 1993.

Johnson et al., Peptide turn mimetics. Biotechnology and Pharmacy, p. 366-378 (1993).

Bilheimer DW, Ren H, Boss AH. Analysis of cardiovascular adverse events in patients with type 1 or type 2 diabetes enrolled in selected therapeutic trials in the phase 2/3 Technosphere® insulin development program. ADA 2011. Poster 922-P.

Billings CC, Smutney CC, Howard CP, et al. Handleability and characterization of inhalation profiles using the Gen2 delivery system in a pediatric population. Diabetes Technology Meeting 2010; poster.

Biodel's Intellecutal Property position strengthened for ultra-rapid-acting insulin programs by notice of intent to grant from European Patent Office. Newswire Feed, published May 2, 2012.

Blazquez E et al. "Glucagon-like peptide-1 (7-36) amide as a novel neuropeptide." Mol Neurobio 18:157, 1998.

Bloomgarden "Gut-derived incretin hormones and new therapeutic approaches." Diabetes Care 27:2554, 2004.

Boer et al., Design and application of a new modular adapter for laser diffraction characterization of inhalation aerosols. International Jornal of Pharmaceutics 249, pp. 233-245 (2002).

Boer et al., Inhalation characteristics and their effects on in vitro drug delivery from dry powder inhalers. Part 1. Inhalation characteristics, work of breathing and volunteers' preference in dependence of the inhaler resistance. Int. J. Pharm. 130 (1996) 231-244.

Bojanowska "Physiology and pathophysiology of glucagon-like peptide-1 (GLP-1): the role of GLP-1 in the pathogenesis of diabetes mellitus, obesity and stress." Med Sci Monit 11:RA271, 2005.

Bonner-Weir S et al. "New sources of pancreatic beta-cells." Nat Biotechnol 23:857-61, 2005.

Boss AH et al. "Inhaled Technosphere®/Insulin: Glucose elimination at the right time?" Poster presented at the American Diabetes Association 65th Scientific Sessions, Jun. 2005, abstract 443-P.

Boss AH et al. "Insulin bio-effect is limited by speed of absorption and elimination: similarities between an inhaled insulin formulation that mimics first-phase kinetics and i.v. insulin." Diabetologia 47:A314, 2004.

Boss AH et al. "Mimicry of the early phase insulin response in humans with rapidly available inhaled insulin accelerates post prandial glucose disposal compared to slower bioavailable insulin." Presented at the American Diabetes Association 65th Scientific Sessions, Jun. 2005, abstract 1373-P.

Boss AH et al. "Does kinetics matter? Physiological consequences of the ability of Technosphere®/Insulin inhalation to mimic first phase insulin release." Presented at the 5th Annual Meeting of the Diabetes Technology Society, Nov. 2005, abstract A14.

Boss AH et al. "Markedly reduced post prandial glucose excursions through inhaled Technosphere®/Insulin in comparison to SC injected regular insulin in subjects with type 2 diabetes." 1st Annual Meeting of the European Association for the Study of Diabetes, Sep. 2005, abstract 816.

Boss AH et al. "The variability and time-action profile of inhaled Technosphere®/Insulin compares favorably to that of subcutaneous human regular insulin." Presented at the American Diabetes Association 65th Scientific Sessions, Jun. 2005, abstract 358-OR.

Boss et al. "Prandial Insulin: Is Inhaled Enough?" Drug Development Research 69(3):138-142 (2008).

Boss A H, Petrucci R, Lorber D. Coverage of prandial insulin requirements by means of an ultra-rapid-acting inhaled insulin. Journal of diabetes science and technology 2012;6:773-779.

Boss AH, Baughman RA, Evans SH, et al. A 3 month comparison in type 1 diabetes of inhaled Technosphere®/Insulin (TI) to Sc administered rapid-acting insulin analogue (RAA) as prandial insulin in a basal/prandial regimen. Diabetes 2006; 55:A97.

Boss AH, Evans SH, Firsov I, et al. Technosphere® insulin as effective as sc rapid acting insulin analogue in providing glycemic control in a 6-month study of patients with type 2 diabetes. Diabetes Technology Meeting 2006; poster.

Boss AH, Evans, SH, Ren, H, et al. Superior post prandial glucose control in patients with type 1 diabetes when using prandial technosphere insulin compared to NovoLog. Diabetologia 2006; Abstract 181.

Boss AH, Marino MT, Cassidy JP, et al. C-peptide correction method to determine exogenous insulin levels in pharmacokinetic studies using Technosphere® insulin. Diabetologia 2009; 52 (suppl 1).

(56) References Cited

OTHER PUBLICATIONS

Boss AH, Raskin P, Philips M, et al. Glycosylated hemoglobin and hypoglycaemia in patients with Type 2 diabetes mellitus: Technosphere® insulin and usual antihyperglycaemic regimen vs usual antihyperglycaemic regimen. Diabetologia 2010;53(suppl 1).
Brandt D, Boss AH. The next generation insulin therapy. OndrugDelivery 2006 (published online).
Brange et al., "Insulin Structure and Stability", Pharm Biotechnol, 5:315-50 (1993).
Bray "Exanatide" Am J Health-Sys Pharm 63:411, 2006.
Brownlee et al. "Glycemic variability: a hemoglobin A1c-independent risk factor for diabetic complications." JAMA 295:1707, 2006.
Bruce, D.G., et al. "Physiological importance of deficiency of early prandial insulin secretion in non-insulin-dependent diabetes." Diabetes 37:736-44, 1988.
Bullock BP et al. "Tissue distribution of messenger ribonucleic acid encoding the rat glucagon-like peptide-1 receptor." Endocrinology 137:2968, 1996.
Burcelin et al. "Encapsulated, genetically engineered cells, secreting glucagon-like peptide-1 for the treatment of non-insulin-dependent diabetes mellitus." Ann N Y Acad Sci. Jun. 18, 1999;875:277-85.
Calles-Escandon, J. and Robbins, D.C. "Loss of early phase insulin release in humans impairs glucose tolerance and blunts thermic effect of glucose." Diabetes 36:1167-72, 1987.
Campos et al. "Divergent tissue-specific and developmental expression of receptors for glucagon and glucagon0like peptide-1 in the mouse." Endocrinology 134:2156, 1994.
Cassidy J P, Amin N, Marino M, et al. Insulin lung deposition and clearance following Technosphere® insulin inhalation powder administration. Pharmaceutical Research 2011; 28:2157-2164.
Cassidy J, Amin N, Baughman R, et al. Insulin kinetics following Technosphere® insulin inhalation powder administration unchanged in albuterol-treated asthmatics. ADA 2010; Poster 522.
Cassidy J, Baughman RA, Tonelli G, et al. Use of rapid acting insulin analog as the baseline infusion during glucose clamping improves pharmacokinetic evaluation. ADA 2007; 56: Abstract 602-P.
Cassidy JP, Baughman RA, Schwartz SL, et al. ALFRESA® (Technosphere® insulin) dosage strengths are interchangeable ADA 2009; Poster 433.
Cassidy JP, Marino MT, Amin N, et al. Lung deposition and absorption of insulin from AFRESA® (Technosphere® insulin) ADA 2009; Poster 425.
Cassidy JP, Potocka E, Baughman RA, et al. Pharmacokinetic characterization of the Technosphere® inhalation platform Diabetes Technology Meeting 2009. poster.
Caumo et al. "First-phase insulin secretion: does it exist in real life" Considerations on shape and function. Am J Physiol Endocrinol Metab 287:E371-E385, 2004.
Cefalu "Concept, Strategies and Feasibility of Noninvasive Insulin Delivery." Diabetes Care 27:239-246, 2004.
Cefalu "Novel routes of insulin delivery for patients with type 1 or type 2 diabetes." Ann Med 33:579-586, 2001.
Cefalu et al., Inhaled human insulin treatment in patients with type 2 diabetes mellitus. Ann. Int. Med., 2001, 134(3): 203-207.
Ceglia et al. "Meta-analysis: efficacy and safety of inhaled insulin therapy in adults with diabetes mellitus." Ann Intern Med 145:665, 2006.
Cerasi, et al. Decreased sensitivity of the pancreatic beta cells to glucose in prediabetic and diabetic subjects. A glucose dose-response study. Diabetes 21(4):224-34, 1972.
Cernea et al. "Dose-response relationship of oral insulin spray in healthy subjects." Diabetes Care 28:1353-1357, 2005.
Cernea et al. "Noninjectable Methods of Insulin Administration." Drugs of Today 2006, 42 (6): 405-424.
Chan et al., "Pharmacological Management of Type 2 Diabetes Mellitus: Rationale for Rational Use of Insulin", Mayo Clin Proc, 2003, 78, 459-466.
Chase et al., "Redefining the clinical remission period in children with type 1 diabetes", Pediatric Diabetes, 2004, 5, 16-19.
Cheatham et al. "Desirable Dynamics & Performance of Inhaled Insulin Compared to Subcutaneous Insulin Given at Mealtime in Type 2 Diabetes: A Report from the Technosphere/Insulin Study Group." Diabetes Technology and Therapeutics, vol. 6, p. 234 (2004).
Cheatham et al. "A novel pulmonary insulin formulation replicates first phase insulin release and reduces s-proinsulin levels." Presented at the American Diabetes Association 64th Scientific Sessions, Jun. 2004, abstract 457-P.
Johnson et al., "Turbuhaler a new device for dry powder terbutaline inhalation", Allergy 43(5):392-395 (1988).
Johnson et al: RyR2 and calpain-10 delineate a novel apoptosis pathway in pancreatic islets. J Biol Chem., 279 (23):24794-802, 2004.
Johnson, Keith A., Preparation of peptide and protein powders for inhalation. Advanced Drug Delivery Reviews 1997; 26:3-15.
Jones et al., An investigation of the pulmonary absorption of insulin in the rat. Third European Congress of Biopharmaceutics and Pharmacokinetics, (1987).
Joseph et al. "Oral delivery of glucagon-like peptide-1 in a modified polymer preparation normalizes basal glycaemia in diabetic db/db mice." Diabetologia 43:1319-1328, 2000.
Joy et al. "Incretin mimetics as emerging treatments for type 2 diabetes." Annal Pharmacother 39:110, 2005.
Juntti-Berggren et al. "The antidiabetogenic effect of GLP-1 is maintained during a 7-day treatment period and improves diabetic dyslipoproteinemia in NIDDM patients." Diabetes Care 19:1200-1206, 1996.
Kanse et al. "Identification and characterization of glucagon-like peptide-1 7-36 amide-binding sites in the rat brain and lung." FEBS Letters 241:209, 1988.
Kapitza C et al. "Impact of particle size and aerosolization time on the metabolic effect of an inhaled insulin aerosol." Diabetes Tech Ther 6:119, 2004.
Kapitza et al. "Dose-response characteristics for a new pulmonary insulin formulation and inhaler." Presented at the 35th Annual Meeting of the EASD, Sep. 2000, abstract OP29 184.
Kapsner P, Bergenstal RM, Rendell M, et al. Comparative efficacy and safety of Technosphere® insulin and a rapid-acting analog both given with glargine in subjects with type 1 diabetes in a 52-week study. Diabetologia 2009; 52 (suppl 1).
Katchalski E et al. "Synthesis of lysine anhydride", J. Amer Chem Soc 68:879-880, 1946.
Katz et al. "Quantitative insulin sensitivity check index: a simple, accurate method for assessing insulin sensitivity in humans." J. Clin. Endocrinol. Metab. 85:5402-2410, 2000.
Kaur et al. "A Delineation of Diketopiperazine Self-Assembly Processes: Understanding the Molecular Events Involved in Ne-(Fumaroyl)diketopiperazine of L-Lys (FDKP) Interactions." Molecular Pharmaceutics, vol. 5, No. 2, 294-315, 2008.
Kawai et al. "Evidence that glucagon stimulates insulin secretion through its own receptor in rats." Diabetologia 38:274, 1995.
Kawamori et al. "Does hyperinsulinemia accelerate atherosclerosis?" Department of Medicine, Juntendo University School, vol. 13, No. 12, p. 954-960, 1994.
Kelley, D. et al. "Impaired postprandial glucose utilization in non-insulin dependent diabetes mellitus." Metabolism 43:1549-1557, 1994.
Kenny AJ et al. "Dipeptidyl peptidase IV, a kidney brush-border serin peptidase." Biochem J. 155:169, 1976.
Kim et al. "Development and characterization of a glucagon-like peptide 1-albumin conjugate. The ability to activate the glucagon-like peptide 1 receptor in vivo." Diabetes 52:751, 2003.
Kinzig et al. "The diverse roles of specific GLP-1 receptors in the control of food intake and the response to visceral illness." J Neurosci 22:10470, 2002.
Kirk et al. "Disparities in HbA1c levels between African-American and non-hispanic white adults with diabetes." Diabetes Care 29:2130, 2006.
Kitabchi, Proinsulin and C-peptide:a review. May 26, 1977 (5):547-87, http://www/ncbi.nlm.nih.gov/pubmed/403392.
Klinger et al., Insulin-micro and nanoparticles for pulmonary delivery. International Journal of Pharmaceutics, vol. 377, pp. 173-179 (2009).

(56) References Cited

OTHER PUBLICATIONS

Knop et al. "No hypoglycemia after subcutaneous administration of glucagon-like peptide-1 in lean type 2 diabetic patients and in patients with diabetes secondary to chronic pancreatitis." Diabetes Care 26:2581, 2003.
Knop et al. "Reduced incretin effect in type 2 diabetes. Cause or consequence of the diabetic state?" Diabetes 56:1951, 2007.
Kohler D et al. Non-radioactive approach for measuring lung permeability: inhalation of insulin. Atemw Lungenkrkh 13:230-232, 1987. (Original German and English translation attached).
Kohler, "Aerosols for Systemic Treatment", Lung (Suppl.) 677-684 (1990).
Komada et al., Intratracheal delivery of peptide and protein agents: absorption from solution and dry powder by rat lung. J. Pharm. Sci. 83(6): 863-867 (1994).
Komatsu et al. "Glucagonostatic and insulinotropic action of glucagon-like peptide-1 (7-36)-amide." Diabetes 38:902, 1989.
Koning et al., Relationship between inspiratory flow through simulated dry powder inhalers and peak maximal inspiratory pressure. Dry powder inhalation: technical and physiological aspects, prescribing and use. Chapter 3, 2001, pp. 43-56.
Kontny et al., Issues Surrounding MDI Formulation Development with Non-CFC Propellants), J. Aerosol Med 4(3), 181-187 (1991).
Kopple et al. "A convenient synthesis of 2,5-piperazinediones." J Org Chem p. 962, 1967.
Kraft KS, Grant M. Preparation of macromolecule-containing drug powders for pulmonary delivery Methods in Molecular Biology 2009;480:165-174.
Kreymann B et al. "Glucagon-like peptide-1 7-36: a physiological incretin in man." The Lancet, Dec. 5, 1987, p. 1300.
Krssak, M. et al. "Alterations in postprandial hepatic glycogen metabolism in type 2 diabetes." Diabetes 53:3048-3056, 2004.
Krueger et al. "Toxicological profile of pulmonary drug delivery agent." Presented at the American Diabetes Association 64th Scientific Sessions, Jun. 2004, abstract 465-P.
Kwon et al. "Signaling elements involved in the metabolic regulation of mTOR by nutrients, incretins, and growth factors in islets." Diabetes 53:S225, 2004.
Lankat-Buttgereit B et al. "Molecular cloning of a cDNA encoding for the GLP-1 receptor expressed in rat lung." Exp Clin Endocrinol 102:241, 1994.
Laureano et al. "Rapid absorption and elimination of insulin from the lung following pulmonary administration of Technosphere®/Insulin: A pharmacokinetic study in a rat model." Presented at the American Diabetes Association 65th Scientific Sessions, Jun. 2005, abstract 445-P.
Leahy et al. Beta-cell dysfunction in type II diabetes mellitus. Curr Opin Endocrinol Diabetes 2:300-306, 1995.
Lebovitz "Therapeutic options in development for management of diabetes: pharmacologic agents and new technologies." Endocr Pract 12:142, 2006.
Lee et al. "Synthesis, characterization and pharmacokinetic studies of PEGylated glucagon-like peptide-1." Bioconjugate Chem 16:377, 2005.
Lee et al., "Development of an Aerosol Dosage Form Containing Insulin", J. Pharm. Sci. 65(4), 567-572 (1976).
Leiner et al. "Particles facilitate the absorption of insulin in a primary cell culture model of alveolar epithelium without evidence of cytotoxicity." Presented at the American Diabetes Association 64th Scientific Sessions, Jun. 2004, abstract 467-P.
Leiner et al. "The pharmacokinetic profile of insulin administered by inhalation in the rat." Diabetes 53 Supplement, Jun. 2004, A111.
Leone-Bay et al. "Evaluation of novel particles as an inhalation system for GLP-1." Diabetes, Obesity and Metabolism. 11:1050-1059, 2009.
Leone-Bay A, Grant M. Technosphere® Technology: A Platform for inhaled protein therapeutics. OndrugDelivery 2006 (published online).
Leone-Bay A, Grant M. Technosphere®/insulin: mimicking endogenous insulin release. In: Rathbone M, Hadgraft J, Roberts M, et al, eds. Modified Release Drug Delivery, 2e. New York, NY: Informa Healthcare USA, Inc; 2008.
Kieffer et al. "The glucagon-like peptides." Endocrine Reviews 20:876, 1999.
Li et al. "GLP-1; a novel zinc finger protein required in somatic cells of the gonad for germ cell development." Dev Biol 301:106, 2007.
Li, Jun. Chapter 15: Drug Therapy of Metabolic Diseases. Clinical Pharmacotherapy, People's Medical Publishing House, 1st Edition, pp. 333-335 (2007).
Lian et al. "A Self-Complimentary Self-Assembling Microsphere System: Application for Intravenous Delivery of the Antiepilpetic and Neuroprotectant Compound Felbanate." J Pharm Sci 89:867-875, 2000.
Lim, "Microencapsulation of Living Cells and Tissues", J. Pharm. Sci., 70: 351-354 (1981).
Linder et al., Increase in serum insulin levels is correlated with lung distribution after pulmonary delivery of Technospherellnsulin. Diabetologia, No. 46, A277 (2003).
Liu et al., "Pulmonary delivery of free and liposomal insulin", Pharmaceuticals Res. 10:228-232, 1993.
Lorber D, Howard CP, Ren H, et al. Reduced incidence and frequency of hypoglycemia in an integrated analysis of pooled data from clinical trials of subjects with type 2 diabetes using prandial inhaled Technosphere® insulin. AACE 2010; Poster 270.
Luque et al. "Glucagon-like peptide-1 (GLP-1) and glucose metabolism in human myocytes." J. Endocrinol 173:465, 2002.
Luzi, L. and DeFronzo, R.A. "Effect of loss of first-phase insulin secretion on hepatic glucose production and tissue glucose disposal in humans." Am. J. Physiol. 257 (Endocrinol. Metab. 20):E241-E246, 1989.
Luzio, S.D., et al. "Intravenous insulin simulates early insulin peak and reduces post-prandial hyperglycaemia/hyperinsulinaemia in type 2 (non-insulin-dependent) diabetes mellitus." Diabetes Res. 16:63-67, 1991.
Malhotra et al., Regulatory Peptides, 41:149-56, 1992.
Mandal "Inhaled insulin for diabetes mellitus." Am J Health Sys Pharm 62:1359-64, 2005.
Mann "Pulmonary insulin—the future of prandial insulin therapy." Presented at the 5th Annual Meeting of the Diabetes Technology Society, Nov. 2005, abstract A94.
Mannkind Corporation "Postprandial hyperglycemia: clinical significance, pathogenesis and treatment." MannKind Corporation Monograph. 2009.
Mannkind Corporation, Pulmonary Delivery: Innovative Technologies Breathing New Life into Inhalable Therapeutics, www.ondrugdelivery.com, 2006.
Mannkind Corporation. Technosphere Technology: A Platform for Inhaled Protein Therapeutics. Pulmonary Delivery, (www.ondrugdelivery.com), pp. 8-11, 2006.
Marino MT, Cassidy JP, Smutney CC, et al. Bioequivalence and dose proportionality of Afrezza® inhalation powder administered using a Gen2 inhaler compared to the MedTone® inhaler. Diabetes Technology Meeting 2010; poster.
Marino MT, Cassidy JP, Smutney CC, et al. Improvement in bioavailability of FDKP with the NexGen2A device: Implications for delivery of pulmonary insulin. Third International Conference on Advanced Technologies and Treatments for Diabetes 2010; Poster 108.
Marino MT, Cassidy JP, Smutney CC, et al. Improvement in bioavailability of FDKP and insulin with the NGDSB device. Third International Conference on Advanced Technologies and Treatments for Diabetes 2010; Poster 107.
Marino MT. A pharmacokinetic/pharmacodynamic model of inhaled insulin with application to clinical trial simulation. ADA 2010; Abstract 2105-PO.
Marino MT. Cassidy JP, Baughman RA, et al. C-peptide correction method to determine exogenous insulin levels in pk studies using AFRESA® (Technosphere® insulin [TI]) ADA 2009; Poster 1451.
Marshall "Preventing and detecting complications of diabetes." BMJ 333:455, 2006.
Mastrandrea "A breath of life for inhaled insulin: severe subcutaneous insulin resistance as an indication." Pediatric Diabetes 2010: 11: 377-379.

(56) References Cited

OTHER PUBLICATIONS

Mathiowitz, Morphology of Polyanhydride Microsphere Delivery Systems, Scanning Microscopy, 4: 329-340 (1990).
Mathiowitz, Novel microcapsules for delivery systems. Reactive Polymers, 6: 275-283 (1987).
Mathiowitz, Polyanhydride microspheres as drug carriers I, hot-melt microencapsulation. J. Controlled Medicine, 5: 13-22 (1987).
Mathiowitz, Polyanhydride microspheres as drug carriers II, microencapsulation by solvent removal. J. Appl. Polymer Sci., 35: 755-774 (1988).
Mathiowitz, Polyanhydride microspheres IV, morphology and characterization systems made by spray drying. J. App. Polymer Sci., 45: 125-134 (1992).
Matsui et al. "Hyperplasia of type II pheumocytes in pulmonary lymphangioleiomyomatosis. Immunohistochemical and electron microscope study." Arch Pathol Lab Med 124:1642, 2000.
Matthews DR et al. "Homeostasis model assessment: insulin resistance and beta-cell function from fasting plasma glucose and insulin concentrations in man." Diabetologia. Jul. 1985;28(7):412-9.
McElduff A et al. "Influence of acute upper respiratory tract infection on the absorption of inhaled insulin using the AERx(R) insulin diabetes management system." Br J Clin Pharmacol 59:546, 2005.
McMahon et al., "Effects of basal insulin supplementation on disposition of mixed meal in obese patients with NIDDM", Diabetes, vol. 38, pp. 291-303 (1989).
Meier et al. "Absence of a memory effect for the insulinotropic action of glucagon-like peptide-1 (GLP-1) in healthy volunteers." Horm Metab Res 35:551, 2003.
Meier et al. "Secretion, degradation, and elimination of glucagon-like peptide-1 and gastric inhibitor polypeptide in patients with chronic renal insufficiency and healthy control subjects." Diabetes 53:654, 2004.
Meier et al. "The glucagon-like peptide-1 metabolite GLP-1-(9-36) amide reduces postprandial glycemia independently of gastric emptying and insulin secretion in humans." Am J Physiol Endocrinol Metab 290:E1118, 2006.
Mendes et al., A non-dimensional functional relationship for the fine particle fraction produced by dry powder inhalers, Aerosol Science 38, pp. 612-624 (2007).
Mentlein et al., Dipeptidyl peptidase IV hydrolyses gastric inhibitory polypeptide, glucagon-like peptide-1 (7-36) amide, peptide histidine methionine and is responsible for their degradation in human serum. Eur J Biochem., 214:829-835, 1993.
Merck Manual 17th, Japanese Edition, NIKKEI BP Corp., 1999, p. 167-179.
Mitchell et al. "Intranasal Insulin: PK Profile Designed Specifically for Prandial Treatment of Type 2 Diabetes." Drug Development Research 69(3):143-152 (2008).
Monnier et al. "Activation of oxidative stress by acute glucose fluctuations compared with sustained chronic hyperglycemia in patients with type 2 diabetes." JAMA 295:1681, 2006.
Montrose-Rafizadeh et al., Diabetes, 45(Suppl. 2):152A, 1996.
Mudaliar et al., Insulin Therapy in Type 2 Diabetes. Endocrinology and Metabolism Clinics, vol. 30, No. 4, pp. 1-32 (2001).
Nagai et al., "Powder Dosage Form of Insulin for Nasal Administration", J. Control Ref., 1:15-22 (1984).
Narayan et al. "Impact of recent increase in incidence on future diabetes burden." Diabetes Care 29:2114, 2006.
Naslund E et al. "GLP-1 slows solid gastric emptying and inhibits insulin, glucagon, and PYY release in humans." Am J Physiol (Regulatory Integrative Comp Physiol 46):R910, 1999.
Naslund E et al. "Prandial subcutaneous injections of glucagon-like petide-1 cause weight loss in obese human subjects." Br J Nutrition 91:439, 2004.
Naslund et al. "GLP-1 slows solid gastric emptying and inhibits insulin, glucagon, and PYY release in humans." Am J Physiol (Regulatory Integrative Comp Physiol 46):R910, 1999.
Nathan DM et al. "Management of hyperglycemia in Type 2 diabetes: a consensus algorithm for the initiation and adjustment of therapy." Diabetes Care 29:1963, 2006.
Marino MT, Cassidy JP, Smutney CC, et al. Improvement in bioavailability of FDKP with the NexGen2A device: Implications for delivery of pulmonary insulin. Diabetes Technology Meeting 2009; poster.
Pfutzner et al. "Inhaled Technosphere/Insulin Shows a Low Variability in Metabolic Action in Type 2 Diabetic Patients." Diabetes 49 Supplement, May 2000, A121.
Pfuetzner A, Rave K, Heise T, et al. Inhaled Technosphere™/insulin results in low variability in metabolic action in type 2 diabetic patients. Exp Clin Endocrinol Diabetes 2000; 108:S161.
Pfuetzner A, Rave K, Heise T, et al. Low variability in metabolic action in type 2 diabetic patients with inhaled Technosphere/insulin. Diabetologia 2000; 43:Abstract 774.
Phillips M, Amin N, Boss AH, et al. Pulmonary functions (over 2 years) in diabetic subjects treated with Technosphere® insulin or usual antidiabetic treatment. Diabetologia 2009; 52 (suppl 1).
Pohl R, Muggenberg BA, Wilson BR, et al. A dog model as predictor of the temporal properties of pulmonary Technosphere/insulin in humans. Respiratory Drug Delivery 2000; VII: 463-465.
Polonsky et al. "Abnormal Patterns of Insulin Secretion in Non-insulin-Dependent Diabetes Mellitus." N Eng J Med 318:1231-39, 1988.
Potocka E, Amin N, Cassidy J, et al. Insulin pharmacokinetics following dosing with Technosphere® insulin in subjects with chronic obstructive pulmonary disease. Current Medical Research and Opinion 2010; 26:2347-2353.
Potocka E, Baughman R A, Derendorf H. Population pharmacokinetic model of human insulin following different routes of administration. Journal of Clinical Pharmacology 2011;51:1015-1024.
Potocka E, Baughman R, Derendorf H. Population Pharmacokinetic Model of Regular Human Insulin Following Different Routes of Administration. AAPS Journal. 2009; 11(S1). Available from: http://www.aapsj.org. Presented at the 2009 AAPS (American Association of Pharmaceutical Scientists) National Biotechnology Conference, Jun. 21-24, Seattle, WA.
Potocka E, Baughman RA, Derendorf J. A population PK/PD model of Technosphere® insulin administered to healthy and type 2 diabetics. ADA 2010; Poster 624.
Potocka E, Baughman RA, Schwartz SL, et al. Pharmacokinetics of AFRESA® unchanged in patients with chronic obstructive pulmonary function ADA 2009; Poster 437.
Potocka E, Cassidy J P, Haworth P, et al. Pharmacokinetic characterization of the novel pulmonary delivery excipient fumaryl diketopiperazine. Journal of diabetes science and technology 2010;4:1164-1173.
Potocka E, Cassidy JP Haworth P, et al. Pharmacokinetic characterization of fumaryl diketopiperazine. Third International Conference on Advanced Technologies and Treatments for Diabetes 2010; Poster 291.
Potocka E, Hovorka R, Baughman R, et al. Characterization of metabolism parameters following Technosphere® insulin and insulin Lispro. ADA 2010; Poster 1561.
Potocka E, Hovorka R, Baughman RA, et al. AFRESA™ supresses endogenous glucose production earlier than a rapid-acting analog (Lispro) and inhaled Exubera® ADA 2009; Oral 232.
Potocka E, Hovorka R, Baughman RA, et al. Technosphere® insulin suppresses endogenous glucose production earlier than a rapid-acting analog (lispro) and an inhaled insulin (exubera). Diabetologia 2009; 52 (suppl 1).
Prabhu et al. "A study of factors controlling dissolution kinetic of zinc complexed protein suspensions in various ionic species", Int. J. Pharm. 217(1-2):71-8 (2001).
Pulmonary Delivery: Innovative Technologies breathing new life into inhalable therapeutics, Ondrug Delivery, MannKind, pp. 1-24 (2006).
Quattrin et al. "Efficacy and Safety of Inhaled Insulin (Exubera) Compared with Subcutaneous Insulin Therapy in Patients with Type 1 Diabetes." Diabetes Care, vol. 27, No. 11, Nov. 2004, p. 2622-2627.
Quddusi et al. "Differential effects of acute and extended infusions of glucagon-like peptide-1 on first- and second-phase insulin secretion in diabetic and nondiabetic humans." Diabetes Care 26:791, 2003.

(56) References Cited

OTHER PUBLICATIONS

Rachman et al. "Normalization of insulin responses to glucose by overnight infusion of glucagon-like peptide 1 (7-36) amide in patients with NIDDM." Diabetes 45:1524, 1996.
Raju et al., Naseseazines A and B: a new dimeric diketopiperazine framework from a marine-derived actinomycete, *Streptomyces* sp. Organic letters, vol. 11, No. 17, pp. 3862-3865 (2009).
Raskin et al. "Continuous subcutaneous insulin infusion and multiple daily injection therapy are equally effective in type 2 diabetes." Diabetes Care, vol. 26, No. 9, pp. 2598-2603, Sep. 2003.
Raskin P, Heller S, Honka M, et al. Pulmonary function over 2 years in diabetic patients treated with prandial inhaled Technosphere® Insulin or usual antidiabetes treatment: A randomized trial. Diabetes, Obesity and Metabolism 2012;14:163-173.
Raskin P, Phillips M, Amin N, et al. Hypoglycemia in patients with type 1 diabetes incorporating prandial inhaled Technosphere® insulin into their usual diabetes treatment regiment vs continuing their usual diabetes management. AACE 2010; Poster 283.
Raskin P, Phillips MD, Rossiter A, et al. A1C and hypoglycemia in patients with type 2 diabetes mellitus incorporating prandial inhaled Technosphere® insulin into their usual antihyperglycemic regimen vs continuing their usual antihyperglycemic regimen. ADA 2010; Abstract 359-OR.
Raufman et al., Exendin-3, a novel peptdie from Heloderma horridum venom, interacts with vasoactive intestinal peptide receptors and a newly described receptor on dispersed aciin from guinea pig pancreas. J. Biol. Chem. 266(5) : 2897-2902 (1991).
Raufman et al., Truncated glucagon-like peptide-1 interacts with exendin receptors on dispersed acini from guina pig pancreas. J. Biol. Chem. 267(30) : 21432-21437 (1992).
Raun et al. "Liraglutide, a long-acting glucagon-like peptide-1 analog, reduces body weight and food intake in obese candy-fed rats, where as a dipeptidyl peptidase-IV inhibitor, vildagliptin, does not." Diabetes 56:8, 2007.
Rave et al. "Coverage of Postprandial Blood Glucose Excursions with Inhaled Technosphere Insulin in Comparison to Subcutaneously Injected Regular Human Insulin in Subjects with Type 2 Diabetes." Diabetes Care, vol. 30, No. 9, pp. 2307-2308, Sep. 2007.
Rave et al. "Dose Response of Inhaled Dry-Powder Insulin and Dose Equivalence to Subcutaneous Insulin Lispro."Diabetes Care 28:2400-2405, 2005.
Rave et al. "Inhaled Technosphere Insulin in Comparison to Subcutaneous Regular Human Insulin: Time Action Profile and Variability in Subjects with Type 2 Diabetes." Journal of Diabetes Science and Technology, vol. 2, Issue 2, pp. 205-212, Mar. 2008.
Rave et al. "Results of a Dose-Response Study with a New Pulmonary Insulin Formulation and Inhaler." Diabetes 49, Supplement, May 2000, A75.
Rave et al. "Time-action profile of inhaled insulin in comparison with subcutaneously injected insulin lispro and regular human insulin." Diabetes Care 28:1077, 2005.
Rave K, Heise T, Pfuetzner A, et al. Assessment of dose-response characteristics for a new pulmonary insulin formulation and inhaler. Exp Clin Endocrinol Diabetes 2000; 108:S161.
Rave K, Potocka E, Boss AH, et al. Pharmacokinetics and linear exposure of AFRESA™ compared with the subcutaneous injection of regular human insulin Diabetes, Obesity and Metabolism 2009; 11:715-720.
Raz et al. "Pharmacodynamics and Pharmacokinetics of Dose Ranging Effects of Oralin versus S.C. Regular Insulin in Type 1 Diabetic Patients." Fourth Annual Diabetes Technology Meeting, Philadelphia PA, 2004.
Razavi et al. "TRPVI+ sensory neurons control beta cell stress and islet inflammation in autoimmune disease." Cell 127:1123, 2006.
Retrieved from website: http://groups.molbiosci.northwestern.edu/holmgren/Glossary/Definitions/Def-P/placebo.html, 1 page, Retrieved on Mar. 12, 2013.
Rhodes et al. "Technosphere: Microspherical Particles from Substituted Diketopiperazines for Use in Oral Drug Delivery." 208th ACS National Meeting, Aug. 1994.
Richardson et al. "Technosphere Insulin Technology." Diabetes Technology & Therapeutics, vol. 9, Supplement 1, pp. S65-S72, 2007.
Richardson PC, Potocka E, Baughman RA, et al. Pharmacokinetics of Technosphere® insulin unchanged in patients with chronic obstructive pulmonary disease. Diabetologia 2009; 52 (suppl 1).
Richter et al. "Characterization of glucagon-like peptide-1(7-36)amide receptors of rat membranes by covalent cross-linking." FEBS Letters 280:247, 1991.
Richter et al. "Characterization of receptors for glucagon-like peptide-1 (7-36)amide on rat lung membranes." FEBS Letters 267:78, 1990.
Riddle "Combining Sulfonylureas and Other Oral Agents." Am J Med, 2000, vol. 108(6A), pp. 15S-22S.
Riddle et al. "Emerging therapies mimicking the effects of amylin and glucagon-like peptide 1." Diabetes Care 29:435, 2006.
Ritzel et al. "Pharmacokinetic, insulinotropic, and glucagonostatic properties of GLP-1 (7-36 amide) after subcutaneous injection in healthy volunteers. Dose-response-relationships." Diabetologia 38:720, 1995.
Rosen et al., Substance P microinjected into the periaqueductal gray matter induces antinociception and is released folloing morphine administration. Brain Research, 1001: 87-94 (2004).
Rosenmund et al., Diketopiperazines from Leuchs Anhydrides. Angew Chem Intern. Edit. vol. , No. 2 (1970).
Rosenstock "Dual therapy with inhaled human insulin (Exubera(R)) as add-on to metformin (with stopping sulfonurea) is better than triple therapy with rosiglitazone add-on to combination metformin and sulfonurea in poorly controlled Type 2 diabetes." Diabetes 57:supplement 1:A557, Abstract 2018-PO, 2008.
Rosenstock et al. "Efficacy and Safety of Technosphere Inhaled Insulin Compared With Technosphere Powder Placebo in Insulin-Naive Type 2 Diabetes Suboptimally Controlled with Oral Agents." Diabetes Care, vol. 31, No. 11, pp. 2177-2182, Aug. 2008.
Rosenstock et al. "Inhaled Insulin Improves Glycemic Control when Substituted for or Added to Oral Combination Therapy in Type 2 Diabetes." Ann Intern Med 143:549-558, 2005.
Rosenstock et al., "Reduced hypoglycemia risk with insulin glargine: a meta-analysis comparing insulin glargine with human NPH insulin in type 2 diabetes", Diabetes Care, 28(4):950-5 (2005).
Rosenstock J, Baughman RA, Ribera-Schaub T, et Al. A randomized, double-blind, placebo controlled study of the efficacy and safety of inhaled Technosphere® insulin in patients with type 2 diabetes (T2DM). Diabetes 2005;54: Abstract 357-OR.
Rosenstock J, Lorber D, Petrucci R, et al. Basal/bolus with prandial inhaled Technosphere® insulin (TI) plus insulin glargine qd vs biaspart 70/30 insulin bid in T2 DM inadequately controlled on insulin with/without oral agents ADA 2009; Poster 466.
Rosenstock J, Lorger DL. Gnudi L, et al.Prandial inhaled insulin plus basal insulin glargine versus twice daily biaspart insulin for type 2 diabetes: a multicentre randomized trial. Lancet 2010;375:2244-2253.
Rossiter A, Amin N, Harris R, et al. Pulmonary safety of inhaled Technosphere® insulin therapy in adults with diabetes using high-resolution computerized tomography of the chest. Diabetologia 2009; 52 (suppl 1).
Rossiter A, Howard C, Amin N, et al. Technosphere® insulin: Safety in type 2 diabetes mellitus. ADA 2010; Poster 523.
Roumeliotis, New inhaler launched with a bag, in-Pharma Technologist.com, Decision News Media SAS (2006).
Rousseau et al. "Drug delivery by fumaryl diketopiperazine particles: evidence for passive transport." Presented at the American Diabetes Association 64th Scientific Sessions, Jun. 2004, abstract 484-P.
Rubin RR, Peyrot M. Psychometric properties of an instrument for assessing the experience of patients treated with inhaled insulin: The inhaled insulin treatment questionnaire (INTQ) Health & Quality of Life Outcomes 2010.8:32.
Rubin RR, Peyrot M; Patient reported outcomes in adults with type 1 diabetes using mealtime AFRESA® (inhaled Technosphere® insulin) or rapid acting insulin with basal insulin ADA 2009; Poster 1881.
Ryan EA et al. "Successful islet transplantation. Continued insulin reserve provides long-term glycemic control." Diabetes 51:2148-2157, 2002.

(56) References Cited

OTHER PUBLICATIONS

Sajeesh et al., Cyclodextrin-insulin complex encapsulated polymethacrylic acid based nanoparticles for oral insulin delivery. International Journal of Pharmaceuticals, 2006, 325, pp. 147-154.
Sakagami M et al. "Respirable microspheres for inhalation: the potential of manipulating pulmonary disposition for improved therapeutic efficacy." Clin Pharmacokinet 44(3):263-277, 2005.
Sakr, A new approach for insulin delivery via the pulmonary route: design and pharmacokinetics in non-diabetic rabbits. International Journal of Pharmaceutics, 86: 1-7 (1992).
Salib, Utilization of sodium alginate in drug microencapsulation. Pharazeutische Industrie, 40(11a): 1230-1234 (1978).
Saraceni C et al. "Effects of glucagon-like peptide-1 and long-acting analogues on cardiovascular and metabolic function." Drugs R D 8:145, 2007.
Sarrach et al., "Binding and entrapment of insulin by liposomes made of lecithin-phosphotidix acid in acid solution" Pharmazie 40:642-645, 1985 (German and English Abstract).
Savage et al., "Effects of peptide YY (PYY) on mouth to caecum intestinal transit time and on the rate of gastric emptying healthy volunteers", Gut, vol. 28, pp. 166-170, 1987.
Sawhney, Bioerodible hydrogels based on photopolymerized poly-(ethylene glycol)-co-poly(a-hydroxy acid) diacrylate macromere Macromolecules, 26: 581-587 (1993).
Schaffer et al. "Assembly of high-affinity insulin receptor agonists and antagonists from peptide building blocks." PNAS 100:4435, 2003.
Schepp et al., Eur. J. Pharmacol., 69:183-91, 1994.
Scherbaum "Unlocking the opportunity of tight glycaemic control. Inhaled insulin: clinical efficacy." Diabetes Obesity and Metabolism 7:S9, 2005.
Schirra et al. "Gastric emptying and release of incretin hormones after glucose ingestion in humans." J Clin Invest 97:92, 1996.
Schluter et al., "Pulmonary Administration of Human Insulin in volunteers and Type I Diabetics", Diabetes, 33, (Suppl) 298 (1984).
Schneider et al., "Stimulation by proinsulin of expression of plasminogen axtivator inhibiror type 1 in endothelial cells", Diabetes 41(7):890-895 (1992).
Schon, Istvan et al. "Formation of Aminosuccinyl Peptides During Acidolytic Deprotection Followed by their Tranformation to Piperazine-2, 5-dione Derivatives in Neutral Media." International Journal of Peptide & Protein Research, 14(5), 485-94m 1979.
Schroder, "Crystallized carbohydrate spheres as a slow release matrix for biologically active substances", Biomaterials 5:100-104, 1984.
Scrocchi et al. "Glucose intolerance but normal satiety in mice with a null mutation in the glucagon-like peptide 1 receptor gene." Nature Medicine 2:1254, 1996.
Seshiah & Balaji, "Early Insulin Therapy in Type 2 Diabetics", Int. J. Diabetes in Developing Countries, 2003, 23, 90-93.
Seville, P.C. et al., Preparation of dry powder dispersions for non-viral gene delivery by freeze-drying and spray drying. J. Gene Medicine 2002; 4:428-437.
Shah et al. "Lack of suprression of glucagon contributes to postprandial hyperglycemia in subjects with type 2 diabetes mellitus." J Clin Indocrinol Metab 85:4053, 2000.
Shelly et al. "Polysorbate 80 hypersensitivity." The Lancet 345:1312, 1995.
Shimada et al. Translocation pathway of the intertracheally instilled ultrafine particles from the lung into the blood circulation in the mouse. Toxicologic Pathology pp. 949-957 (2006).
Shojania et al. "Effect of quality improvement strategies for type 2 diabetes on glycemic control." JAMA 296:427, 2006.
Silverstein et al., "Care of Children and Adolescens with Type 1 Diabetes, A Statement of the American Diabetes Association", Diabetes Care, Jan. 2005, vol. 28, p. 186-212.
Singh et al., Use of 125I-[Y39]exendin-4 to characterize exendin receptors on dispersed pancreatic acini and gastric chief cells from guinea pig. Regul. Pept. 53 : 47-59 (1994).
Simms JR, Carballo I, Auge CR, et al. Assessment of immunotoxic effects on humoral and cellular immune parameters following repeated inhalation of Technosphere insulin in the rat. Diabetes 2005;54:Abstract 2078-PO.
Skyler, Pulmonary insulin: current status. Diabetes Voice, vol. 51, Issue I, p. 23-25, 2006.
Skyler "Pulmonary Insulin Delivery—State of the Art 2007." Diabetes Tecnology & Therapeutics, vol. 9, Supplement 1, pp. S1-S3. 2007.
Skyler JS et al. "Use of inhaled insulin in a basal/bolus insulin regimen in Type 1 diabetic subjects." Diabetes Care 28:1630-1635, 2005.
Smith et al. "New-onset diabetes and risk of all-cause and cardiovascular mortality." Diabetes Care 29:2012, 2006.
Smutney CC, Friedman EM, Amin N. Inspiratory efforts achieved in use of the Technosphere® insulin inhalation system. Diabetes Technology Meeting 2008; Poster SMUT8052.
Smutney CC, Friedman EM, Amin N. Inspiratory efforts achieved in use of the Technosphere® insulin inhalation system. Journal of Diabetes Science and Technology 2009 3(5):1175-1189.
Smutney CC, Polidoro JM, Adamo B, et al. In-vitro performance improvement realized in a next generation dry powder delivery system. Diabetes Technology Meeting 2009; poster.
Smutney CC, Polidoro JM, Adamo B, Shah S. In vitro performance improvement realized in a next generation dry powder delivery system. Third International Conference on Advanced Technologies and Treatments for Diabetes 2010; Poster 122.
Smutney CC, Polidoro JM. Easy-to-use next-generation pulmonary insulin delivery system. ADA 2010; Abstract 2093.
Smutney CC, Polidoro JM. Improvements realized in a next-generation pulmonary insulin delivery system. ADA 2010; Abstract 2097.
Sodium chloride is a natural product from http://www.wqpmag.com/potassium-chloride-vs-sodium-chloride, pp. 1-3.
Nathan DM et al. "Management of hyperglycemia in Type 2 diabetes: a consensus algorithm for the initiation and adjustment of therapy." Diabetes Care 31:173, 2008.
Nathan DM et al. "Management of hyperglycemia in Type 2 diabetes: a consensus algorithm for the initiation and adjustment of therapy." Diabetes Care 32:193, 2009.
Nathan et al. "Intensive diabetes treatment and cardiovascular disease in patients with Type 1 diabetes." New Eng. J. Med. 353:2643-2653, 2005.
Nathan, "Initial Management of Glycemia in Type 2 Diabetes Mellitus" N. Eng. J. Med., 2002, 347, 1342-9.
Nauck "Is glucagon-like peptide 1 an incretin hormone?" Diabetologia 42:373, 1999.
Nauck et al. "Glucagon-like peptide 1 inhibition of gastric emptying outweighs its insulinotropic effects in healthy humans." Am J Physiol 273 (Endocrinol Metabl 36):E981, 1997.
Nauck et al. "Reduced incretin effect in type 2 (non-insulin-dependent) diabetes." Diabetologia 29:46, 1986.
Nauck et al., Effects of glucagon-like peptide 1 on counterregulatory hormone responses, cognitive functions, and insulin secretion during hyperinsulinemic, stepped hypoglycemic clamp experiments in healthy volunteers. J Clin Endocrinol Metab., 87:1239-1246, 2002.
Nauck et al., Effects of subcutaneous glucagon-like peptide 1 (GLP-1 [7-36 amide]) in patients with NIDDM. Diabetologia, 39:1546-1553, 1996.
Nauck et al., Normalization of fasting hyperglycemia by exogenous GLP-1 (7-36 amide) in type 2 diabetic patients. Diabetologia, 36:741-744, 1993.
Nemmar et al., Passage of inhaled particles into the blood circulation in humans. Circulation pp. 411-414 (2002).
Newman, Principles of metered-dose inhaler design. Respiratory Care, vol. 50, No. 9, pp. 1177-1190 (2005).
Next Generation Inhaler Nears Market, Manufacturing Chemist, Cambridge Consultants, Polygon Media Ltd. (2006).
NHS Clinical Guidelines, "Type 1 diabetes diagnosis and mangement of type 1 diabetes in children and young people", National Collaborating Centre for Women's and Children's Health Commissioned by the National Institute for Clinical Excellence, Sep. 2004, p. 1-217.

(56) References Cited

OTHER PUBLICATIONS

Non-covalent interactions from UC Davis ChemWiki, pp. 1-5. Accessed by Examiner on Jul. 23, 2013 and related case U.S. Appl. No. 12/830,557.
Nystrom et al. "Effects of glucagon-like peptide-1 on endothelial function in type 2 diabetic patients with stable coronary artery disease." Am J Physiol Endocrinol Metabl 287:E1209, 2004.
Oberdorster et al., Correlation between particle size, in vivo particle persistence, and lung injury. Environ Health Perspect 102 Suppl 5, pp. 173-179 (1994).
Oberdorster et al.,Pulmonary effects of inhaled ultrafine particles. International Archives of Occupational and Environmental Health, vol. 74, pp. 1-8 (2001).
Okumura et al., Intratracheal delivery of insulin: absorption from solution and aerosol by rat lung. Int. J. Pharmaceuticals 88: 63-73 (1992).
O'Neill, Air pollution and inflammation in type 2 diabetes: a mechanism for susceptibility. Occup Environ Med. vol. 64, pp. 373-379 (2007).
Orgsoltab et al., Division of Organic Chemistry. Ohio Northern University. Nov. 24, 2009. Available from: <http://www.2.onu.edu/~b-meyers/organic_solvents.html>.
Oshima et al. "Comparison of half-disappearance times, distribution volumes and metabolic clearance rates of exogenous glucagon-like peptide 1 and glucagon in rats." Regulatory Peptides 21:85, 1988.
Ostrovsky, Gene. Mannkind Inhalation Insulin Going to FDA to Seek Approval [on-line]. MedGadget.com, posted on Mar. 17, 2009, Retrieved from the Internet: <URL:http://medgadget.com/2009/03mannkind_inhalation_insulin_going_to_fda_to_seek_approval.html>.
Owens et al. "Inhaled human insulin." Nature Reviews, Drug Discovery, vol. 5, No. 5, pp. 371-372, May 2006.
Owens et al. "Alternative routes of insulin delivery." Diabetic Medicine 20:886-898, 2003.
Ozyazgan et al. "Effect of glucagon-like peptide-1)7-36) and exendin-4 on the vascular reactivity in streptozotocin/nicotinamide-induced diabetic rats." Pharmacology 74:119, 2005.
Pacini P, Marino MT. Evaluation of endogenous and exogenous components to peripheral insulin concentration during administration of inhaled insulin. ADA 2010; Abstract 2094-PO.
Patton "Mechanisms of macromolecule absorption by the lungs." Advanced Drug Delivery Reviews 19:3, 1996.
Patton "Unlocking the opportunity of tight glycaemic control. Innovative delivery of insulin via the lung." Diabetes Obesity and Metabolism 7:S5, 2005.
Patton & Platz, Routes of Delivery: Case studies: pulmonary delivery of peptides and proteins for systemic action. Adv. Drug. Del. Rev. 8: 179-196 (1992).
Patton et al. "The lungs as a portal of entry for systemic drug delivery." Proc Am Thorac Soc 1:338, 2004.
Patton et al. "Clinical pharmacokinetics and pharmacodynamics of inhaled insulin." Clin Pharmacokinet 43:781-801, 2004.
Patton et al., "Inhaled Insulin", Advanced Drug Delivery Reviews, 35, Feb. 1999, p. 235-247.
Pearson et al., Systematically Initiating Insulin, supplemental to vol. 32, No. 1, 19S-28S, 2006.
Perera et al. "Absorption and Metabolic Effect of Inhaled Insulin." Diabetes Care, vol. 25, No. 12, Dec. 2002, p. 2276-2281.
Pesic, Inhaler delivers more drug to the deep lung, says Cambridge Consultants. in-Pharma Technologist.com, http://www/in-pharmatechnologist.com/content/view/print/344335, Dec. 1, 2010.
Petkowicz et al., "Hypoglycemic effect of liposome-entrapped insulin adminstered by various routes into normal rats", Pol. J. Pharmacol. Pharm. 41:299-304 (1989).
Petrucci R, Amin N, Lovertin P. et al. Pulmonary function tests remain similar in patients who received Technosphere® insulin and in patients currently receiving standard antidiabetic therapy. Diabetologia 2009; 52 (suppl 1).
Peyrot et al. "Resistance to insulin therapy among patients and providers." Diabetes Care 28:2673-2679, 2005.
Peyrot M, Rubin RR, Otterbach K. Effect of Technosphere® inhaled insulin on treatment satisfaction, glycemic control and quality of life. Diabetes 2006; 55:Abstract 423-P.
Pezron et al., Insulin aggregation and asymmetric transport across human bronchial epithelial cell monolayers (Calu-3). J. Pharmaceutical Sci. 91: 1135-1146 (2002).
Pfeiffer MA et al. Insulin secretion in diabetes mellitus. Am J Med 70:579-88, 1981.
Pfutzner et al., Abstract 812: Influence of small dose i.v.s.c. And pulmonary insulin treatment on grandial glucose control in patients with type 2 diabetes. Internet Article [Online] 2001, 37th Annual Meeting of the EASD, Glasgow, Sep. 9-13, 2001.
Pfutzner A et al. "Pulmonary insulin delivery by means of the Technosphere(TM) drug carrier mechanism." Expert Opin Drug Deliv 2:1097-1106, 2005.
Pfützner A et al. "Technosphere®/Insulin—a new approach for effective delivery of human insulin via the pulmonary route." Diab Tech Ther 4:589-594, 2002.
Pfützner A et al. "Lung distribution of radiolabeled Technosphere™/Insulin." Diabetes 52 Supplement, Jun. 2003, A107.
Pfützner A et al. Pilot study with Technosphere/PTH(1-34)—a new approach for effective pulmonary delivery of parathyroid hormone (1-34). Norm Metab Res 35:319-323, 2003.
Pfützner A et al. "Variability of insulin absorption after subcutaneous and pulmonary application in patients with type 2 diabetes." Diabetes 51 Supplement, Jun. 2002, A47-48.
Vilsboll T et al. "Reduced postprandial concentrations of intact biologically active glucagon-like peptide-1 in type 2 diabetic patients." Diabetes 50:609, 2001.
Vilsboll T et al. "Similar elimination rates of glucagon-like peptide-1 in obese type 2 diabetic patients and healthy subjects." J Clin Endocrinol Metab 88:220, 2003.
Volund "Conversion of insulin units to SI units." American Journal of Clinical Nutrition, Nov. 1993, 58(5), pp. 714-715.
Wachters-Hagedoorn et al. "The rate of intestinal glucose absorption is correlated with plasma glucose-dependent insulinotropic polypeptide concentrations in healthy men." J Nutr 136:1511, 2006.
Wang et al., Glucagon-like peptide-1 is a physiological incretin in rat. J. Clin. Invest., 95 : 417-421 (1995).
Wang et al., Glucagon-like peptide-1 regulates proliferation and apoptosis via activation of protein kinase B in pancreatic INS-1 beta cells. Diabetologia, 47:478-487, 2004.
Wareham et al., "Fasting Proinsulin Concentrations Predict the Development of Type 2 Diabetes", Diabetes Care, 1999, 22, 262-70.
Warren et al. "Postprandial versus prandial dosing of biphasic insulin aspart in elderly type 2 diabetes patients." Diabetes Res Clin Pract 66:23-29, 2004.
Waterhouse et al., "Comparatie assessment of a new breath-actuated inhaler in patients with reversible airways obstruction", Respiration 59:155-158 (1992).
WebMD (retrieved from http://www.webmd.com/pain-management/tc/pain-management-side-effects-of-pain-medicines on 0/21/12, 4 pages).
Wei et al. "Tissue-specific expression of the human receptor for glucagon-like peptide-1: brain and pancreatic forms have the same deduced amino acid sequence." FEBS Letters 358:219, 1995.
Weir et al. "Glucagonlike peptide 1 (7-37) actions on endocrine pancreas." Diabetes 38:338, 1989.
Weiss, SR et al. "Inhaled insulin provides improved glycemic control in patients with type 2 diabetes mellitus inadequately controlled with oral agents." Arch Intern Med 163:2277-2282, 2003.
Weissberger, "Mannkind: Overlooked Biotech with Excellent Prospects (Part V)," http://www.investorvillage.com/smbd.asp?mb=2885&mn=45817&pt=msg&mid=5021385 (posted on Jun. 19, 2008, accessed on Oct. 18, 2012).
West, Solid State Chemistry and its Applications. Wiley, New York, 358 (1998).
Wettergren A et al. "Truncated GLP-1 (proglucagon 78-107-Amide) inhibits gastric and pancreatic functions in man." Digestive Diseases and Sciences 38:665, 1993.
White JR et al. "Inhaled insulin: an overview." Clinical Diabetes 19:13-16, 2001.

(56) References Cited

OTHER PUBLICATIONS

Wigley et al., Insulin across respiratory mucosae by aerosol delivery. Diabetes 20(8): 552-556 (1971).
Willms B et al. "Gastric emptying, glucose responses, and insulin secretion after a liquid test meal: effects of exogenous glucagon-like peptide-1 (GLP-1)-(7-36) amide in type 2 (noninsulin-dependent) diabetic patients." J. Clin Endocrinol Metab 81:327, 1996.
Wilson BR et al. "Technospheres(TM) for pulmonary and nasal applications." Respiratory Drug Delivery VIII, 2002,p. 545.
Wilson et al., Spray-drying, a viable technosphere formulation process option to lyophilization, http://www.aapsj.org/abstracts/AM_2004/AAPS2004-002724.PDF, 1 page, 2004.
Witchert, Low molecular weight PLA: A suitable polymer for pulmonary administered microparticles. J. Microencapsulation, 10(2): 195-207 (1993).
Wright et al., Inhaled Insulin: Breathing new life into diabetes therapy. Nursing, vol. 37, No. 1, p. 46-48 (2007).
Wong et al. "From cradle to grave: pancreatic b-cell mass and glucagon-like peptide-1." Minerva Endocrinologica 31:107, 2006.
Wuts et al. "The Role of Protective Groups in Organic Synthesis," John Wiley, New York, 2nd Ed. 1991.
Yan et al., Analgesic action of microinjection of neurokinin A into the lateral reticular nucleus and nucleus raphe magnus in rats. Acta Physiologica Sinica, vol. 48, No. 5, pp. 493-496 (1996)—abstract.
Yang et al., Division and differentiation of natural antibody-producing cells in mouse spleen. PNAS, 104(11): 4542-4546 (2007).
Yoshida et al., Absorption of insulin delivered to rabbit trachea using aerosol dosage form. J. Pharm. Sci. 68(5): 670-671 (1979).
Yoshioka et al., "Serum proinsulin levels at fasting and after oral glucose load in patients with Type 2 (non-insulin dependent) diabetes mellitus", Diabetogia, 1988, 31, 355-60.
Yu W, Marino MT, Cassidy JP, et al. Insulin antibodies associated with Technosphere® insulin. ADA 2010; Abstract 216-OR.
Yusta B et al. "GLP-1 receptor activation improves b-cell function and survival following induction of endoplasmic reticulum stress." Cell Metabolism 4:391, 2006.
Zander et al., Effect of 6-week course of glucagon-like peptide 1 on glycaemic control, insulin sensitivity, and beta-cell function in type 2 diabetes: a parallel-group study. Lancet, 359:824-830, 2002.
Zethelius et al., "Proinsulin is an Independent Predictor of Coronary Heart Disease", Circulation 105:2153-2158 (2002).
Zimmerman, K., "Respiratory System: Fats, Function, and Diseases", <www.livescience.com/22616-respiratory-system.html>, copyright 2013, p. 1.
Zisser et al. "In Patients Using Technospere Insulin. Variation in PPG Stayed Within ADA-recommended Targets Despite Large Variations in Glucose Load." Mannkind Corporation (2010), ADA 2010; Poster 554.
Zisser H, Jovanovic L, Markova K, et al. Technosphere® insulin effectively controls postprandial glycemia in patients with type 2 diabetes mellitus. Diabetes Technology and Therapeutics 2012;14:997-1001.
Exubera package insert, p. 1, 2008.
Fadl et al., Effects of MDI spray angle on aerosol penetration efficiency through an oral airway cast. Journal of Aerosol Science, vol. 38, No. 8, pp. 853-864 (2007).
Falsone et al., The Biginelli dihydropyrimidone synthesis using polyphosphate ester as a mild and efficient cyclocondensation/dehydration reagent. Institute of Chemistry, Organic and Bioorganic Chemistry, Karl-Franzens-University, pp. 122-134 (2001).
Farr, S.J. et al. Pulmonary insulin administration using the AERx® system:physiological and physiochemical factors influencing insulin effectiveness in healthy fasting subjects. Diabetes Tech. Ther. 2:185-197, 2000.
Fehmann et al. "Cell and molecular biology of the incretin hormones glucagon-like peptide-1 and glucose-dependent insulin releasing polypeptide." Endocrine Reviews 16:390, 1995.
Ferrin et al, Pulmonary retention of ultrafine and fine particles in rats. Am. J. Repir. Cell Mol. Biol., pp. 535-542 (1992).
Festa et al., "LDL particle size in relation to insulin, proinsulin, and insulin sensitivity" Diabetes Care, 22 (10):1688-1693 (1999).
Forst et al., "Metabolic Effects of Mealtime Insulin Lispro in Comparison to Glibenclamide in Early Type 2 Diabetes", Exp. Clin. Endocrinol. Diabetes, 2003, 111, 97-103.
Fritsche et al. "Glimepiride Combined with Morning Insulin Glargine, Bedtime Neutral Protamine Hagedorm Insulin, or Bedtime Insulin Glargine in Patients with Type 2 Diabetes." American College of Physicians 2003.
Galinsky et al., A synthesis of diketopiperazine's using polyphosphoric acid. Journal of the American Pharmaceutical Association, vol. 46, No. 7, pp. 391-393 (1957).
Garber, "Premixed insulin analogues for the treatment of diabetes mellitus", Drugs, 66(1):31-49 (2006).
Garg et al. "Improved glycemic control without an increase in severe hypoglycemic episodes in intensively treated patients with type 1 diabetes receiving morning, evening, or split dose insulin glargine." Diabetes Research and Clinical Practice 66 (2004) 49-56.
Garg SK, Kelly W, Freson B, et al. Treat-to-target Technosphere® insulin in patients with type 1 diabetes. ADA 2011; Abstract 941-P.
Gates BJ "Update on advances in alternative insulin therapy." Advances in Pharmacy 1:159-168, 2003.
Glucagon for Injection (1999) glucagon for injection (rDNA origin), pp. 1-7.
Glucophage Product Insert. Jan. 2009.
Glucotrol Product Insert. Sep. 2006.
Gnudi L, Lorber D, Rosenstock J, et al. Basal/bolus with prandial inhaled Technosphere® insulin (TI) plus insulin glargine qd vs biaspart 70/30 insulin bid in type T2 diabetes mellitus inadequately controlled on insulin with/without oral agents. Diabetologia 2009; 52 (suppl 1).
Goke et al., Exendin-4 is a high potency agonist and truncated exendin-(9-39)-amide an antagonist at the glucagon-like like peptide 1-(7-36)-amide receptor of insulin-secreting beta-cells. J. Biol. Chem. 268(26):19650-19655 (1993).
Golpon et al. "Vasorelaxant effect of glucagon-like peptide-(7-36) amide and amylin on the pulmonary circulation of the rat." Regulatory Peptides 102:81, 2001.
Gonzalez et al., Actualizacion del tratamiento farmacologico de la diabetes mellitus tipo 2. Del Sistema Nacional de Salud. vol. 32, No. 1, pp. 3-16 (2008)—full article in Spanish with English abstract.
Gotfried M, Cassidy JP, Marino MT, et al. Lung deposition and absorption of insulin from Technosphere® insulin. Diabetologia 2009; 52 (suppl 1).
Grant et al "Both insulin sensitivity and maximal glucose elimination rate are reduced in type 2 diabetes." Presented at the American Diabetes Association 65th Scientific Sessions, Jun. 2005, abstract 2202-PO.
Grant et al. "The distribution of 14C-labeled particles following intra-tracheal liquid installation in the Sprague-Dawley rat." Presented at the American Diabetes Association 64th Scientific Sessions, Jun. 2004, abstract 461-P.
Grant M, Harris E, Leone-Bay A, Rousseau K. Technosphere®/insulin: Method of action. Diabetes Technology Meeting 2008; Poster.
Grant ML, Greene S, Stowell GW, et al. Mimicking endogenous peptide secretion by inhalation APS 2009; poster.
Greene et al. "Effects of GLP-1 Technosphere(TM) powder: administered by pulmonary insufflation in male obese Zucker diabetic fat (ZDF) rats." Diabetes Technology Meeting, San Francisco, Oct. 2007.
Greene et al., Greene's protective groups in organic synthesis. 4th ed., pp. 781-783 (2007).
Gupta et al. "Contemporary Approaches in Aerosolized Drug Delivery to the Lung." J. Controlled Research, 17:129-148, 1991.
Gurrieri et al., Thermal condensation of some alpha-aminoacids with phatalic acid. Thermochimica Acta, 7 (1973) 231-239.
Gutniak et al. "Antidiabetogenic action of glucagon-like peptide-1 related to administration relative to meal intake in subjects with type 2 diabetes." J Int Med 250:81, 2001.
Gutniak et al. "Antidiabetogenic effect of glucagon-like peptide-1 (7-36)amide in normal subjects and patients with diabetes mellitus." NEJM 326:1316, 1992.

(56) References Cited

OTHER PUBLICATIONS

Gutniak et al. "GLP-1 tablet in type 2 diabetes in fasting and postprandial conditions." Diabetes Care 20:1874, 1997.
Gutniak et al. "Potential therapeutic levels of glucagon-like peptide I achieved in humans by a buccal tablet." Diabetes Care 19:843, 1996.
Gutniak et al. "Subcutaneious injection of the incretin hormone glucagon-like peptide 1 abolishes postprandial glycemia in NIDDM." Diabetes Care 17:1039, 1994.
Guyton et al., "Acute Control of Llocal Blood Flow", Textbook of Medical Physiology, Chapter 17, 10th Edition, W.B. Saunders Company, pp. 176-177, 2000.
Gyore et al., Thermal Analysis, vol. 2—Proceedding Fourth ICTA Budapest 1974; 387-394.
Haak "New developments in the treatment of type 1 diabetes mellitus." Exp Clin Endocrinol Diabetes 107:Suppl 3: S108, 1999.
Haffner et al., "Proinsulin and insulin concentrations I relation to carotid wall thickness", Strock 29:1498-1503 (1998).
Hagedorn et al. "Protamine Insulin", JAMA, 106:177-180 (1936).
Haino, Takeharu et al. "On-beads Screening of Solid-Attached Diketopiperzines for Calix[5]Arene-Based Receptor." Tetrahedron Letters, 40(20), 3889-3892, 2003.
Halozyme Press Release. Jun. 6, 2009.
Hanley et al., "Cross-sectional and prospective associations between proinsulin and cardovascular disease risk factors in a population experiencing rapid cultural transition" Diabetes Care 24(7): 1240-1247 (2001).
Harsch IA "Inhaled insulins. Their potential in the treatment of diabetes mellitus." Traat. Endicrinol 4:131-138, 2005.
Hassan et al. "A Randomized, Controlled Trial Comparing Twice-a-Day Insulin Glargine Mixed with Rapid-Acting Insulin Analogs Versus Standard Neutral Protamine Hagedorn (NPH) Therapy in Newly Diagnosed Type 1 Diabetes." Pediatrics, 121(3), e466-e472, 2008.
Hassan et al. "In vivo dynamic distribution of 1311-glucagon0like peptide-1 (7-36) amide in the rat studied by gamma camera." Nucl Med Biol 26:413, 1999.
Hausmann et al. "Inhaled insulin as adjunctive therapy in subjects with type 2 diabetes failing oral agents: a controlled proof of concept study." Diabetes Obesity and Metabolism 8:574, 2006.
Hayasaka et al. "Proliferation of type II pneumocytes and alteration in their apical surface membrane antigenicity in pulmonary sarcoidosis." Chest 116:477, 1999.
Cheatham et al. "Prandial Technospheree/Insulin inhalation provides significantly better control of meal-related glucose excursions than prandial subcutaneous insulin." Presented at the Diabetes Technology Society meeting, Oct. 2004.
Chelikani et al., Intravenous infusion of glucagon-like peptide-1 potently inhibits food intake, sham feeding, and gastric emptying in rats. Am J Physiol. Regul. Integr. Comp. Physiol., 288(6):R1695-706, 2005.
Chemical Abstracts, vol. No. 114(22), Abstract No. 214519x (1990).
Chemicaland21.com. Solvents. Dec. 12, 2008. Available from: <http://web.archive.org/web20081212035748/http://www.chemicalland21.com/info/SOLVENTS.htm.
Chow et al., Particle Engineering for Pulmonary Drug Delivery. Pharmaceutical Research, vol. 24, No. 3, pp. 411-437 (2007).
Clee et al. Nature Genetics 38:688-693, 2006.
Cobble "Initiating and Intensifying Insulin Therapy for Type 2 Diabetes: Why, When, and How." Am J Ther. Jan. 8, 2009.
Coffey et al. "Valuing heath-related quality of life in diabetes." Diabetes Care 25:2238, 2002.
Colagiuri et al., Are lower fasting plasma glucose levels at diagnosis of type 2 diabetes associated with improved outcomes? Diabetes Care, vol. 25, pp. 1410-1417 (2002).
Combettes and Kargar, C, Newly Approved and Promising Antidiabetic Agents. Therapie, Jul.-Aug. 2007: 62 (4): 293-310.
Coors et al., Polysorbate 80 in medical products and nonimmunologic anaphylactoid reactions. Ann. Allergy Astha Immunol., 95(6): 593-599 (2005).
Costello et al., "Zinc inhibition of mitochondrial aconitase and its importance in citrate metabolism in prostate epithelial cells", Journ. Biol. Chem. 272(46):28875-28881 (1997).
Cricket TM Single-Use Inhalers [on-line]. Mannkind Technologies Website, posted in 2011, [retrieved on Jul. 30, 2012]. Retrieved from the Internet. <URL:mannkindtechnologies,com/DeviceTechnology/CricketSingleUselnhalers.aspx>.
Crosby, J. "Dog Normals", <http://vetmedicine.about.com/od/diseasesconditionsfaqs/tp/TP_dogfacts.htm>, copyright 2013.
Cruetzfeldt et al. "Glucagonostatic actions and reduction of fasting hyerglycemia by exogenous glucagon-like peptide i(7-36) amide in type 1 diabetic patients." Diabetes Care 19:580, 1996.
D'Alessio et al., Elimination of the action of glucagon-like peptide 1 causes an impairment of glucose tolerance after nutrient ingestion by healthy baboons. J. Clin. Invest., 97:133-38 (1996).
Database adisinsight, "Gucagon-like peptide-1 inhalation-Mannkind Corporation", Database accession No. 2009:1048 Abstract.
Davis "Postprandial Physiology and the Pathogenesis of Type 2 Diabetes Mellitus." Insulin, vol. 3, Apr. 1, 2008, pp. 132-140.
De Heer et al. "Sulfonylurea compounds uncouple the glucose dependence of the insulinotropic effect of glucagon-like like peptide-1." Diabetes 56:438, 2007.
Deacon "Therapeutic strategies based on glucagon-like peptide 1." Diabetes. Sep;53(9):2181-9, 2004.
Deacon et al., "Glucagon-like peptide 1 undergoes differential tissue-specific metabolism in the anesthetized pig", Am. J. Physiol. 271 (Endocrino. Metab. 34): E458-E464, 1996.
Decode study group. "Glucose tolerance and mortality: comparison of WHO and American Diabetes Association diagnostic criteria. " Lancet. Aug. 21, 1999;354(9179):617-21.
DedicatedPhase, "Preclinical Trials and Research", <http://www.dedicatedphase1.com/preclinical-research.html>, copyright 2006-2011, p. 1.
Definition of analog from http://cancerweb.ncl.ac.uk/omd/about.html, pp. 1-5.
Del Prato S "Unlocking the opportunity of tight glycemic control" Diabetes Obesity and Metabolism 7:S1-S4, 2005.
Delgado-Aros et al. "Effect of GLP-1 on gastric volume, emptying, maximum vol. ingested and postprandial symptoms in humans." Am J Physiol Gastrointest Liver Physiol 282:G424, 2002.
Diabetes: Counting Garbs if You Use Insulin, WedMD, http://diabetes.webmd.com/carbohydrate-counting-for-people-who-use-insulin#m Oct. 1, 2010.
Diez et al. "Inhaled insulin—a new therapeutic option in the treatment of diabetes mellitus" Expert Opin. Pharmacother., 2003, 4, 191-200.
Dorwald, F.A. Side reactions in organic synthesis. Wiley, (2005).
Doyle et al. "Glucagon-like peptide-1." Recent Prog Horm Res. 2001;56:377-99.
Dreamboat TM Reusable Inhalers [on-line]. Mannkind Technologies Website, posted in 2011, Retrieved from the Internet: <URL: mannkindtechnologies.com/Device Technology/Dream Boat Reuseable Inhalers.aspx>.
Drucker "Development of glucagon-like peptide-1-based pharmaceuticals as therapeutic agents for the treatment of diabetes." Curr Pharma Design 7:1399, 2001.
Drucker et al., "The incretin system:glucagon-like peptide-1 receptor agonists and dipeptidyl peptidase-4 inhibitors in type 2 diabetes", www.thelancet.com, vol. 368, pp. 1696-1705, Nov. 11, 2006.
Drug Delivery, Easing the drug delivery route, Jun. 2006, Pharmaceutical & Medical Packaging News, Canon Communications.
Dungan et al., Glucagon-like peptide 1-based therapies for type 2 diabetes: a focus on exntadtide. Clinical Diabetes, 23: 56-62 (2005).
Dunn, "Zinc-ligand interactions modulate assembly and stability of the insulin hexamer", Biometals, 18(4):295-303 (2005).
Edelman "Type II Diabetes Mellitus." Adv Int Med, 43:449-500, 1998.
Edited by Fukushima, Masanori, "Arterial Sclerosis," Merck Manual 17th, Japanese Edition, NIKKEI BP Corp., p. 1659-1663, 1999.
Edwards CMB et al. "Cardiovascular and pancreatic endocrine response to glucagon-like peptide-1(7-36) amide in the conscious calf." Exp Physiol 82:709, 1997.

(56) References Cited

OTHER PUBLICATIONS

Edwards CMB et al. "Subcutaneous glucagon-like peptide-1(7-36) amide is insulinotropic and can cause hypoglycaemia in fasted healthy subjects." Clinical Science 96:719, 1998.
Edwards et al., Recent advances in pulmonary drug delivery using large, porous inhaled particles. Journal of Applied Physiology, pp. 379-385 (1998).
Eggers et al., Molecular confinement influences protein structure and enhances thermal protein stability. Protein Sci., 10:250-261 (2001).
Ehlers et al. "Recombinant glucagon-like peptide-1 (7-36 amide) lowers fasting serum glucose in a broad spectrum of patients with type 2 diabetes." Horm Metab Res 35:611, 2003.
Eissele et al., Rat gastric somatostatin and gastrin relase: interactions of exendin-4 and truncated glucagon-like peptide-1 (GLP-1) amide. Life Sci., 55(8):629-634 (1994).
Elliot et al., Parenteral absorption of insulin from the lung in diabetic children. Austr. Paediatr. J. 23: 293-297 (1987).
Elrick et al. "Plasma insulin response to oral and intravenous glucose administration." J Clin Endocr 24:1076, 1964.
Engelgau MM "Screening for type 2 diabetes." Diabetes Care 23:1563-1580, 2000.
Engwerda et al., Improved pharmackinetic and pharmacodynamic profile of rapid-acting insulin using needle-free jet injection technology. Diabetes Care, vol. 34, Aug. 2011, pp. 1804-1808.
Erlanger et al., Phosphorous pentoxide as a reagent in peptide synthesis. College of Physicians and Surgeons—Columbia Univeristy, vol. 26, pp. 2534-2536 (1960).
Exubera indications, dosage, storage, stability. Http://www.rxlist.com/cgi/generic4/exubera_ids.htm, 2008.
Standl et al. "Good Glycemic Control With Flexibility in Timing of Basal Insulin Supply." Diabetes Care, vol. 28, No. 2, Feb. 2005.
Stanley et al. "Gastrointestinal satiety signals III. Glucagon-like peptide 1, oxyntomodulin, peptide YY and pacretic peptide." Am J Physiol Gastrointest Liver Physiol 286:G693, 2004.
Steinberg et al. "A new approach to the safety assessment of pharmaceutical excipients." Reg Toxicol Pharmacol 24:149, 1996.
Steiner et al. "A novel glucagon delivery system for the management of hyperinsulinemia." Diabetes 49 Supplement 1, Abstract 1545-PO, A368, 2000.
Steiner et al. "Bioavailability and pharmacokinetic properties of inhaled dry powder Technosphere®/Insulin." Diabetes 49 Supplement, May 2000, A126.
Steiner et al. "Technosphere®, a novel drug delivery system for oral administration of calcitonin." Pharmaceutical Res 11:S299, 1994.
Steiner et al. Technosphere(TM)/Insulin—proof of concept study with a new insulin formulation for pulmonary delivery. Exp Clin Endocrinol Diabetes, 110:17-21, 2002.
Steiner, K. et al. "The relative importance of first- and second-phase insulin secretion in countering the action of glucagon on glucose turnover in the conscious dog." Diabetes 31:964-972, 1982.
Steiner S, Rave K, Heise T, et al. Pharmacokinetic properties and bioavailablility of inhaled drug powder Technosphere™/insulin. Exp Clin Endocrinol Diabetes 2000; 108:S161.
Steiner S, Rave K, Heise T, et al. Technosphere™/insulin: Bioavailability and pharmacokinetic properties in healthy volunteers. Diabetologia 2000;43:Abstract 511-P.
Steiner SS, Burrell BB, Feldstein R, et al. Pulmonary delivery of Technosphere™/insulin: Increased bioefficacy and bioavailability in clinical trials using the PDC Medtone™ inhaler. Proceed Int'l Symp Control Rel Bioact Mater 2000; 27: 1000-1001.
Stowell et al. "Development of GLP-1 Technosphere(TM) powder: an inhaled GLP-1 product" Diabetes Technology Meeting, San Francisco, Oct. 2007.
Strack "Inhaled Human Insulin." Drugs of Today 2006, 42 (4): 207-221.
Sturis et al., GLP-1 deriative liraglutide in rats with beta-cell deficiences: influence of metabolic state on beta-cell mass dynamics. British Journal of Pharmacology, 140 : 123-132 (2003).
Svartengren et al., Added External Resistance Reduces Oropharyngeal Deposition and Increases Lung Deposition of Aerosol Particles in Asthmatics. Am. J. Respir. Crit Care Med., vol. 152, pp. 32-37, 1995.
Sympatecs. Dry Dispersion for Laser Diffraction and Image Analysis, 2011. XP-002586530.
Tack Cees J. et al., Forced Titration to Different Doses of Technosphere Insulin Demonstrates Reduction in Postprandial Glucose Excursions and Hemoglobin A1c in Patients with Type 2 Diabetes. Journal of Diabetes Science and Technology, vol. 2, Issue 1, pp. 47-57, Jan. 2008.
Tack CJ, Boss AH, Baughman RA, et al. A randomized, double blind, placebo controlled study of the forced titration of prandial Technosphere®/Insulin in patients with type 2 diabetes mellitus. Diabetes 2006;55:Abstract 428-P.
Tack CJ, Christov V, deGalan BE, et al. Randomized forced titration to different doses of Technosphere® insulin demonstrates reduction in postprandial glucose excursions and hemoglobin A1c in patients with type 2 diabetes. J Diabetes Sci Technol 2008;2:47-57.
Tang-Christensen et al. "Central administration of GLP-1-(7-36) amide inhibits food and water intake in rats." Am J Physiol 271 (Regulatory Integrative Comp Physiol 40):R848, 1996.
Taylor et al. "Aerosols for macromolecule delivery. Design challenges and solutions." Am J Drug Deliv 2:143-155, 2004.
Teeter et al. "Dissociation of lung function changes with humoral immunity during inhaled human insulin therapy." Am J Resp Crit Care Med 173:1194, 2006.
Telko et al., Dry Powder Inhaler Formulation. Respiratory Care, Sep. 2005, vol. 50, No. 9, 1209-1227.
The American Diabetes Association "Insulin Administration" Diabetes Care, vol. 27, Supplement 1, S106-S109 (2004).
The Decode study group. "Glucose tolerance and mortality: comparison of WHO and American Diabetes Association diagnostic criteria." Lancet. Aug. 21, 1999;354(9179):617-21.
The Lancet. 1989, vol. 333, p. 1235-1236.
Thorens "Expression cloning of the pancreatic b-cell receptor for the gluco-incretin hormone glucagon-like peptide-1." PNAS 89:8641, 1992.
Thorens B et al. "Cloning and function expression of the human islet GLP-1 receptor: demonstration that exendin-4 is an agonist and exendin-(9-39) an antagonist of the receptor." Diabetes 42:1678, 1993.
Todd et al. "Glucagon-like peptide-1 (GLP-1: a trial of treatment in on-insulin-dependent diabetes mellitus." Eur J Clin Invest 27:533, 1997.
Todd et al. Subcutaneous glucagon-like peptide-1 improves postprandial glucaemic control over a 3-week period in patients with early type 2 diabetes. Clinical Science 95:325, 1998.
Toft-Nielson et al. "Determinants of the effectiveness of glucagon-like peptide-1 in type 2 diabetes." J Clin Endocrinol Metab 86:3853, 2001.
Toft-Nielson et al. "Exaggerated secretion of glucagon-like peptide-1 (GLP-1) could cause reactive hypoglcaemia." Diabetologia 41:1180, 1998.
Toft-Nielson et al. "The effect of glucagon-like peptide-1 (GLP-1) on glucose elimination in healthy subjects depends on the pancreatic glucoregulatory hormones." Diabetes 45:552, 1996.
Tornusciolo D.R. et al., Biotechniques 19(5):800-805, 1995. Simultaneous detection of TDT-mediated dUTP-biotin nick end-labeling (TUNEL)-positive cells and multiple immunohistochemical markers in single tissue sections.
Triantafyllidis et al., Structural, compositional and acidic characteristics of nanosized amorphous or partially crystalline ZSM-5 zeolite based materials. Microporous and Mesoporous Materials, 75:89-100 (2004).
Tu N, Kramer DA, Baughman RA. Inhaled Technosphere® Insulin improves glycemic control without weight gain. Diabetes 2007;56:Abstract 471-P.
Tuley et al., Experimental observations of dry powder inhaler dose fluidisation. International Journal of Pharmaceutics, 358, pp. 238-247 (2007).

(56) References Cited

OTHER PUBLICATIONS

Utah Valley University. Saponification. © 2009. Available from: <http://science.uvu.edu/ochem/index.php/alphabetical/s-t/saponification/printpage/>.

Vaczek, Accelerating drug delivery firms exploring new drug-delivery routes and devices intently awaiting the commercial launch of Exubera. Pharmaceutical & Medical Packaging News, vol. 14, No. 6 (2006).

Vahl et al. "Effects of GLP-1-(7-36)NH2, GLP-1-(7-37), and GLP-1-(9-36)NH2 on intravenous glucose tolerance and glucose-induced insulin secretion in healthy humans." J Clin Endocrinol Metabol 88:1772, 2003.

Van Alfen-Van Der Velden et al. "Successful treatment of severe subcutaneou insulin resistance with inhaled insulin therapy", Pediatric Diabetes 2010: 11:380-382.

Vara E et al. "Glucagon-like peptide-1 (7-36) amide stimulates surfactant secretion in human type II pneumocytes." Am J Resp Crit Care Med 163:841, 2001.

Vella A et al. "Effect of glucagon-like peptide 1(7-36) amide on glucose effectiveness and insulin action in people with type 2 diabetes." Diabetes 49:611, 2000.

Vella A et al. "The gastrointestinal tract and glucose tolerance." Curr Opin Clin Nutr Metab Care 7:479, 2004.

Vendrame et al. "Prediabetes: prediction and prevention trials." Endocrinol Metab Clin N Am, 2004, vol. 33, pp. 75-92.

Verdich C, et al., A meta-analysis of the effect of glucagon-like peptide-1 (7-36) amide on ad libitum energy intake in humans. J Clin Endocrinol Metab., 86:4382-4389, 2001.

Vilsboll et al. "Reduced postprandial concentrations of intact biologically active glucagon-like peptide-1 in type 2 diabetic patients." Diabetes 50:609, 2001.

Vilsboll et al. "Similar elimination rates of glucagon-like peptide-1 in obese type 2 diabetic patients and healthy subjects." J Clin Endocrinol Metab 88:220, 2003.

Vilsboll et al., "Evaluation of β-Cell Secretary Capacity Using Glucagon-Like Peptide 1", Diabetes Care, vol. 23, No. 6, pp. 807-812, Jun. 2000.

Vilsboll et al., "Incretin secretion in Relation to Meal Size and Body Weight in Healthy Subjects and People with Type 1 and Type 2 diabetes Mellitus", The Journal of Clinical Endrocronology & Metabolism, vol. 88, No. 6, pp. 2706-2713, 2003.

Amodeo et al., Pain peptides. Solution structure of orphanin FQ2. FEBS Letters, vol. 473, Issue 2, pp. 157-160 (2000).

Hazard Prevention and Control in the Work Environment: Airborne Dust WHO/SDE/OEH/99. 14 Chapter 1—Dust: Definitions and Concepts [retrieved from internet by Examiner in European case on Sep. 22, 2015]. <URL: http://www.who.int/occupational_health/publications/airdust/en/> published on Oct. 29, 2004 as per Wayback Machine.

Owens et al., Blood glucose self-monitoring in type 1 and type 2 diabetes: reaching a multidisciplinary consensus. Diabetes and Primary Care, vol. 6, No. 1, pp. 8-16 (2004).

Vanderah et al., FE200041 (D-Phe-D-Phe-D-Nle-D-Arg-NH2): A peripheral efficacious k opioid agonist with unprecedented selectivity. The Journal of Pharmacology and Experimental Therapeutics, vol. 310, No. 1, pp. 326-333 (2004).

* cited by examiner

METHODS AND COMPOSITIONS FOR TREATING PAIN

CROSS REFERENCE TO RELATED APPLICATIONS

This application is a 371 of PCT/US2012/061749, filed Oct. 24, 2012, which claims benefit under 35 U.S.C. §119(e) from U.S. Provisional Patent Application Ser. No. 61/550,860, filed Oct. 24, 2011, the contents of which are incorporated herein by reference in their entirety.

TECHNICAL FIELD

Methods and compositions for treating pain, such as inhaled opioid compositions, are disclosed. Exemplary compositions can comprise dry powders for pulmonary inhalation.

BACKGROUND

Acute pain is characterized by a sudden onset and relatively short duration, and is generally treated with opioid analgesics like morphine. Morphine and similar opioid analgesics suppress the perception of pain by reducing the number of pain sensations sent by the nervous system and the brain's reaction to those pain signals. Current opioid therapy using morphine and like compounds are effective to treat pain but the side effects they produce such as addiction, somnolence, tolerance, respiratory depression, and constipation limit their clinical use.

In addition, opiates presently used in therapy such as morphine are alkaloid compounds isolated from natural sources such as the opium poppy. There are also semi-synthetic substances derived from the opium poppy, as well as and are chemically synthesized compounds including anilidopiperidines, phenylpiperidines, diphenylpropylamine derivatives, morphinan derivatives, and benzomorphan derivatives.

Opioid analgesics relieve pain and inhibit nociceptive signaling by binding to Opioid receptors on cells in the central and peripheral nervous systems and the gastrointestinal tract. The analgesic effects of opioids are due to decreased perception of pain, decreased reaction to pain and increased resistance to pain. Known opioid receptors include mu (μ), delta (δ) and kappa (κ). Opioid receptor agonists, including morphine, the enkephalins, and the dynorphins, bind to these receptors. The most commonly studied opioid receptor modulated is the μ opioid receptor. However, kappa opioid receptor agonists have been shown to be effective and potent analgesics, but their usefulness in humans is limited due to their psychomimetic and dysphoric effects. Delta (δ) opioid receptor agonists are known to produce analgesic effects with lesser magnitude side effects than μ analgesics. For example, delta analgesics induce less tolerance and physical dependence, do not depress respiration, and cause few or no adverse gastrointestinal effects, including constipation. However, delta opioid receptor agonists can produce seizures. Moreover, in some animal experiments, delta opioid agonists can produce an effective and potent analgesic effect when administered intrathecally or by intracerebroventricular injection. However; these routes of administration are not practical for treating patients.

Therefore, there is still a need in the medical art to develop new treatments for pain which would facilitate patient therapy and reduce or eliminate unwanted side effects. Additionally, there is a need for the identification and development of new compounds and compositions that do not cross the blood-brain barrier and effectively alleviate pain without activating opioid receptors in the central nervous system.

SUMMARY

Methods and compositions for treating pain are disclosed. The compositions can comprise dry powders comprising microparticles including a diketopiperazine and an active agent. In an embodiment the microparticles are administered in compositions for pulmonary inhalation using a dry powder inhalation system and comprise one or more peptide analgesics or derivatives thereof delivered. In embodiments the diketopiperazine is an N-substituted-3,6-aminoalkyl-2,5-diketopiperazine. In certain embodiments the active agent can be a peptide, or the like.

In embodiments the diketopiperazine can be 3,6-bis(N-X-4-aminobutyl)-2,5-diketopiperazine wherein X is fumaryl, succinyl, glutaryl, maleyl, malonyl, oxalyl, or a pharmaceutically acceptable salt thereof, such as 3,6-bis(N-fumaryl-4-aminobutyl)-2,5-diketopiperazine, or 3,6-bis(N-fumaryl-4-aminobutyl)-2,5-diketopiperazine disodium salt.

An embodiment includes an inhalable, analgesic composition comprising microparticles of a diketopiperazine and a peptide comprising less than 20 amino acids; wherein said composition is effective in relieving pain. In an embodiment the peptide comprises one or more of: glycine, alanine, valine, methionine, phenylalanine, serine, threonine, asparagine, glutamine, cysteine, lysine, histidine, aspartic acid, glutamic acid, leucine, isoleucine, norleucine, tyrosine, serine, proline, and tryptophan. In some embodiments, the peptide comprises at least 3 amino acids, wherein each of those 3 amino acids is; arginine, phenylalanine, leucine, isoleucine, norleucine, tyrosine, serine, proline, or tryptophan. In embodiments the peptide is greater than 0.25% of the weight of a dry powder composition.

In certain embodiments the peptide can comprises an amino acid sequence of from three to eight amino acids in length. In embodiments the peptide can comprise one of the following sequences: (D)Phe-(D)Phe-(D)Ile-(D)Arg-$NH_2$ (SEQ ID NO: 1), (D)Phe-(D)Phe-(D)Nle-(D)Arg-$NH_2$ (SEQ ID NO: 2), Trp-(D)Pro-Ser-Phe-$NH_2$ (SEQ ID NO: 3), Trp-(D)Ser-Ser-Phe-$NH_2$ (SEQ ID NO: 4); Dmt-D-Arg-Phe-Lys-$NH_2$ (SEQ ID NO: 5), Ac-His-(D)Phe-Arg-(D)Trp-Gly-$NH_2$ (SEQ ID NO: 6), and Ac-Nle-Gln-His-(D)Phe-Arg-(D)Trp-Gly-$NH_2$ (SEQ ID NO:7).

In embodiments the peptide can be an opioid receptor agonist. In embodiments the peptide can bind to the μ opioid receptor, δ opioid receptor, or κ opioid receptors, or combinations of receptors thereof of cells in the central or peripheral nervous systems.

In embodiments the peptide can be an alpha-melanocyte stimulating hormone (MSH) receptor agonist.

In embodiments the composition can be a dry powder for inhalation and comprise microparticles having a volumetric mean geometric diameter less than 5.8 μm in diameter.

Certain embodiments comprise a method for treating pain, comprising administering to a subject in need of treatment a therapeutically effective amount of a composition described herein using a dry powder drug delivery system comprising a dry powder inhaler configured with a container to hold said analgesic composition in a containment configuration and in a dosing configuration. In embodiments the analgesic composition can be a dry powder comprising a peptide that binds to an opioid receptor.

BRIEF DESCRIPTION OF THE DRAWINGS

FIG. 4A shows data from ambulatory observations made and FIG. 4B shows data from respiratory measurements made from treated animals versus controls.

DETAILED DESCRIPTION

Figure 1:
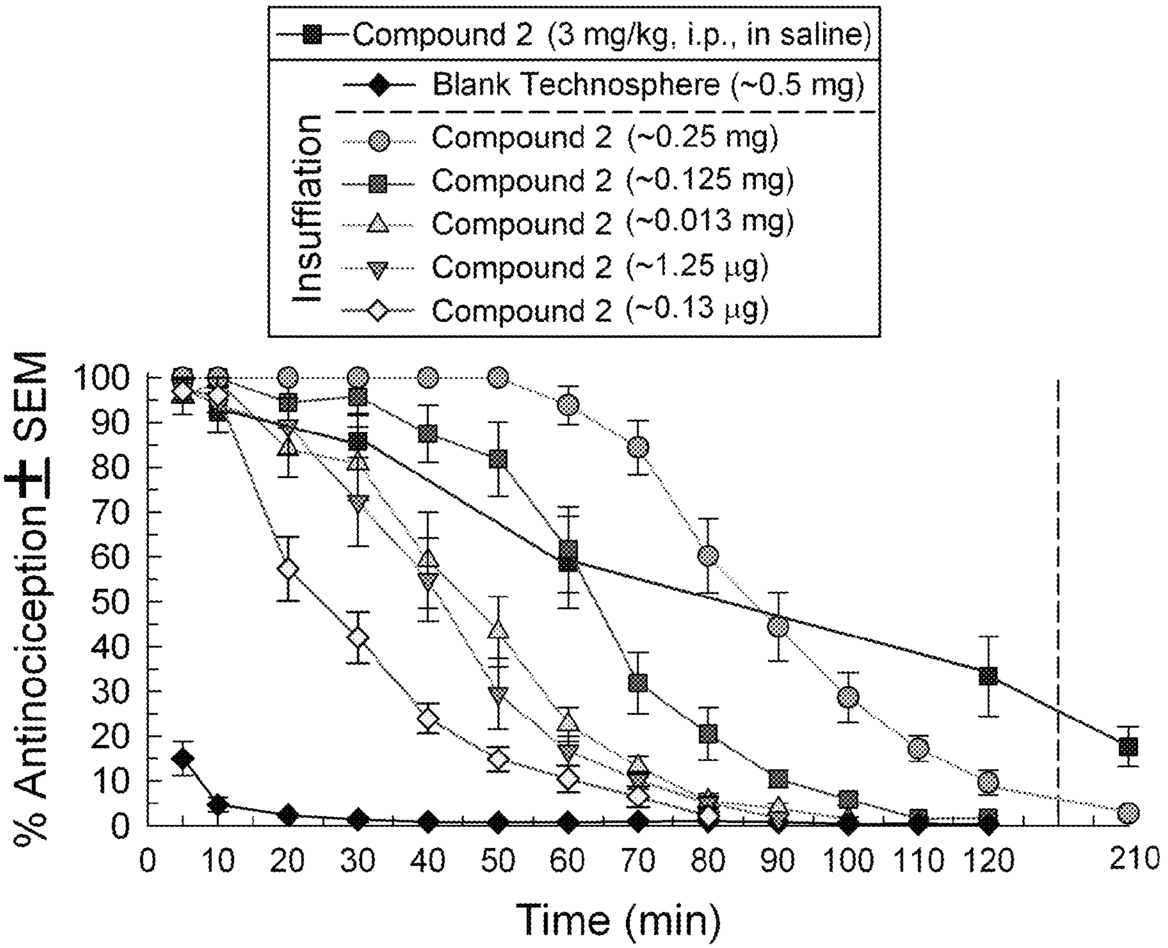
FIG. 1 depicts a graph showing data from 55° C. warm-water tail withdrawal ("Tail-flick") experiments in mice treated with an inhalable dry powder formulation comprising an analgesic peptide at various concentrations administered by insufflation and compared to a control intraperitoneal injection of the peptide and a placebo dry powder formulation.

Disclosed are methods and compositions for treating pain that facilitate delivery of the pain medication while reducing unwanted side effects, such as, for example, addiction, somnolence, tolerance, respiratory depression, and constipation, and the like.

In embodiments the pain to be treated can be, for example, a peripheral neuropathy, a central neuropathy, a traumatic abnormality, a cerebral vascular accident, postoperative pain, dental pain, direct trauma, infection, HIV infection, small pox infection, herpes infection, toxic exposure, exposure to arsenic, exposure to lead, cancer, invasive cancer, congenital defect, phantom limb pain, encephalitis, rheumatoid arthritis, fibromyalgias, spinal root lesions, spinal root impingement, back pain, multiple sclerosis, chronic pain, fibrous tissue pain, muscle pain, tendon pain, ligament pain, pain associated with diarrhea, irritable bowel syndrome, abdominal pain, chronic fatigue syndrome, and spasms.

In embodiments, the methods and compositions can be used for the treatment of pain modulated through cell receptors. In embodiments disclosed herein the methods and compositions can comprise, active agents such as, for example, receptor agonists, antagonists, or the like. In embodiments disclosed herein the methods and compositions can comprise, for example, opioid receptor agonists and/or antagonists, alpha-MSH receptor agonists and/or antagonists, and the like, and can be provided to a subject as the active agents for treating pain. In certain embodiments the active agents act directly or indirectly upon other receptor agonists.

As used herein "peptide" refers to an amino acid sequence, whether from naturally occurring sources, or from synthetic origin, connected by a peptide bond, having at least two (2) amino acids, which can be modified or derivatized by modifying groups. U.S. Pat. No. 5,610,271 discloses synthetic peptides that can associate with opioid receptors. This patent is incorporated herein by reference in its entirety for its disclosure related to synthetic peptides.

As used herein "analgesic peptide" refers to a peptide that when administered to a patient suffering with pain, can reduce pain sensations in the patient. Typically, the peptides herein comprise and amino acid sequence of less than 20 amino acids, such as less than 10 amino acids, or about 2 to 8 amino acids, and are capable of binding opioid receptors in the central nervous system.

As used herein "cell receptor" includes pain-related receptors.

As used herein, "diketopiperazine" or "DKP" includes diketopiperazines and salts, derivatives, analogs and modifications thereof falling within the scope of the general Formula 1, wherein the ring atoms $E_1$ and $E_2$ at positions 1 and 4 are either N and at least one of the side-chains $R_1$ and $R_2$ located at positions 3 and 6 respectively contains a substituted amino and/or carbonyl-containing group and a carboxylic acid (carboxylate) group. Compounds according to Formula 1 include, without limitation, diketopiperazines, diketomorpholines and diketodioxanes and their substitution analogs.

Formula 1

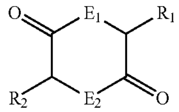

In some embodiments. $R^1$ has 1 to 20 carbon atoms or 4 to 12 carbon atoms; 1-6 oxygen atoms or 2-4 oxygen atoms; 0-2 nitrogen atoms; and any necessary hydrogen atoms. In some embodiments. $R^1$ is $—R^a\text{-G-}R^b—CO_2H$.

In some embodiments, $R^2$ has 1 to 20 carbon atoms or 4 to 12 carbon atoms; 1-6 oxygen atoms or 2-4 oxygen atoms; 0-2 nitrogen atoms; and any necessary hydrogen atoms. In some embodiments, $R^2$ is $R^a\text{-G-}R^b—CO_2H$.

With respect to any relevant structural representation, such as $—R^a\text{-G-}R^b—CO_2H$, each $R^3$ may independently be $—(CH_2)_a—$, wherein a is 0, 1, 2, 3, 4, 5, 6, 7, 8, 9, or 10.

With respect to any relevant structural representation, such as $—R^a\text{-G-}R^b—CO_2H$, each G may independently be NH, CO, $CO_2$, CONH, or NHCO.

With respect to any relevant structural representation, such as $—R^a\text{-G-}R^b—CO_2H$, $R^b$ may be $—(CH_2)_b—$; wherein b is 0, 1, 2, 3, 4, 5, 6, 7, 8, 9, or 10; or a $C_{2-10}$ alkenylene, such as $—CH{=}CH—$, $—CH_2CH{=}CH—$, etc.

Diketopiperazines, in addition to making aerodynamically suitable microparticles, dissolve rapidly at physiologic pH thereby releasing the active agent for absorption into the circulation. Diketopiperazines can be formed into particles that incorporate a drug or particles onto which a drug can be adsorbed. The combination of a drug and a diketopiperazine can impart improved drug stability. These particles can be administered by various routes of administration. As dry powders these particles can be delivered by inhalation to specific areas of the respiratory system, depending on particle size. Additionally, the particles can be made small enough for incorporation into an intravenous suspension dosage form. Oral delivery is also possible with the particles incorporated into suspensions, tablets or capsules.

In one embodiment, the diketopiperazine is 3,6-bis(N-fumaryl-4-aminobutyl)-2,5-diketopiperazine, or 3,6-di(fumaryl-4-aminobutyl)-2,5-diketopiperazine (fumaryl diketopiperazine, FDKP). The FDKP can comprise microparticles in its acid form or salt forms which can be aerosolized or administered in a suspension.

In another embodiment, the DKP is a derivative of 3,6-di (4-aminobutyl)-2,5-diketopiperazine, which can be formed by (thermal) condensation of the amino acid lysine. Exemplary derivatives include dicarboxylic acid derivatives such as 3,6-di(succinyl-4-aminobutyl)-, 3,6-di(maleyl-4-aminobutyl)-, 3,6-di(glutaryl-4-aminobutyl)-, 3,6-di(malonyl-4-aminobutyl)-, 3,6-di(oxalyl-4-aminobutyl)-, and 3,6-di(fumaryl-4-aminobutyl)-2,5-diketopiperazine. The use of DKPs for drug delivery is known in the art (see for example U.S. Pat. Nos. 5,352,461, 5,503,852, 6,071,497, and 6,331,318, each of which is incorporated herein by reference for all that it teaches regarding diketopiperazines and diketopiperazine-mediated drug delivery). The use of DKP salts is described in U.S. Pat. No. 7,820,676, which is hereby incorporated by reference for all it teaches regarding diketopiperazine salts. Pulmonary drug delivery using DKP microparticles is disclosed in U.S. Pat. No. 6,428,771, which is hereby incorporated by reference in its entirety. Further details related to adsorption of active agents onto crystalline DKP particles can be found in U.S. Pat. Nos. 7,799,344 and 7,803,404, which are hereby incorporated by reference in their entirety.

Drug delivery system: As used herein, "drug delivery system" refers to a system for delivering one or more active agents. U.S. Pat. No. 6,703,381 discloses methods for delivering therapeutic compounds across the blood-brain barrier. This patent is incorporated herein by reference in its entirety for its disclosure related to delivering therapeutic compounds across the blood-brain barrier.

Dry powder: As used herein, "dry powder" refers to a fine particulate composition that is not suspended or dissolved in a propellant, carrier, or other liquid, or appears to be dry to an ordinary person. It is not meant to necessarily imply a complete absence of all water molecules.

Microparticles: As used herein, the term "microparticles" includes particles of micron size range, such as generally 0.5 to 100 microns in diameter, or less than 10 microns in diameter. Various embodiments will entail more specific size ranges. The microparticles can be assemblages of crystalline plates with irregular surfaces and internal voids as is typical of those made by pH controlled precipitation of the DKP acids. In such embodiments the active agents can be entrapped by the precipitation or drying processes or coated onto the crystalline surfaces of the microparticle. U.S. Pat. Nos. 7,799,344 and 7,804,404, both of which are incorporated by reference herein in their entirety, include examples of making suitable microparticles. The microparticles can also be spherical shells or collapsed spherical shells comprising DKP salts with the active agent dispersed throughout. Typically such particles can be obtained by spray drying a co-solution of the DKP and the active agent. U.S. Pat. No. 7,820,676, which is incorporated by reference herein in its entirety, includes examples of suitable spray drying methods. The DKP salt in such particles can be amorphous. The forgoing descriptions should be understood as exemplary. Other forms of microparticles are contemplated and encompassed by the term.

Percent respirable fraction per fill (% RF/Fill): As used herein "% RF/Fill" refers to the amount of powder particles emitted from an inhaler, or drug delivery system, which particles are of size in the respirable range and can be smaller than 5.8 μm, normalized by the total amount of powder filled into inhaler or drug delivery system. In some embodiments, the inhaler can be reusable comprising replaceable cartridges containing the dry powder. In other embodiments, the inhaler is manufactured containing the formulation for single use.

Dry powder formulations of the inhalation systems can comprise active agents for the treatment of acute or chronic pain. In one embodiment, the dry powder formulation can be used for treating pain directly or indirectly associated with central or peripheral nervous system involvement, including, for example, headaches such as migraines; post-operative pain, and pain associated with one or more diseases, including, but not limited to cancer, renal disease, immune disorders including, autoimmune disease, a peripheral neuropathy, a central neuropathy, a traumatic abnormality, a cerebral vascular accident, postoperative pain, dental pain, direct trauma, infection, HIV infection, small pox infection, herpes infection, toxic exposure, exposure to arsenic, exposure to lead, cancer, invasive cancer, congenital defect, phantom limb pain, encephalitis, rheumatoid arthritis, fibromyalgias, spinal root lesions, spinal root impingement, back pain, multiple sclerosis, chronic pain, fibrous tissue pain, muscle pain, tendon pain, ligament pain, pain associated with diarrhea, irritable bowel syndrome, abdominal pain, chronic fatigue syndrome, and spasms, and the like.

In an exemplary embodiment herewith, the method for treating pain comprises providing to a subject an inhalable pharmaceutical composition comprising a dry powder comprising one or more receptor agonist peptides. The receptor agonists can be, for example, alpha-MSH receptor agonists, or opioid receptor agonists, or the like. In one embodiment, the dry powder comprises a diketopiperazine, including, N-substituted-3,6-aminoalkyl-2,5-diketopiperazines. In this and other embodiments, the diketopiperazine can be 2,5-diketo-3,6-di(4-X-aminobutyl)piperazine wherein X—OH is a dicarboxylic acid, for example, X may be fumaryl, succinyl, glutaryl, maleyl, malonyl, oxalyl, or a pharmaceutically acceptable salt thereof.

In one embodiment, the dry powder optionally can contain a carrier molecule and/or pharmaceutically-acceptable excipients, including amino acids including, leucine, isoleucine, glycine, and methionine; surfactants such as polysorbates, and sugars, including mannitol, lactose, trehalose, raffinose and the like. In an embodiment herewith, the analgesic composition comprises one or more receptor agonist peptides and a carrier comprising a diketopiperazine, which composition can be delivered to the patient using a dry powder inhaler.

In one embodiment, the analgesic composition or formulation comprises microparticles. In embodiments the microparticles can comprise a diketopiperazine, for example 3,6-bis(N-fumaryl-4-aminobutyl)-2,5-diketopiperazine, or 3,6-bis(N-fumaryl-4-aminobutyl)-2,5-diketopiperazine disodium salt, and a peptide having an amino acid sequence comprising, for example, less than 30 amino acids, or less than 29 amino acids, or less than 28 amino acids, or less than 27 amino acids, or less than 26 amino acids, or less than 25 amino acids, or less than 24 amino acids, or less than 23 amino acids, or less than 22 amino acids, or less than 21 amino acids, or less than 20 amino acids, or less than 19 amino acids; or less than 18 amino acids; or less than 17 amino acids; or less than 16 amino acids; or less than 15 amino acids; or less than 14 amino acids; or less than 13 amino acids; or less than 12 amino acids; or less than 11 amino acids; or less than 10 amino acids; or less than 9 amino acids; or less than 8 amino acids; or less than 7 amino acids; or less than 6 amino acids; or less than 5 amino acids; or less than 4 amino acids; or less than 3 amino acids; wherein said peptide binds to at least one cell receptor which modulates pain.

In certain embodiments, the analgesic composition comprises an analgesic peptide; wherein the analgesic peptide comprises greater than 5% of the weight of an inhalable dry powder composition and the powder comprises microparticles of an N-substituted-3,6-aminoalkyl-2,5-diketopiperazines. In this embodiment, the diketopiperazine can be 3,6-bis(N-X-4-aminobutyl)-2,5-diketopiperazine, wherein X—OH is a $C_{2-20}$, $C_{2-10}$, or $C_{2-5}$ dicarboxylic acid, or a salt thereof, for example X may be fumaryl, succinyl, glutaryl, maleyl, malonyl, oxalyl, or a pharmaceutically acceptable salt thereof. In a particular embodiment, the analgesic composition comprises a diketopiperazine having the formula 3,6-bis(N-fumaryl-4-aminobutyl)-2,5-diketopiperazine, or 3,6-bis(N-fumaryl-4-aminobutyl)-2,5-diketopiperazine disodium salt or dipotassium salt.

In a particular embodiment, the compositions comprise peptides or derivatives thereof that, for example, bind to cell receptors, or directly or indirectly affect cell receptor agonists. These cell receptors can include, for example, opioid receptors, alpha-MSH receptors, and the like. In embodiments the opioid receptors can include, for example, a μ opioid receptors, a δ opioid receptors, a κ opioid receptors, combinations of one or more of the receptors thereof, or all three receptors on cells in the central or peripheral nervous systems. In one embodiment, the peptide can be either δ (delta) opioid receptor agonists or μ opioid receptor agonists. In another embodiment, the peptide can bind nonspecifically to δ opioid, μ opioid or κ opioid receptors, or combinations thereof to bring about reduction or abolishment of the sensation of pain. In one particular embodiment, the composition for treating pain comprises a peptide or a peptide derivative which is substantially a κ opioid receptor-selective agonist. In certain embodiments herewith, the κ opioid receptor-selective agonist peptides and/or derivatives thereof can bind selectively to neurons in the peripheral nervous system. In this and other embodiments, the analgesic composition comprises a peptide having an amino acid composition comprising at least three amino acids selected from the group consisting of glycine, alanine, valine, leucine, methionine, threonine, asparagine, glutamine, cysteine, lysine, arginine, histidine, aspartic acid, glutamic acid, phenylalanine, isoleucine, norleucine, tyrosine, serine, proline, and tryptophan. In an aspect of this embodiment, the analgesic peptide comprises at least two amino acids which are phenylalanine groups or derivatives thereof. In an embodiment, the peptide is a tetrapeptide. In an embodiment the tetrapeptide comprises at least one phenylalanine group.

In certain embodiments, the amino acids can be modified, altered, or changed. For example, conservative amino acid changes may be made, which although they alter the primary sequence of the peptide, may not normally alter its function. Conservative amino acid substitutions typically include substitutions within the following groups:

glycine, alanine;
valine, isoleucine, leucine;
aspartic acid, glutamic acid;
asparagine, glutamine:
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g. by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are peptides which have been modified using ordinary molecular biological techniques so as to improve their resistance to proteolytic degradation or to optimize solubility properties. For example, as used herein "Dmt" refers to dimethyltyrosine. Analogs of such peptides include those containing residues other than naturally occurring L-amino acids, e.g., D-amino acids or non-naturally occurring synthetic amino acids. The peptides of the invention are not limited to products of any of the specific exemplary processes listed herein.

In addition to substantially full length polypeptides, the present invention provides for biologically active fragments of the polypeptides.

In an embodiment, the analgesic composition comprises a peptide comprising at least three amino acids selected from: arginine, phenylalanine, leucine, isoleucine, norleucine, tyrosine, serine, proline, and tryptophan.

In an embodiment, the analgesic composition comprises a peptide comprising at least three amino acids selected from: glycine, alanine, valine, leucine, isoleucine, methionine, proline, or phenylalanine.

In an embodiment, the analgesic composition comprises a peptide comprising at least three amino acids selected from: serine, threonine, asparagine, glutamine, tyrosine, cysteine, lysine, arginine, histidine, or aspartic acid.

In an embodiment, the analgesic composition comprises a peptide comprising glutamic acid, arginine, phenylalanine, leucine, isoleucine, norleucine, tyrosine, serine, proline, or tryptophan.

In some embodiments, the peptide lacks glycine.
In some embodiments, the peptide lacks alanine.
In some embodiments, the peptide lacks valine.
In some embodiments, the peptide lacks leucine.
In some embodiments, the peptide lacks isoleucine.
In some embodiments, the peptide lacks methionine.
In some embodiments, the peptide lacks proline.
In some embodiments, the peptide lacks phenylalanine.
In some embodiments, the peptide lacks tryptophan.
In some embodiments, the peptide lacks serine.
In some embodiments, the peptide lacks threonine.
In some embodiments, the peptide lacks asparagine.
In some embodiments, the peptide lacks glutamine.
In some embodiments, the peptide lacks tyrosine.
In some embodiments, the peptide lacks cysteine.
In some embodiments, the peptide lacks lysine.
In some embodiments, the peptide lacks arginine.
In some embodiments, the peptide lacks histidine.
In some embodiments, the peptide lacks aspartic acid.
In some embodiments, the peptide lacks glutamic acid.

In some embodiments, the analgesic compositions can comprise at least one peptide comprising an amino acid sequence of from three to twenty amino acids in length, such as, for example, 3 amino acids in length, or 4 amino acids in length, or 5 amino acids in length, or 6 amino acids in length, or 7 amino adds in length, or 8 amino acids in length, or 9 amino acids in length, or 10 amino acids in length, or 11 amino acids in length, or 12 amino acids in length, or 13 amino acids in length, or 14 amino acids in length, or 15 amino acids in length, or 16 amino acids in length, or 17 amino acids in length, or 18 amino acids in length, or 19 amino acids in length, or 20 amino adds in length, or the like.

In an embodiment, the analgesic peptide comprises at least two amino acids which are phenylalanine groups or derivatives thereof; in a further aspect the phenylalanine residues are adjacent and in a still further aspect the pair of phenylalanine residues is at the N-terminal end of the peptide. In an embodiment, the peptide is a tetrapeptide which comprises at least one phenylalanine group. In an aspect of this embodiment the phenylalanine residue is at the C-terminal end of the peptide, which can be amidated, and is adjacent to a serine residue. In an alternative aspect the phenylalanine residue is at an internal position and is adjacent to an arginine residue.

In some embodiments, the peptide can comprise an amino acid sequence selected from the group consisting of (D)Phe-(D)Phe-(D)Ile-(D)Arg-$NH_2$ (SEQ ID NO: 1), (D)Phe-(D) Phe-(D)Nle-(D)Arg-$NH_2$ (SEQ ID NO: 2), Trp-(D)Pro-Ser-Phe-$NH_2$ (SEQ ID NO: 3), Trp-(D)Ser-Ser-Phe-$NH_2$ (SEQ ID NO: 4); Dmt-D-Arg-Phe-Lys-$NH_2$ (SEQ ID NO: 5), Ac-His-(D)Phe-Arg-(D)Trp-Gly-$NH_2$ (SEQ ID NO: 6), and Ac-Nle-Gln-His-(D)Phe-Arg-(D)Trp-Gly-$NH_2$ (SEQ ID NO:7).

In a particular embodiment, a method of treating pain sensation comprises administering to a subject in need of said treatment a therapeutically effective amount of a pharmaceutical composition comprising a pharmaceutically acceptable amount of μ opioid receptor agonist in a composition comprising 3,6-bis(N-fumaryl-4-aminobutyl)-2,5-diketopiperazine or 3,6-bis(N-fumaryl-4-aminobutyl)-2,5-diketopiperazine disodium salt. In certain embodiments, the pharmaceutical composition can comprise a pharmaceutically acceptable carrier or other inactive agents. In some embodiments, the μ opioid receptor agonist is a peptide that can cross the blood-brain barrier and can bind to the μ opioid receptor in brain cells. In another aspect of this embodiment, the pharmaceutical composition can comprise a δ opioid receptor agonist in the dry powder. In another aspect of this embodiment, the pharmaceutical composition can comprise a κ opioid receptor agonist in the dry powder. In other embodiments, the peptide can be primarily a κ opioid receptor agonist but also bind to either δ (delta) opioid receptors or μ opioid receptors as an agonist. In another embodiment, the peptide can bind nonspecifically to δ opioid, μ opioid or κ opioid receptors, or combinations thereof to bring about reduction or abolishment of pain sensation. In a particular embodiment, the opioid receptor agonist is a tetrapeptide. In some embodiments, for example, the peptide can have an amino acid sequence selected from the group consisting of (D)Phe-(D)Phe-(D)Ile-(D)Arg-$NH_2$ (SEQ ID NO: 1), (D)Phe-(D)Phe-(D)Nle-(D)Arg-$NH_2$ (SEQ ID NO: 2), Trp-(D)Pro-Ser-Phe-$NH_2$ (SEQ ID NO: 3), Trp-(D)Ser-Ser-Phe-$NH_2$ (SEQ ID NO: 4); Dmt-D-Arg-Phe-Lys-$NH_2$ (SEQ ID NO: 5), Ac-His-(D)Phe-Arg-(D)Trp-Gly-$NH_2$ (SEQ ID NO: 6), and Ac-Nle-Gln-His-(D)Phe-Arg-(D)Trp-Gly-$NH_2$ (SEQ ID NO:7).

The amount of opioid receptor agonist composition can vary depending on the subject's requirements, for example, in amounts of 1 mg or greater. In example embodiments, the amount of peptide opioid receptor agonist in a dry powder for pulmonary inhalation can be administered in a range of from about 1 to about 50 mg. In one embodiment, the amount of dry powder to be administered can be greater than 50 mg. In some embodiments, the dry powders made by the present method can optionally comprise an amino acid such an aliphatic amino acid, for example, alanine, glycine, leucine, isoleucine, norleucine, methionine at amounts ranging from about 0.5% to about 30% by weight. In one particular embodiment, the dry powder composition comprises the amino acid L-leucine. The opioid receptor agonist composition can further comprise a pharmaceutically acceptable sugar, for example, monosaccharides, disaccharides, oligosaccharides, and the like, including, mannitol, xylitol, lactose, trehalose, raffinose, and the like.

In embodiments, the compositions are effective in treating pain without, or with reduced, traditional opioid side effects, including, respiratory depression, gastrointestinal distress, addiction, somnolescence, tolerance, nausea, constipation, and the like.

In an embodiment, the method provides one or more receptor binding peptides or derivatives thereof to a patient in need of treatment of acute or chronic pain. The method comprises selecting one or more receptor agonist peptides; providing a drug delivery system comprising a composition comprising one or more receptor agonist peptides to a patient, and administering a therapeutically effective amount of one or more receptor agonist peptides in a dry powder. In embodiments the receptor can be, for example, an opioid receptor, or an alpha-MSH receptor, or the like.

In one embodiment, the method comprises administering to a patient suffering with acute or chronic pain and in need of treatment, an analgesic composition of the invention, such as, for example, one comprising a diketopiperazine and a peptide.

In one embodiment, a method is provided comprising providing a drug delivery system for rapid administration of an active agent to a patient with severe pain and in need of treatment and administering the active agent to the subject's circulation. In a particular embodiment, the drug delivery system is designed for drug delivery by inhalation and comprises an inhalation apparatus comprising a dry powder inhaler configured to have a container with a chamber for holding a dry powder in a containment configuration and a dosing configuration, wherein the dry powder comprises a pharmaceutical formulation comprising one or more than one antinociceptive peptides and/or derivatives thereof for immediate delivery of the peptides or derivatives thereof. In one embodiment, the drug delivery system is configured for pulmonary inhalation wherein the dry powder comprises microparticles comprising a carrier molecule and the peptides for delivery to the pulmonary circulation in a therapeutically effective manner. In this and other embodiments, the drug delivery system comprises a dry powder inhaler comprising a container, including a cartridge and a dry powder formulation comprising an antinociceptive peptide.

Disclosed herein are methods and compositions for treating pain with a drug delivery system which can comprise pulmonary delivery. In an exemplary embodiment, the systems can include dry powder inhalers for single or multiple uses, as well as containers, for example, cartridges for dry powder inhalers, and the like.

In particular embodiments herewith, the analgesic composition comprises a diketopiperazine having the formula 3,6-bis(N-fumaryl-4-aminobutyl)-2,5-diketopiperazine, or 3,6-bis(N-fumaryl-4-aminobutyl)-2,5-diketopiperazine disodium salt.

In a particular embodiment, a method of treating pain is provided, comprising administering to a subject in need of treatment an analgesic composition comprising a dry powder comprising microparticles of 3,6-bis(N-fumaryl-4-aminobutyl)-2,5-diketopiperazine, or 3,6-bis(N-fumaryl-4-aminobutyl)-2,5-diketopiperazine salt, including, the disodium salt, dipotassium salt and any salt produced by a cation which salt has the appropriate solubility, and a peptide selected from the group consisting of (D)Phe-(D)Phe-(D)Ile-(D)Arg-$NH_2$ (SEQ ID NO: 1), (D)Phe-(D)Phe-(D)Nle-(D)Arg-$NH_2$ (SEQ ID NO: 2), Trp-(D)Pro-Ser-Phe-$NH_2$ (SEQ ID NO: 3), and Trp-(D)Ser-Ser-Phe-$NH_2$ (SEQ ID NO: 4).

In embodiments wherein the diketopiperazine is 2,5-diketo-3,6-di(4-X-aminobutyl)piperazine; wherein X is succinyl, glutaryl, maleyl, malonyl, oxalyl or fumaryl; or a pharmaceutically acceptable salt thereof, the composition may be an inhalable dry powder formulation further comprising a pharmaceutically acceptable carrier or excipient, including but not limited to, polysorbates, amino acids, for example, glycine, leucine, isoleucine, methionine; polysaccharides, for example, dextrans; polylactides, polyglycolides, copolymers of polylactide and glycolide thereof, and the like.

In another exemplary embodiment, a method is provided for treating pain, which method comprises providing to a patient a composition comprising an analgesic peptide in an amount greater than 0.25%, 0.5%, 1%, 2%, 5%, 10%, 25% or 50% by weight of the total powder of the microparticle to be administered to the patient; administering to the patient in need of treatment the composition by pulmonary inhalation the peptides using a dry powder inhaler. In one embodiment, the administration is given by oral inhalation with an inhaler for single use and self-administration, the inhaler comprising a container containing the dry powder. The single use, disposable inhaler is manufactured to contain the dry powder composition in containment conditions and wherein the dry powder is exposed to ambient conditions prior to use.

In another embodiment, a method for treating pain comprises the step of administering to the patient in need of treatment, a dry powder composition, comprising a μ opioid receptor agonist, a δ opioid receptor agonist, or a κ opioid receptor agonist, wherein the dry powder composition is administered by pulmonary inhalation of the dry powder composition using a breath powered, dry powder inhaler comprising a cartridge. For example, the inhaler is a multiple use inhaler adapted with a unit dose cartridge containing the dose to be delivered and wherein the cartridge is discarded after use to make room for a new dose. The inhaler can also be configured for a single use and disposable and is manufactured containing the dry powder composition in a single dose. In one embodiment herewith, the dry powder comprises 3,6-bis(N-fumaryl-4-aminobutyl)-2,5-diketopiperazine or 3,6-bis(N-fumaryl-4-aminobutyl)-2,5-diketopiperazine salt, including, disodium salt, dipotassium salt, and the like.

In embodiments described herein, the drug delivery system is non-invasive and has additional advantages over other methods of drug delivery, for example, oral, subcutaneous and intravenous administration of drug products such as proteins and peptides, which products are sensitive to enzymatic deactivation or degradation in the gastrointestinal tract as well as local peripheral and vascular tissue before reaching the target site.

The inhalation system comprises dry powder inhalers which can be breath-powered, compact, reusable or disposable systems, which can have various shapes and sizes, and comprise a system of airflow conduit pathways for the effective and rapid delivery of dry powder medicaments. In one embodiment, the inhaler can be a unit dose, reusable or disposable inhaler that can be used with or without a cartridge as disclosed in U.S. Publication Nos. U.S. 20090308390; U.S. 20090308391, U.S. 2009030392, U.S. 201000197565, which disclosures are incorporated herein by reference for the relevant subject matter they teach. By use without a cartridge we refer to systems in which a container or cartridge-like structures are provided, which are integral to the inhaler, and the inhaler is for a single use and disposable. Alternatively, in some embodiments, the systems comprise a cartridge which is provided separately and installed in the inhaler for use, for example, by the user for self-administration. In this embodiment, the inhaler can be a reusable inhaler and a new cartridge is installed in the inhaler at every use. In another embodiment, the inhaler can be a multidose inhaler, disposable or reusable, which can be used with single unit dose cartridges installed in the inhaler or cartridge-like structures built-in or structurally configured as part of the inhaler; wherein a dose can be dialed in at the time of need.

Embodiments

1. An inhalable, analgesic composition comprising microparticles of a diketopiperazine and a peptide comprising less than 20 amino acids; wherein said composition is effective at relieving pain.

2. The analgesic composition of embodiment 1, wherein the peptide comprises at least three amino independently selected from arginine, phenylalanine, leucine, isoleucine, norleucine, tyrosine, serine, proline, and tryptophan.

3. The analgesic composition of any of the preceding embodiments, wherein the peptide is an opioid receptor agonist.

4. The analgesic composition of any of the preceding embodiments, wherein the peptide comprises an amino acid sequence of from three to eight amino acids in length.

5. The analgesic composition of any of the preceding embodiments, wherein the peptide comprises four amino acids and the composition is for pulmonary administration.

6. The analgesic composition of any of the preceding embodiments, wherein the peptide comprises: (D)Phe-(D)Phe-(D)Ile-(D)Arg-$NH_2$ (SEQ ID NO: 1), (D)Phe-(D)Phe-(D)Nle-(D)Arg-$NH_2$ (SEQ ID NO: 2), Trp-(D)Pro-Ser-Phe-$NH_2$ (SEQ ID NO: 3), Trp-(D)Ser-Ser-Phe-$NH_2$ (SEQ ID NO: 4); Dmt-D-Arg-Phe-Lys-$NH_2$ (SEQ ID NO: 5), Ac-His-(D)Phe-Arg-(D)Trp-Gly-$NH_2$ (SEQ ID NO: 6), or Ac-Nle-Gln-His-(D)Phe-Arg-(D)Trp-Gly-$NH_2$ (SEQ ID NO:7).

7. The analgesic composition of any of the preceding embodiments, wherein the peptide binds to a μ opioid receptor, a δ opioid receptor, or a κ opioid receptor, or combinations of receptors thereof, of cells in the central or peripheral nervous systems.

8. The analgesic composition of any of the preceding embodiments, wherein the peptide is a κ opioid receptor agonist.

9. The analgesic composition of any of the preceding embodiments, wherein the composition is a dry powder, and the peptide is at least 0.25% of the weight of the composition.

10. The analgesic composition of any of the preceding embodiments, wherein the composition is a dry powder for inhalation and comprises microparticles having a volumetric mean geometric diameter less than 6 μm in diameter.

11. The analgesic composition of any of the preceding embodiments, wherein the diketopiperazine is an N-substituted-3,6-aminoalkyl-2,5-diketopiperazine.

12. The analgesic composition of any of the preceding embodiments, wherein the diketopiperazine is 2,5-diketo-3,6-di(4-X-aminobutyl)piperazine wherein X is fumaryl, succinyl, glutaryl, maleyl, malonyl, oxalyl, or a pharmaceutically acceptable salt thereof.

13. The analgesic composition of any of the preceding embodiments, wherein the diketopiperazine is 3,6-bis(N-fumaryl-4-aminobutyl)-2,5-diketopiperazine, or 3,6-bis(N-fumaryl-4-aminobutyl)-2,5-diketopiperazine disodium salt.

14. The analgesic composition of any of the preceding embodiments, wherein the peptide binds a pain-related receptor.

14B. A dry powder for pulmonary inhalation comprising the analgesic composition of any of the preceding embodiments.

15. A method for treating pain, comprising administering to a subject in need of treatment a therapeutically effective amount of the analgesic composition of any of embodiments 1-14B using a dry powder drug delivery system comprising a dry powder inhaler configured with a container to hold said analgesic composition in a containment configuration and in a dosing configuration.

16. The method of embodiment 15, wherein the analgesic composition is a dry powder comprising a peptide that binds to an opiate receptor.

17. The dry powder of embodiment 16, wherein the diketopiperazine is 3,6-bis(N-fumaryl-4-aminobutyl)-2,5-diketopiperazine, or 3,6-bis(N-fumaryl-4-aminobutyl)-2,5-diketopiperazine disodium salt.

EXAMPLES

The following examples are included to demonstrate certain embodiments disclosed herein. It should be appreciated by those of skill in the art that the techniques disclosed in the examples elucidate representative techniques that function well in the practice of the present invention. However, those of skill in the art should, in light of the present disclosure, appreciate that many changes can be made in the specific embodiments that are disclosed and still obtain a like or similar result without departing from the spirit and scope of the invention.

Example 1

Preparation of Inhalation Powders

Dry powder formulations for inhalation have been prepared from several of these novel tetrapeptide analgesics. Powders containing 3,6-bis(N-fumaryl-4-aminobutyl)-2,5-diketopiperazine (FDKP) or 3,6-bis(N-fumaryl-4-aminobutyl)-2,5-diketopiperazine disodium salt ($Na_2FDKP$) and an analgesic peptide were made containing different amount of each peptide, for example, 10% (w/w), 15% (w/w), 25% (w/w) and 50% (w/w) were prepared at 250 mg to 600 mg scale by either lyophilizing a suspension or spray drying a solution.

To prepare inhalation powder containing 15% (w/w) of the tetrapeptide having the amino acid sequence Trp-(D)ser-Ser-Phe-$NH_2$ (SEQ ID NO: 4), for example, a 10% (w/w) stock solution of the peptide was made (37.49 mg of peptide was dissolved in 337.35 mg of 2% (w/w) acetic acid) and mixed gently into a suspension of FDKP microparticles. The pH of the suspension was adjusted to 4.5 by adding small aliquots of 1:4 ratio of ammonium hydroxide to deionized water. Samples of the suspension mixture were taken for adsorption studies at initial pH value of the suspension, at several pH values during titration and at pH 4.5. Supernatant from the suspension were transferred to filter tubes and centrifuged. The suspension (10 μL) and filtered supernatant samples were transferred into vials containing 990 μL of 100 mM sodium bicarbonate buffer, pH 9.5 for assay by high pressure liquid chromatography (HPLC) analysis. The remaining suspension was pelleted into small crystallization dishes containing liquid nitrogen and lyophilized at 200 mTorr. The shelf temperature was ramped from −45° C. to 25° C. at 0.2° C./min and then held at 25° C. for at least 48 hours during the drying step.

For spray drying, feed solutions were prepared by adding $Na_2FDKP$, L-leucine, and peptide (D)Phe-(D)Phe-(D)Nle-(D)Arg-$NH_2$ (SEQ ID NO: 2) to de-ionized water with mixing. The target peptide content of the final powders made was 25% and 50% in the powders. For a target of 25% content, for example, 170 mg of the peptide was used and 408.8 mg of $Na_2FDKP$, 101.9 mg of L-leucine and deionized water 23.43 g. For a 50% peptide content in the powder formulation, 310.5 mg of peptide, 216.5 mg of $Na_2FDKP$, 93.4 mg of L-leucine and 23.40 g of deionized water were used. The pH of the feed solutions were 6.95 (25% load) and 5.66 (50% load), respectively. The feed solutions were mixed and the pH adjusted. The solutions were spray dried using the following conditions: inlet temperature of 165° C., outlet temperature of 75° C., aspirator set at 90%, atomization flow using nitrogen gas at 57 mm rotameter, collection point set at high efficiency cyclone, nozzle chiller set at 10° C. and a vacuum pressure of −40 mBar. The suspensions were sprayed dried and samples of the powders were used for analysis using an HPLC method.

Characterization—

Peptide content was assayed using an HPLC method, which utilizes a Waters Alliance 2695 HPLC equipped with a 2487 dual wavelength detector or an Agilent 1200 Series HPLC equipped with a diode array/multiple wavelength detector and 6210 time of flight LC/MS or 6130 quadrupole LC/MS. The samples (5 μL injection each at 8° C.) were analyzed using a Phenomenex Luna Phenyl-Hexyl column (3.0×150 mm, 3 μm) at 30° C. for 45 minutes and at a wavelength of 210 nm using water and trifluoroacetic acid (TEA) at a ratio of 1000 to 1 as mobile phase A and methanol: tetrahydrofuran (THF):TFA (900:100:1) as mobile phase B. Samples were analyzed at a flow rate of 0.3 mL/min. Sample content was determined using a standard sample having a peptide concentration of 1.0 mg/mL and 9 mg/mL FDKP.

Aerodynamic performance of the powders was measured by Andersen cascade impaction (ACI) with dry powders inhalers as described in FIGS. 15C through 15K of U.S. patent application Ser. No. 12/484,125 (US 2009/00308390); Ser. No. 12/484,129 (US 2009/0308391) and Ser. No. 12/484,137 (US 2009/0308392), which disclosures are incorporated herein by reference for their teaching of the relevant subject matter. Particle size distribution was measured by a laser diffraction method using a Sympatec RODOS M powder disperser as described in U.S. patent application Ser. No. 12/727,179 (U.S. 2010/0238457); which disclosure is incorporated herein by reference for its teaching of the relevant subject matter. Moisture content was also measured by thermogravimetric analysis (TGA) and particle morphology was examined by field emission scanning electron microscopy (SEM).

Adsorption Study—

Samples from different batch preparations of five different peptides prepared by the lyophilization method were analyzed. The supernatant samples were transferred to 1.5 mL, 0.22 μm filter tubes and centrifuged. The suspension and filtered supernatant samples (500 μL each) were transferred into 50 mL volumetric flasks and brought to volume with 100 mM sodium bicarbonate buffer, pH 9.5. The solutions were transferred to suitable vials for assay and analysis by HPLC. The results are shown in Table 1 below from lyophilized powders. Samples 1, 2, 3, 4, and 5 represent samples taken from five different batches of inhalation powders prepared using five different, unique peptides.

TABLE 1

| | | Attribute Peptide Powder Sample No. | | | | |
|---|---|---|---|---|---|---|
| | | 1 | 2 | 3 | 4 | 5 |
| | | MKC Lot # | | | | |
| | | A | B | C | D | F |
| Peptide Assay (% peptide) | | 15.2 | 14.9 | 15.0 | 13.7 | 15.9 |
| Aerodynamic performance by ACI (Gen2C) | RF/fill | 46.5% | 63.2% | 68.3% | 52.3% | 54.3% |
| | CE | 99.0% | 98.3% | 96.9% | 99.7% | 97.1% |
| Extent of adsorption | Initial (pH) | 4.7% (pH3.9) | * (pH3.9) | * (pH3.5) | 34.5% (pH3.5) | 0.5% (pH4.0) |
| | Final (pH 4.5) | 4.2% | 6.5% | 18.9% | 13.9% | 6.5% |

* Indicates adsorption was measured at less than zero

The data in Table 1 illustrate that the target peptide content intended (15%) correlates with the results obtained in each batch of inhalation powder made. The data also indicate the excellent aerodynamic performance for each inhalation powder since at least 45% of the powder filled in the cartridge is delivered in the respirable range (RF/fill>45%), wherein greater than 96% of the cartridge powder content is emitted from the inhalers tested. The data also show that adsorption of the peptide onto the FDKP varied depending on the peptide, from 4.2% for Sample No. 1 to 19% for Sample No. 3 at pH 4.5.

The chromatograms from the HPLC analysis resolved two peaks when compared to the standards, i.e., a peak corresponding to FDKP and a second peak corresponding to the peptide under analysis for each of the powders made. USP resolution values for each FDKP-peptide pair ranged from 11.83-33.50 indicating excellent resolution. Tailing factors calculated ranged from 1.81-2.32 indicating asymmetric peak shape for peptides Trp-(D)Ser-Ser-Phe-$NH_2$ (SEQ ID NO: 4), Ac-His-(D)Phe-Arg-(D)trp-Gly-$NH_2$ (SEQ ID NO: 6), and (D)Phe-(D)Phe-(D)Ile-(D)Arg-$NH_2$ (SEQ ID NO: 1) at 1 mg/mL.

FDKP-peptide solutions were kept at room temperature for 19 days to evaluate stability. There was substantially no degradation observed for all peptides in solution with FDKP during the experiment.

Peptide content of the powders made using $Na_2$FDKP was measured using the HPLC method, and data from ACI aerodynamic performance of the powders are provided in Table 2 below.

TABLE 2

| Sample ID | % RF/ fill | % CE* | % LOD (TGA)** | $X_{50}$++ (μm) 0.5 bar | $X_{50}$++ (μm) 3.0 bar | Peptide Assay (%) As-is | Peptide Assay (%) Dry basis |
|---|---|---|---|---|---|---|---|
| 1 | 41.7 | 87.0 | 7.98 | 2.7 | 2.4 | 25.3 | 27.5 |
| 2 | 43.8 | 87.6 | 8.06 | 3.3 | 2.4 | 46.9 | 51.0 |

*CE denotes cartridge emptying or content released from inhaler in use from total.
**LOD denotes content loss on drying from original amount
++$X_{50}$ denotes volumetric mean geometric diameter Table 2 data illustrates that the ACI data for the two powders containing 25% and 50% peptide content prepared with $Na_2$FDKP were similar with respect to respirable fraction in the total powder content of the inhaler tested. That is, one powder formulation yielded about 42% RF/fill with 87% of powder content in the test inhaler/cartridge system was emitted using a batch powder having 25% content of (D)Phe-(D)Phe-(D)Nle-(D)Arg-$NH_2$ (SEQ ID NO: 2). For the powder having 50% peptide content, the powder produced a 44% RF/fill with 88% of the powder content emitted from the inhaler during testing. Median size of the primary particles (3.0 bar dispersing pressure) was 2.4 μm for both powders. At a low dispersing pressure (0.5 bar) the powder with 50% peptide content had a slightly higher degree of agglomeration than the powder having a peptide content of 25%, i.e., the high content powder had 3.3 μm median particle size with 79% of the particles measured less 5.8 μm, compared to 2.7 μm with 86% of the particles measure less than 5.8 μm. SEM images show shriveled (raisin-like) particles, some with visible openings which display the inner hollow core and shell of the particles.

Example 2

In Vivo Experiments Using FDKP-Peptide and $Na_2$FDKP-Peptide Compositions

Antinociceptive effect was tested in a mouse tail-withdrawal ("tail-flick," Aldrich et al. 2009) assay in which the tail of a restrained mouse is exposed to water at 55° C. The longer the latency until the mouse flicks its tail away from the water, the more effective the antinociceptive effect of the peptide. There is a time limit to the test and any animal that does not flick its tail ("Tail-flick test") before the time limit is reached is subject reaching this time limit is recorded as demonstrating a 100% effect. Durations shorter than the maximum are reported as a percentage of the time limit. This tail-flick test (also known as the 55° C. warm-water tail withdrawal assay) is an industry acceptable, nonclinical model for assessing the efficacy of analgesics in treating acute pain. To test placebo effect, FDKP (TECHNOSPHERE®) powder (0.5 mg) without any peptide was used in the study. Each animal is tested for baseline tail-withdrawal latency prior to drug administration. Latency to withdraw the tail was subsequently measured in 10 minutes post-drug administration intervals as indicated. A maximum response time of 15 seconds was utilized to prevent tissue damage. Data reported as percent antinociception, as calculated by the following equation: % antinociception is equal to 100 times (test latency minus baseline latency) divided by (15 minus baseline latency).

The tetrapetide, (D)Phe-(D)Phe-(D)Nle-(D)Arg-$NH_2$ (SEQ ID NO: 2, Compound 2) was administered to mice by intraperitoneal (i.p.) injection (3 mg/kg) in a saline solution, and by pulmonary insufflation of a dry powder formulation containing FDKP at various doses, 0.25 mg, 0.125 mg, 0.013 mg, 1.25 μg and 0.13 μg. The tail-flick test was performed for a period of time after administration. The results of the study are shown in FIG. 1 as antinociception effect versus time (dose response). The data show that all doses of the tetrapeptide rapidly provided near-complete antinociception. The effect of the i.p. injection decayed almost linearly with time. When insufflated, the effect was saturated at higher doses with a plateau of approximately 30 minutes at the 0.125 mg dose and 50-55 minutes at the 0.25 mg dose. The results show a clear dose response was evident for the peptides used. Placebo powder produced a negligible effect on nociception.

Example 3

Figure 2:
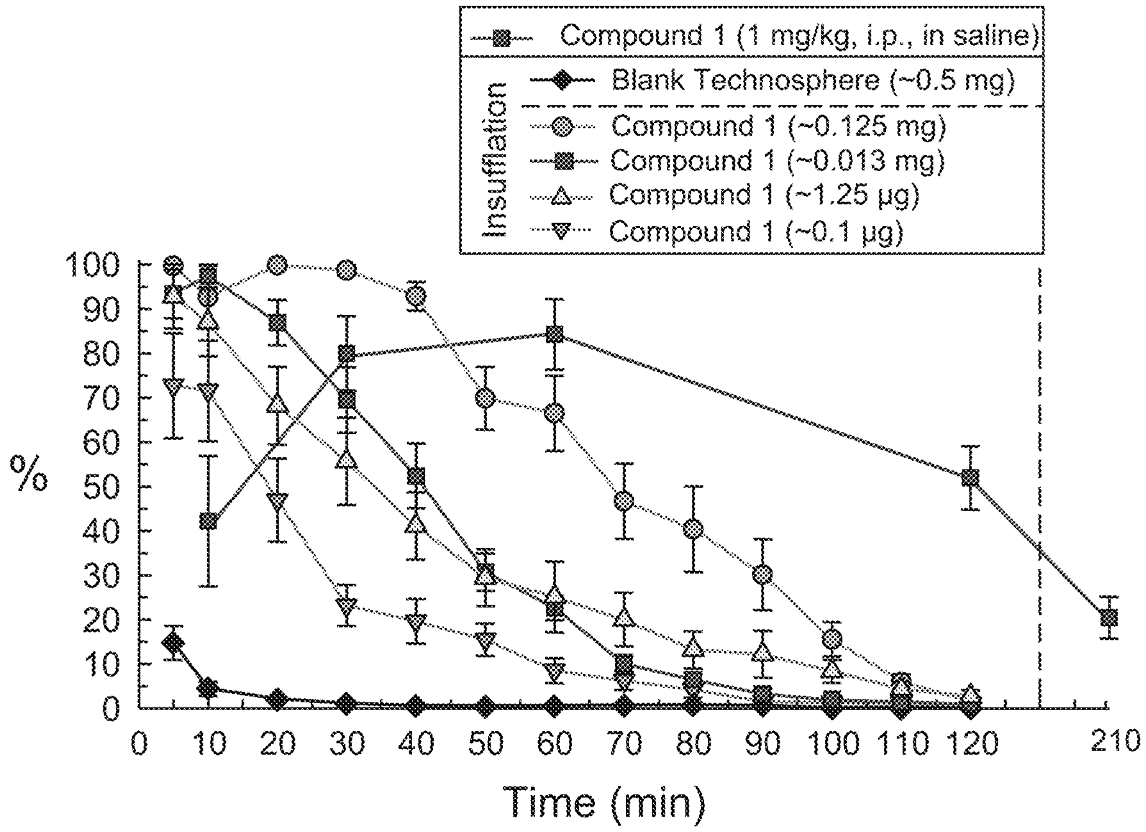
FIG. 2 depicts a graph showing data from 55° C. warm-water tail withdrawal ("Tail-flick") experiments in mice treated with a inhalable dry powder formulation comprising a second analgesic peptide and different from that used in FIG. 1 in various amounts of peptide in the same amount of powder administered by insufflation and compared to a control intraperitoneal injection of the peptide and a placebo dry powder formulation.

Experiments were conducted similarly as described in Example 2 above. In this study, a different tetrapeptide, (D)Phe-(D)Phe-(D)Ile-(D)Arg-$NH_2$ (SEQ ID NO: 1, Compound 1) was administered to mice using i.p. injection of 1 mg/kg in saline solution. For insufflation studies, insufflation powder comprising $Na_2$FDKP having varying peptide content (25%, 2.5%, 0.25%, and 0.025%) was administered to mice in a powder dose of 0.5 mg. For the 2.5%, 0.25%, and 0.025% results, the powder containing 25% peptide content made as described in Example 1, above, was diluted with blank FDKP powder to obtain the lower peptide content samples. The results are shown in FIG. 2. The data show the insufflated tetrapeptide (Compound 1) powders provided a rapid antinociceptive effect that was saturated at the highest dose with a plateau lasting approximately 40 minutes. At lower doses, the effect was not saturated but showed a dose response. The injected peptide (D)Phe-(D)Phe-(D)Ile-(D)Arg-$NH_2$ (SEQ ID NO: 1) had the longest duration of effect, but did not have the same rapid onset as the insufflated doses.

Example 4

Experiments were conducted similarly as described in Examples 2 and 3 above. In this study, a dry powder formulation containing tetrapeptide (D)Phe-(D)Phe-(D)Ile-(D)Arg (SEQ ID NO: 1, Compound 1) was administered to mice. A subset of mice was administered an intraperitoneal dose of morphine 10 mg/kg (AUC 6795) of body weight. In addition, one group of mice received an i.p. injection of saline solution; one group received 0.25 mg of blank FDKP/TECHNOSPHERE® powder by insufflation as controls. Another group of mice received 0.125 mg of morphine by insufflation; one group of mice received a powder formulation containing 0.125 mg of peptide (D)Phe-(D)Phe-(D)Ile-(D)Arg-$NH_2$ (SEQ ID NO: 1) and one group of mice received a powder formulation containing 0.125 mg of peptide (D)Phe-(D)Phe-(D)Nle-(D)Arg-$NH_2$ (SEQ ID NO: 2, Compound 2) by insufflation. The mice were monitored for activities related to side effects of morphine and peptide administration, specifically changes in spontaneous locomotion and respiration rates.

Figure 3:
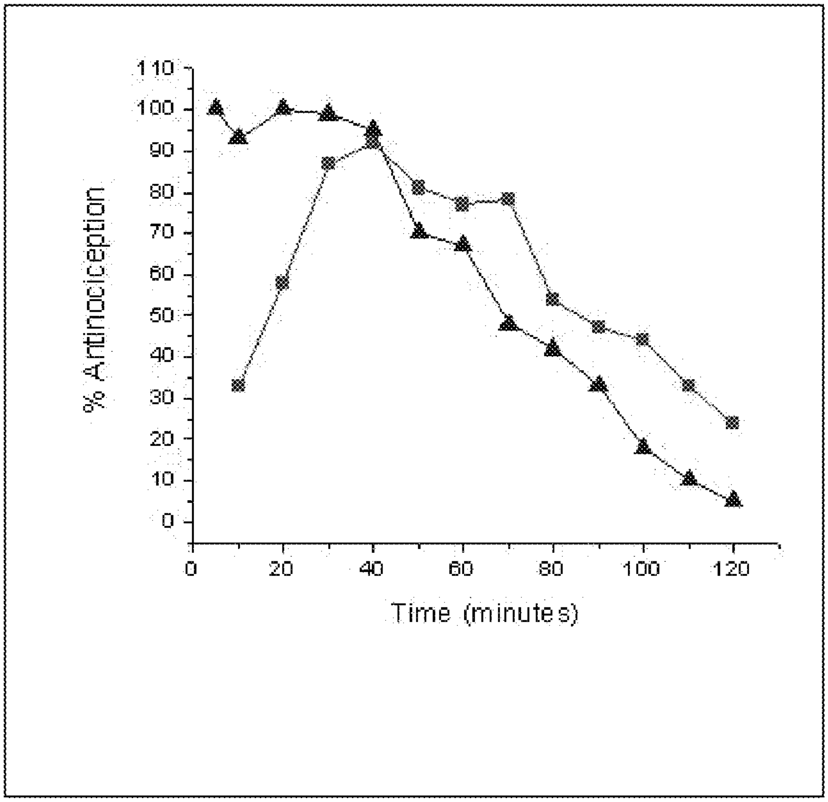
FIG. 3 depicts a graph showing data from 55° C. warm-water tail withdrawal ("Tail-flick") experiments in mice treated with an inhalable dry powder formulation comprising the second analgesic peptide used in FIG. 2 administered by insufflation and compared to an intraperitoneal injection of morphine.
Figure 4A:
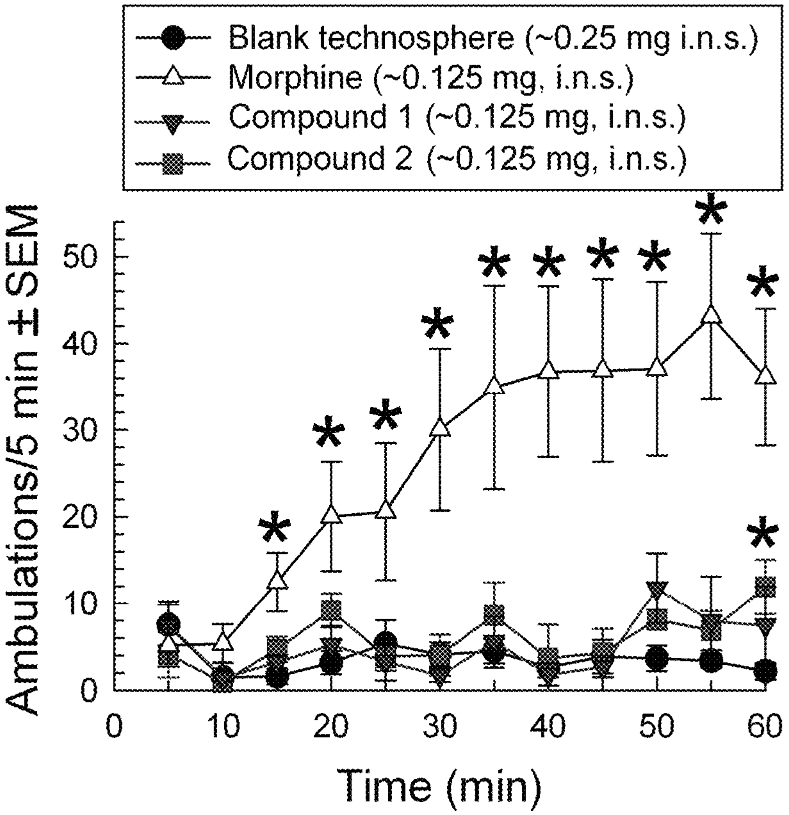
FIGS. 4A and 4B are graphs showing data from experiments measuring spontaneous locomotion and respiration in the comprehensive laboratory animal monitoring system (CLAMS) using mice treated with an inhalable dry powder formulation comprising each of the peptides as described in FIGS. 1 and 2 and compared to a dose of inhalable morphine and blank FDKP powder as placebo.
Figure 4B:
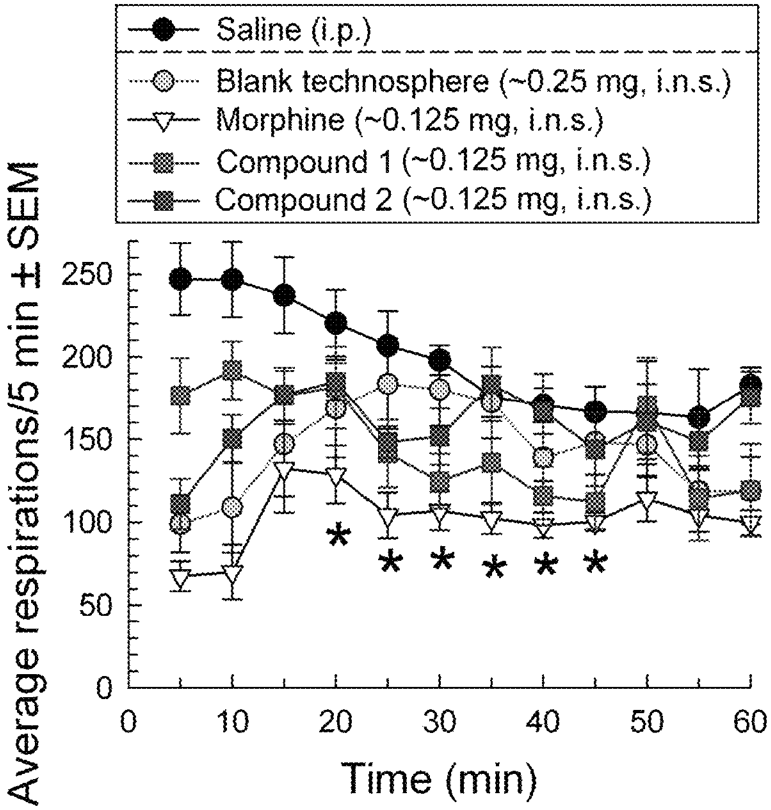

Powder was administered to mice by insufflation at 5 mg/kg of body weight. The responses in the 55° C. warm-water tail withdrawal assay were examined for two hours. The results are shown in FIG. 3. The data demonstrate that insufflated powder inhibits nociception faster than injected morphine (squares). The duration of action of the tetrapeptide on pain (D)Phe-(D)Phe-(D)Ile-(D)Arg-$NH_2$ (SEQ ID NO: 1, Compound 1, triangles) and morphine sulfate is similar. Morphine is known to induce locomotor hyperactivity in mice and depress the rate of respiration. In a comparison study of inhalable morphine powder (triangles) and dry powder formulations comprised of tetrapeptides (Compounds 1 and 2 (squares)) administered by insufflation, these effects were observed in mice administered morphine. In contrast, the ambulation and respiration rates (FIG. 4A, FIG. 4B, respectively) of mice receiving the tetrapeptide powder were comparable to animals receiving placebo (FDKP blank, circles) powder as shown in the figures.

Example 5

Figure 5:
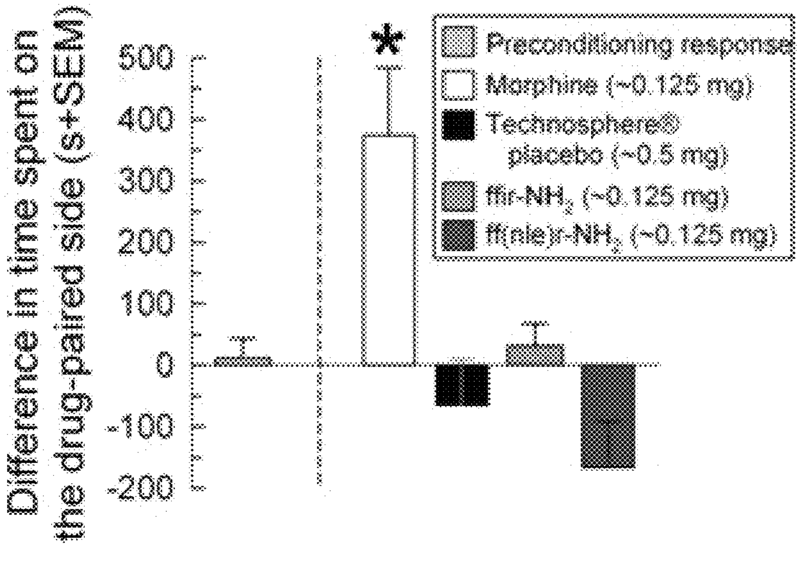
FIG. 5 depicts a graph showing data from conditioned place preference experiments using mice treated with an inhalable dry powder formulation comprising each of the peptides as described in FIGS. 1 and 2 and compared to a dose of inhalable morphine and blank FDKP powder as placebo.

In a conditioned place preference (CPP) study to evaluate the "reward" or "aversive" value of the drug, mice are conditioned to associate one compartment of the apparatus with treatment. The apparatus itself is "balanced," meaning that mice show no initial preference for one chamber over another (FIG. 5, left-most bar). Reinforcing agents result in an increased place preference for the drug-paired compartment, whereas aversive agents result in a decreased place preference. The experiments were conducted similarly as described in the previous examples. Mice were insufflated with 0.125 mg of morphine or powder formulations containing 0.125 mg of tetrapeptide (D)Phe-(D)Phe-(D)Ile-(D)Arg-$NH_2$ (SEQ ID NO: 1, Compound 1) or (D)Phe-(D)Phe-(D)Nle-(D)Arg-$NH_2$ (SEQ ID NO: 2, Compound 2). To test placebo effect, additional mice were insufflated with FDKP (TECHNOSPHERE®) powder (0.5 mg) without any peptide. The results of these experiments are shown in FIG. 5. The data show that mice insufflated with the placebo powder or the powder containing the tetrapeptide (D)Phe-(D)Phe-(D)Ile-(D)Arg-$NH_2$ (SEQ ID NO: 1, Compound 1) or (D)Phe-(D)Phe-(D)Nle-(D)Arg-$NH_2$ (SEQ ID NO: 2, Compound 2) showed no preference for the paired compartment. In contrast, mice treated with morphine exhibited a strong preference for the associated compartment, confirming the expected reward effect provided by the drug.

Accordingly, dry powder formulations for inhalation comprising peptides can provide opioid-like pain relief with fewer adverse effects than current, commercially available analgesics. The inhalation powder has been administered to mice by pulmonary insufflation. In a nonclinical model of acute pain (the 55° C. warm-water tail withdrawal assay), the dry powder formulations comprising the peptides demonstrated analgesic activity comparable to injected morphine without the typical opioid side effects. Unlike mice treated with morphine, those given the dry powder formulations comprising the peptides surprisingly did not exhibit depressed respiration or alterations in spontaneous locomotor activity. Nor did they exhibit a place-conditioning response, a behavior associated with a "reward" after receiving the FDKP/opioid receptor agonist peptide dry powder formulation.

Example 6

A 48 yr. old female patient reports headache pain to her doctor. Following examination of the patient, the doctor prescribes an analgesic composition containing a FDKP/SEQ (D)Phe-(D)Phe-(D)Nle-(D)Arg-$NH_2$ (SEQ ID NO: 2, Compound 2) composition prepared as described in the previous Examples. The analgesic composition is 15% peptide. The analgesic composition is administered with a reusable inhaler calibrated to provide a dose of 5 mg/kg of body weight. The patient reports the elimination of her headache pain.

Example 7

A 22 yr. old male patient undergoing chemotherapy reports stomach pain to his doctor. Following examination of the patient, the doctor prescribes an analgesic composition containing a FDKP/(D)Phe-(D)Phe-(D)Ile-(D)Arg-$NH_2$ (SEQ ID NO: 1, Compound 1) composition prepared as described in the previous Examples. The analgesic composition is 15% peptide. The analgesic composition is administered with a reusable inhaler calibrated to provide a dose of 5 mg/kg of body weight. The patient reports the elimination of his stomach pain.

Example 8

A 63 yr. old female patient reports back pain to her doctor. Following examination of the patient, the doctor prescribes an analgesic composition containing a FDKP/Trp-(D)Pro-Ser-Phe-$NH_2$ (SEQ ID NO: 3, Compound 3), composition prepared as described in the previous Examples. The analgesic composition is 15% peptide. The analgesic composition is administered with a reusable inhaler calibrated to provide a dose of 4 mg/kg of body weight. The patient reports the elimination of her back pain.

Example 9

A 28 yr. old male patient reports dental pain to his doctor. Following examination of the patient, the doctor prescribes an analgesic composition containing an $Na_2$FDKP/Ac-His-(D)Phe-Arg-(D)Trp-Gly-$NH_2$ (SEQ ID NO: 6, Compound 6) composition prepared as described in the previous Examples. The analgesic composition is 10% peptide. The analgesic composition is administered with a reusable inhaler calibrated to provide a dose of 7 mg/kg of body weight. The patient reports the elimination of his dental pain.

Example 10

A 33 yr. old female patient reports pain due to multiple sclerosis to her doctor. Following examination of the patient, the doctor prescribes an analgesic composition containing an $Na_2$FDKP/(D)Phe-(D)Phe-(D)Nle-(D)Arg-$NH_2$ (SEQ ID NO: 2, Compound 2) composition prepared as described in the previous Examples. The analgesic composition is 20% peptide. The analgesic composition is administered with a reusable inhaler calibrated to provide a dose of 3 mg/kg of body weight. The patient reports the elimination of her multiple sclerosis pain.

Example 11

A 58 yr. old male patient reports muscle pain to his doctor. Following examination of the patient, the doctor prescribes an analgesic composition containing a FDKP/Ac-His-(D)Phe-Arg-(D)Trp-Gly-$NH_2$ (SEQ ID NO: 6, Compound 6) composition prepared as described in the previous Examples. The analgesic composition is 15% peptide. The analgesic composition is administered with a reusable inhaler calibrated to provide a dose of 5 mg/kg of body weight. The patient reports the elimination of his muscle pain.

Example 12

An 8 yr. old male patient reports pain from a broken arm to his doctor. Following examination of the patient, the doctor prescribes an analgesic composition containing a $Na_2$FDKP/Trp-(D)Ser-Ser-Phe-$NH_2$ (SEQ ID NO: 4, Compound 4) composition prepared as described in the previous Examples. The analgesic composition is 25% peptide. The analgesic composition is administered with a reusable inhaler calibrated to provide a dose of 2 mg/kg of body weight. The patient reports the elimination of his pain.

Example 13

A 55 yr. old female patient reports her low pain threshold to her dentist. Following examination of the patient and prior to the dental procedure, the dentist administers an analgesic composition containing a FDKP/Ac-Nle-Gln-His-(D)Phe-Arg-(D)Trp-Gly-$NH_2$ (SEQ ID NO:7, Compound 7) composition prepared as described in the previous Examples. The analgesic composition is 10% peptide. The analgesic composition is administered with a single-use inhaler designed to provide a dose of 5 mg/kg of body weight. The patient reports no pain during the dental procedure.

While the invention has been particularly shown and described with reference to particular embodiments, it will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative, elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. An inhalable, analgesic composition comprising microparticles of a diketopiperazine and a peptide comprising less than 20 amino acids; wherein said composition is effective at relieving pain, wherein the peptide is an opioid receptor agonist.

2. The inhalable analgesic composition of claim 1, wherein the peptide comprises at least three amino acids independently selected from arginine, phenylalanine, leucine, isoleucine, norleucine, tyrosine, serine, proline, and tryptophan.

3. The inhalable analgesic composition of claim 2, wherein the peptide is an amino acid sequence of from three to eight amino acids in length.

4. The inhalable analgesic composition of claim 3, wherein the peptide is a four amino acid sequence and the composition is for pulmonary administration.

5. The inhalable analgesic composition of claim 3, wherein the peptide comprises: (D)Phe-(D)Phe-(D)Ile-(D)Arg-$NH_2$ (SEQ ID NO: 1) or (D)Phe-(D)Phe-(D)Nle-(D)Arg-$NH_2$ (SEQ ID NO: 2).

6. The inhalable analgesic composition of claim 1, wherein the peptide binds to a μ opioid receptor, a δ opioid receptor, or a κ opioid receptor, or combinations of receptors thereof, on cells in the central or peripheral nervous systems.

7. The inhalable analgesic composition of claim 1, wherein the peptide is a κ opioid receptor agonist.

8. The inhalable analgesic composition of claim 1, wherein the composition comprises a dry powder, and the peptide comprises at least 0.25% of the weight of the composition.

9. The inhalable analgesic composition of claim 1, wherein the composition comprises a dry powder for inhalation and comprises microparticles having a volumetric mean geometric diameter less than 8 μm in diameter.

10. The inhalable analgesic composition of claim 1, wherein the diketopiperazine is an N-substituted-3,6-aminoalkyl-2,5-diketopiperazine.

11. The inhalable analgesic composition of claim 10, wherein the diketopiperazine is 3,6-bis(N-fumaryl-4-aminobutyl)-2,5-diketopiperazine, or 3,6-bis(N-fumaryl-4-aminobutyl)-2,5-diketopiperazine disodium salt.

12. The inhalable analgesic composition of claim 1, wherein the diketopiperazine is 3,6-bis(N-X-4-aminobutyl)-2,5-diketopiperazine, wherein X is fumaryl, succinyl, glutaryl, maleyl, malonyl, oxalyl, or a pharmaceutically acceptable salt thereof.

13. The inhalable analgesic composition of claim 1, further comprising one or more pharmaceutical carrier or excipients selected from amino acids, sugars and surfactants.

14. The inhalable analgesic composition of claim 13, wherein the amino acids comprise at least one of leucine, isoleucine, glycine and methionine.

15. The inhalable analgesic composition of claim 13, wherein the sugars comprise at least one of mannitol, lactose, trehalose and raffinose.

16. A dry powder for pulmonary inhalation comprising the inhalable analgesic composition of claim 11.

17. A method for treating pain, comprising administering to a subject in need of treatment a therapeutically effective amount of an inhalable analgesic composition comprising microparticles of a diketopiperazine and a peptide comprising less than 20 amino acids using a dry powder drug delivery system, wherein the peptide is an opioid receptor agonist.

18. The method of claim 17, wherein the dry powder drug delivery system comprises a dry powder inhaler configured with a container to hold said inhalable analgesic composition in a containment configuration and in a dosing configuration.

19. The method of claim 17, wherein the inhalable analgesic composition comprises a dry powder comprising a peptide that binds to an opiate receptor.

20. The method of claim 19, wherein the diketopiperazine is 3,6-bis(N-fumaryl-4-aminobutyl)-2,5-diketopiperazine, or 3,6-bis(N-fumaryl-4-aminobutyl)-2,5-diketopiperazine dosodium salt.

21. The method of claim 19, wherein the peptide comprises: (D)Phe-(D)Phe-(D)Ile-(D)Arg-$NH_2$ (SEQ ID NO: 1) or (D)Phe-(D)Phe-(D)Nle-(D)Arg-$NH_2$ (SEQ ID NO: 2).

22. The method of claim 19, wherein the peptide binds to a μ opioid receptor, a δ opioid receptor, or a κ opioid receptor, or combinations of receptors thereof, of cells in the central or peripheral nervous systems.

23. An inhalable analgesic composition comprising 3,6-bis (N-X-4-aminobutyl)-2,5-diketopiperazine wherein X is fumaryl or a pharmaceutically acceptable salt thereof, and a synthetic peptide having the amino acid sequence: (D)Phe- (D)-Phe-(D)Ile-(D)Arg-$NH_2$ (SEQ ID NO: 1) or (D)Phe-(D)Phe-(D)Nle-(D)Arg-$NH_2$ (SEQ ID NO: 2).

24. The inhalable analgesic composition of claim 23, further comprising one or more amino acids selected from the group consisting of leucine, isoleucine, glycine and methionine.

25. The inhalable analgesic composition of claim 23, wherein the peptide binds to a κ opioid receptor on cells in the central or peripheral nervous systems.

* * * * *

SEQUENCE LISTING

```
<160> NUMBER OF SEQ ID NOS: 7

<210> SEQ ID NO 1
<211> LENGTH: 4
<212> TYPE: PRT
<213> ORGANISM: Artificial Sequence
<220> FEATURE:
<223> OTHER INFORMATION: anti-pain peptide
<220> FEATURE:
<221> NAME/KEY: VARIANT
<222> LOCATION: (1)..(2)
<223> OTHER INFORMATION: Xaa is D-phenylalanine
<220> FEATURE:
<221> NAME/KEY: VARIANT
<222> LOCATION: (3)..(3)
<223> OTHER INFORMATION: Xaa is D-isoleucine
<220> FEATURE:
<221> NAME/KEY: VARIANT
<222> LOCATION: (4)..(4)
<223> OTHER INFORMATION: Xaa is D-arginine

<400> SEQUENCE: 1

Xaa Xaa Xaa Xaa
1


<210> SEQ ID NO 2
<211> LENGTH: 4
<212> TYPE: PRT
<213> ORGANISM: Artificial Sequence
<220> FEATURE:
<223> OTHER INFORMATION: anti-pain peptide
<220> FEATURE:
<221> NAME/KEY: VARIANT
<222> LOCATION: (1)..(2)
<223> OTHER INFORMATION: Xaa is D-phenylalanine
<220> FEATURE:
<221> NAME/KEY: VARIANT
<222> LOCATION: (3)..(3)
<223> OTHER INFORMATION: Xaa is D-norleucine
<220> FEATURE:
<221> NAME/KEY: VARIANT
<222> LOCATION: (4)..(4)
<223> OTHER INFORMATION: Xaa is D-arginine

<400> SEQUENCE: 2

Xaa Xaa Xaa Xaa
1


<210> SEQ ID NO 3
<211> LENGTH: 4
<212> TYPE: PRT
```

<213> ORGANISM: Artificial Sequence
<220> FEATURE:
<223> OTHER INFORMATION: anti-pain peptide
<220> FEATURE:
<221> NAME/KEY: VARIANT
<222> LOCATION: (2)..(2)
<223> OTHER INFORMATION: Xaa us D-proline

<400> SEQUENCE: 3

Trp Xaa Ser Phe
1

<210> SEQ ID NO 4
<211> LENGTH: 4
<212> TYPE: PRT
<213> ORGANISM: Artificial Sequence
<220> FEATURE:
<223> OTHER INFORMATION: anti-pain peptide
<220> FEATURE:
<221> NAME/KEY: VARIANT
<222> LOCATION: (2)..(2)
<223> OTHER INFORMATION: Xaa is D-serine

<400> SEQUENCE: 4

Trp Xaa Ser Phe
1

<210> SEQ ID NO 5
<211> LENGTH: 4
<212> TYPE: PRT
<213> ORGANISM: Artificial Sequence
<220> FEATURE:
<223> OTHER INFORMATION: Dmt-DALDA
<220> FEATURE:
<221> NAME/KEY: VARIANT
<222> LOCATION: (1)..(1)
<223> OTHER INFORMATION: Xaa is dimethytyrosine
<220> FEATURE:
<221> NAME/KEY: VARIANT
<222> LOCATION: (1)..(1)
<223> OTHER INFORMATION: Xaa is dimethyltyrosine
<220> FEATURE:
<221> NAME/KEY: VARIANT
<222> LOCATION: (2)..(2)
<223> OTHER INFORMATION: Xaa is D-arginine

<400> SEQUENCE: 5

Xaa Xaa Phe Lys
1

<210> SEQ ID NO 6
<211> LENGTH: 5
<212> TYPE: PRT
<213> ORGANISM: Artificial Sequence
<220> FEATURE:
<223> OTHER INFORMATION: anti-pain peptide TPI-446
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (2)..(2)
<223> OTHER INFORMATION: Xaa is D-phenylalanine
<220> FEATURE:
<221> NAME/KEY: VARIANT
<222> LOCATION: (4)..(4)
<223> OTHER INFORMATION: Xaa is D-tryptophan

<400> SEQUENCE: 6

His Xaa Arg Xaa Gly
1 5

-continued

```
<210> SEQ ID NO 7
<211> LENGTH: 7
<212> TYPE: PRT
<213> ORGANISM: Artificial Sequence
<220> FEATURE:
<223> OTHER INFORMATION: anti-pain peptide TPI-228
<220> FEATURE:
<221> NAME/KEY: MOD_RES
<222> LOCATION: (1)..(1)
<223> OTHER INFORMATION: ACETYLATION, Nle
<220> FEATURE:
<221> NAME/KEY: VARIANT
<222> LOCATION: (4)..(4)
<223> OTHER INFORMATION: Xaa is D-phenylalanine
<220> FEATURE:
<221> NAME/KEY: VARIANT
<222> LOCATION: (6)..(6)
<223> OTHER INFORMATION: Xaa is D-tryptophan

<400> SEQUENCE: 7

Xaa Gln His Xaa Arg Xaa Gly
1               5
```